(12) United States Patent
Godineau et al.

(10) Patent No.: US 9,969,734 B2
(45) Date of Patent: May 15, 2018

(54) PROCESS FOR THE PREPARATION OF SPIROHETEROCYCLIC PYRROLIDINE DIONES

(71) Applicant: SYNGENTA PARTICIPATIONS AG, Basel (CH)

(72) Inventors: Edouard Godineau, Stein (CH); Tomas Smejkal, Stein (CH); Sophie Pelletier, Basel (CH); Michel Muehlebach, Stein (CH); Regis Jean Georges Mondiere, Stein (CH); Helmars Smits, Stein (CH); Jochen Weckesser, Muenchwilen (CH); Alan James Robinson, Muenchwilen (CH)

(73) Assignee: Syngenta Participations AG, Basel (CH)

( * ) Notice: Subject to any disclaimer, the term of this patent is extended or adjusted under 35 U.S.C. 154(b) by 0 days. days.

(21) Appl. No.: 14/905,575

(22) PCT Filed: Jul. 11, 2014

(86) PCT No.: PCT/EP2014/064922
§ 371 (c)(1),
(2) Date: Jan. 15, 2016

(87) PCT Pub. No.: WO2015/007640
PCT Pub. Date: Jan. 22, 2015

(65) Prior Publication Data
US 2016/0159799 A1 Jun. 9, 2016

(30) Foreign Application Priority Data

Jul. 19, 2013 (EP) ..................................... 13177233
Dec. 9, 2013 (EP) ..................................... 13196335

(51) Int. Cl.
| | | |
|---|---|---|
| *C07D 471/10* | (2006.01) |
| *C07D 209/54* | (2006.01) |
| *C07D 211/94* | (2006.01) |
| *C07D 409/12* | (2006.01) |
| *C07C 231/06* | (2006.01) |
| *C07C 233/65* | (2006.01) |
| *C07C 233/74* | (2006.01) |

(52) U.S. Cl.
CPC .......... *C07D 471/10* (2013.01); *C07C 231/06* (2013.01); *C07C 233/65* (2013.01); *C07C 233/74* (2013.01); *C07D 209/54* (2013.01); *C07D 211/94* (2013.01); *C07D 409/12* (2013.01)

(58) Field of Classification Search
CPC .. C07D 471/10; C07D 409/02; C07D 231/02; C07D 209/54
USPC .......................................................... 546/16
See application file for complete search history.

(56) References Cited

FOREIGN PATENT DOCUMENTS

| | | |
|---|---|---|
| DE | 10239479 A1 | 3/2004 |
| WO | WO2009/049851 A1 | 4/2009 |
| WO | WO2009132453 | * 11/2009 |

OTHER PUBLICATIONS

Spatz, Julia H. et al: "Tetramic acid derivatives via Ugi-Diecl<mann-reaction" in: Tetrahedron Letters 50 (2009), pp. 1705-1707.
Ito, Mitsuru et al: "Synthesis and Insecticidal Activity of Novel N-Oxydihydropyrroles: 4-Hydroxy-3-mesityl-1-methoxymethoxy Derivatives with Various Substituents at the 5-Position" in: Bioorganic & Medicinal Chemistry 11 (2003), Pergamon, pp. 761-768. XP-002447979.
International Search Report for International Patent Application No. PCT/EP2014/064922 dated Sep. 4, 2014.

* cited by examiner

*Primary Examiner* — Rita J Desai
(74) *Attorney, Agent, or Firm* — James Cueva

(57) ABSTRACT

A process for making certain spiroheterocyclic pyrrolidine dione derivatives.

10 Claims, No Drawings

PROCESS FOR THE PREPARATION OF SPIROHETEROCYCLIC PYRROLIDINE DIONES

RELATED APPLICATION INFORMATION

This application is a 371 of International Application No. PCT/EP2014/064922, filed Jul. 11, 2014, which claims priority to European Patent Application No. 13177233.7, filed Jul. 19, 2013, and European Patent Application No. 13196335.7, filed Dec. 9, 2013, the contents of all of which are incorporated herein by reference herein.

The present invention relates to methods to prepare spiroheterocyclic pyrrolidine diones, which are useful for combating and controlling pests such as insect, acarine, mollusc and nematode pests, to new phenylacetylamino-carboxamide intermediates useful in such methods and to processes for preparing such intermediates.

Spiroheterocyclic pyrrolidine dione derivatives for combating and controlling pests such as insect, acarine, mollusc and nematode pests are disclosed, for example in WO 2009/049851 and WO 2010/066780.

A new method for preparing these compounds has now been found, which uses a novel intermediate. Methods of preparing spiroheterocyclic pyrrolidine dione derivatives are described in WO 1998/005638, WO 2004/007448, WO 2009/049851 and WO 2010/066780, with the present invention offering unique methods to prepare such compounds using less process steps (presenting therefore advantages such as higher thoughput capacity and lower amount of waste) as well as more attractive conditions (for example, avoiding the use of very toxic HCN or equivalents). It has been found that the novel intermediate can be converted into spiroheterocyclic pyrrolidine dione derivatives via intermolecular activation. This new process is particularly beneficial as it uses less-expensive reactants. Further, the present invention is suitable for commercial-scale production.

Accordingly, in a first aspect, the present invention provides a process for the preparation of a spiroheterocyclic pyrrolidine dione compound of formula (II)

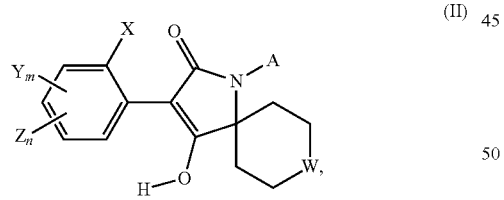
(II)

wherein

X, Y and Z independently of each other are hydrogen, $C_{1-4}$alkyl, $C_{3-6}$cycloalkyl, $C_{1-4}$haloalkyl, $C_{1-4}$alkoxy, $C_{1-4}$haloalkoxy, halogen, cyano, $C_{2-6}$alkenyl, $C_{2-6}$alkynyl, phenyl, or phenyl substituted by $C_{1-4}$alkyl, $C_{1-4}$haloalkyl, halogen or cyano;

m and n, independently of each other, are 0, 1, 2 or 3 and m+n is 0, 1, 2 or 3;

A is hydrogen, $C_{1-6}$alkyl, $C_{1-6}$haloalkyl, $C_{3-6}$cycloalkyl, $C_{3-6}$cycloalkyl($C_{1-4}$)alkyl, $C_{2-6}$alkenyl, $C_{2-6}$haloalkenyl, $C_{3-6}$alkynyl, $C_{1-4}$alkoxy($C_{1-4}$)alkyl, benzyl, phenyl or phenyl substituted by $C_{1-4}$alkyl, $C_{1-4}$haloalkyl, $C_{1-4}$alkoxy, $C_{1-4}$haloalkoxy, halogen or cyano;

W is a group selected from $W^1$ to $W^{15}$:

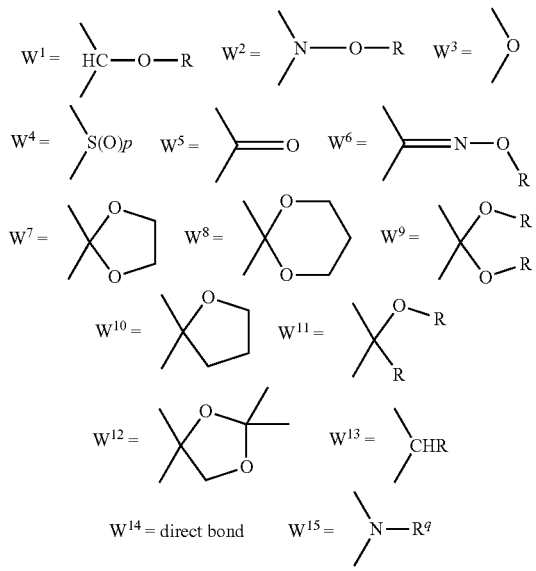

$W^{14}$ = direct bond   $W^{15}$ = \N—$R^q$ wherein R is hydrogen, $C_{1-6}$alkyl, $C_{1-6}$haloalkyl, $C_{1-6}$cyanoalkyl, $C_{2-6}$alkenyl, $C_{2-6}$haloalkenyl, $C_{3-6}$alkynyl, benzyl, $C_{1-4}$alkoxy($C_{1-4}$)alkyl or $C_{1-4}$alkoxy($C_{1-4}$)alkoxy($C_{1-4}$)alkyl;

$R^q$ is R or $Q^2$;

p is 0, 1 or 2; and $Q^2$ is hydrogen, formyl, $C_{1-6}$alkylcarbonyl or $C_{1-6}$alkoxycarbonyl;

which process comprises (a) treating a compound of the formula (I) or a salt thereof with a suitable base in an appropriate solvent (or diluent)

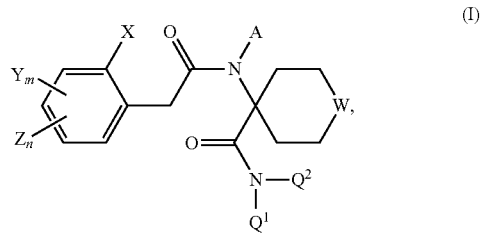
(I)

wherein X, Y, Z, m, n, A and W have the meanings given in the formula (II) above and $Q^1$ is $C_{3-6}$cycloalkyl, $C_{1-6}$alkoxycarbonyl ($C_{1-6}$)alkyl, p-tolylsulfonylmethyl, phenyl or phenyl substituted by one or more substituent selected from the group consisting of $C_{1-4}$alkyl, $C_{1-4}$haloalkyl, $C_{1-4}$alkoxy, halogen, and nitro; and $Q^2$ is hydrogen, formyl, $C_{1-6}$alkylcarbonyl or $C_{1-6}$alkoxycarbonyl;

(b) optionally a compound of formula (III) is included in step (a),

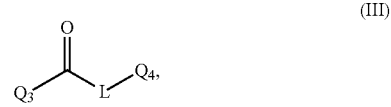
(III)

wherein $Q^3$ is hydrogen, halogen, $C_{1-6}$alkyl or $C_{1-6}$alkoxy, L is O or N($C_{1-6}$alkyl) and $Q^4$ is $C_{1-6}$alkyl, provided the solvent (or diluent), and if necessary the compound of formula (III), is selected to activate the —NQ¹Q² group to become a leaving group.

In a second aspect, the present invention also provides a phenylacetylamino-carboxamide compound of formula (I)

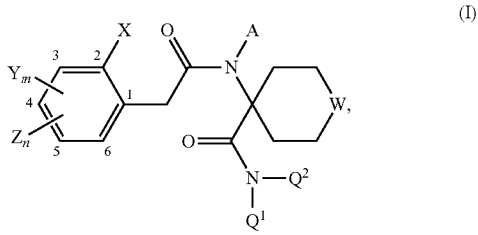

wherein

X, Y and Z independently of each other are hydrogen, $C_{1-4}$alkyl, $C_{3-6}$cycloalkyl, $C_{1-4}$haloalkyl, $C_{1-4}$alkoxy, $C_{1-4}$haloalkoxy, halogen, cyano, $C_{2-6}$alkenyl, $C_{2-6}$alkynyl, phenyl, or phenyl substituted by $C_{1-4}$alkyl, $C_{1-4}$haloalkyl, halogen or cyano;

m and n, independently of each other, are 0, 1, 2 or 3 and m+n is 0, 1, 2 or 3; A is hydrogen, $C_{1-6}$alkyl, $C_{1-6}$haloalkyl, $C_{3-6}$cycloalkyl, $C_{3-6}$cycloalkyl($C_{1-4}$)alkyl, $C_{2-6}$alkenyl, $C_{2-6}$haloalkenyl, $C_{3-6}$alkynyl, $C_{1-4}$alkoxy($C_{1-4}$)alkyl, benzyl, phenyl or phenyl substituted by $C_{1-4}$alkyl, $C_{1-4}$haloalkyl, $C_{1-4}$alkoxy, $C_{1-4}$haloalkoxy, halogen or cyano;

W is a group selected from $W^1$ to $W^{15}$:

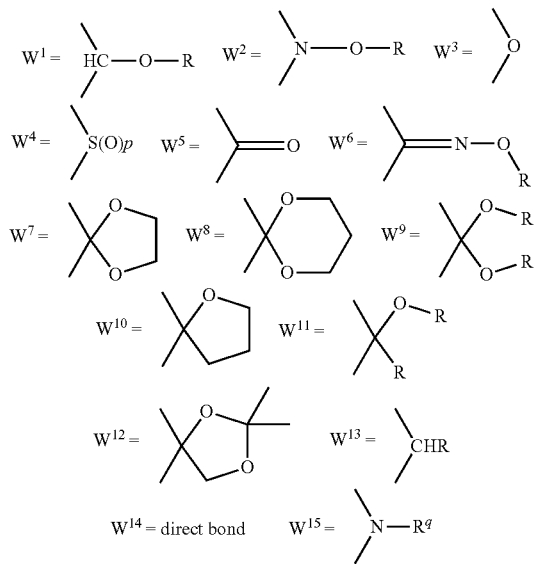

wherein R is hydrogen, $C_{1-6}$alkyl, $C_{1-6}$haloalkyl, $C_{1-6}$cyanoalkyl, $C_{2-6}$alkenyl, $C_{2-6}$haloalkenyl, $C_{3-6}$alkynyl, benzyl, $C_{1-4}$alkoxy($C_{1-4}$)alkyl or $C_{1-4}$alkoxy($C_{1-4}$)alkoxy($C_{1-4}$)alkyl;

$R^q$ is R or $Q^2$;

p is 0, 1 or 2;

$Q^1$ is n-butyl, s-butyl, i-butyl, tert-butyl, $C_{3-6}$cycloalkyl, $C_{1-6}$alkoxycarbonyl ($C_{1-6}$)alkyl, p-tolylsulfonylmethyl, phenyl or phenyl substituted by one or more substituent selected from the group consisting of $C_{1-4}$alkyl, $C_{1-4}$haloalkyl, $C_{1-4}$alkoxy, halogen, and nitro; and $Q^2$ is hydrogen, formyl, $C_{1-6}$alkylcarbonyl, or $C_{1-6}$alkoxycarbonyl; or an acceptable salt or an N-oxide thereof.

In the compounds of the present invention, each alkyl moiety, either alone or as part of a larger group, is a $C_{1-4}$- or $C_{1-6}$-straight or branched chain and is, for example, methyl, ethyl, n-propyl, n-butyl, iso-propyl, sec-butyl, iso-butyl, tert-butyl, n-pentyl, iso-pentyl and n-hexyl. Preferably, each alkyl moiety is a $C_{1-4}$ alkyl, such as methyl, ethyl, n-propyl, n-butyl, iso-propyl, sec-butyl, iso-butyl, and tert-butyl, especially methyl or ethyl.

Alkoxy moiety, either alone or as part of a larger group, has a preferred chain length of from 1 to 4, especially 1 to 2, carbon atoms. Alkoxy is, for example, methoxy, ethoxy, propoxy, iso-propoxy, n-butoxy, iso-butoxy, sec-butoxy or tert-butoxy. Such groups can be part of a larger group such as alkoxyalkyl and alkoxyalkoxyalkyl. $C_{1-4}$alkoxy($C_{1-4}$)alkyl preferably have a chain length of 2 to 4 carbon atoms. Alkoxyalkyl is, for example, methoxymethyl, methoxyethyl, ethoxymethyl, ethoxyethyl, n-propoxymethyl, n-propoxyethyl, iso-propoxymethyl. Alkoxyalkoxyalkyl groups preferably have a chain length of 3 to 8 carbon atoms. Alkoxyalkoxyalkyl is, for example, methoxymethoxymethyl, methoxyethoxymethyl, ethoxymethoxyethyl and ethoxyethoxyethyl. In each of $C_{1-4}$alkoxy($C_{1-4}$)alkyl and $C_{1-4}$alkoxy($C_{1-4}$)alkoxy ($C_{1-4}$)alkyl, the attachment to the remaining part of the compound of formula (I) is by a carbon atom in corresponding alkyl chain.

Halogen is generally fluorine, chlorine, bromine or iodine. This also applies, correspondingly, to halogen in combination with other meanings, such as haloalkyl, haloalkoxy or haloalkenyl.

Haloalkyl groups preferably have a chain length of from 1 to 4 or 1 to 6 carbon atoms, preferably 1 to 2 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl.

The preferred alkenyl and alkynyl radicals having 2 to 6 or 3 to 6 carbon atoms can be straight or branched and can contain more than one double or triple bond, respectively. Examples are vinyl, (E)- or (Z)-propenyl, 2-methyl-propenyl, allyl, 3-methyl-but-2-enyl, ethynyl, prop-1-ynyl, propargyl, butenyl, butynyl, pentenyl and pentynyl.

The cycloalkyl groups preferably have from 3 to 6 ring carbon atoms, for example cyclopropyl, cyclobutyl, cyclopentyl and cyclohexyl. Examples of $C_{3-6}$cycloalkyl($C_{1-4}$) alkyl are cyclopropyl methyl, cyclobutyl methyl, and cyclopentyl methyl, and the ethyl analogs thereof, wherein the $C_{3-6}$cycloalkyl($C_{1-4}$)alkyl is attached to remaining part of compound of formula (I) is by a carbon atom in alkyl chain.

Phenyl, also as part of a substituent such as benzyl, may be substituted, preferably by one or more substituent selected from the group consisting of $C_{1-4}$alkyl, $C_{1-4}$haloalkyl, $C_{1-4}$alkoxy, $C_{1-4}$haloalkoxy, halogen, nitro and cyano. The substituent can be in the ortho, meta and/or para position.

$C_{1-6}$alkylcarbonyl groups preferably have 2 to 5 carbon atoms, including the carbonyl carbon atom. The $C_{1-6}$alkylcarbonyl is attached to remaining part of compound of formula (I) by the carbonyl carbon atom. Examples of $C_{1-6}$alkylcarbonyl are methylcarbonyl, ethylcarbonyl, propylcarbonyl, butylcarbonyl, and a tert-butylcarbonyl.

$C_{1-6}$alkoxycarbonyl groups preferably have 2 to 5 carbon atoms, including the carbonyl carbon atom. The $C_{1-6}$alkoxycarbonyl is attached to remaining part of compound of formula (I) by the carbonyl carbon atom. Examples of $C_{1-6}$alkoxycarbonyl are methoxycarbonyl, ethoxycarbonyl, propyloxycarbonyl, butyloxycarbonyl and a tert-butyloxycarbonyl.

$C_{1-6}$alkoxycarbonyl $(C_{1-6})$alkyl groups preferably have 3 to 6 carbon atoms, including the carbonyl carbon atom. $C_{1-6}$alkoxycarbonyl $(C_{1-6})$alkyl is attached to remaining part of compound of formula (I) by a carbon atom in the alkly group. Examples of $C_{1-6}$alkoxycarbonyl $(C_{1-6})$alkyl are $CH_3OC(O)CH_2$— and $CH_3CH_2OC(O)CH_2$—.

One skilled in the art also recognizes that because in the environment and under physiological conditions salts of chemical compounds are in equilibrium with their corresponding non-salt forms, salts can share the utility of the non-salt forms. Thus, a wide variety of salts of compounds of the invention may be useful. Salts include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids.

Suitable amongst salts can also be the salts of cations. Thus, especially suitable cations are the ions of the alkali metals including sodium, potassium and lithium, of the alkaline earth metals including calcium and magnesium, and of the transition metals including manganese, copper, iron, zinc, cobalt, lead, silver, nickel, and also ammonium or organic ammonium including monoalkylammonium, dialkylammonium, trialkylammonium, tetraalkylammonium, monoalkenylammonium, dialkenylammonium, trialkenylammonium, monoalkynylammonium, dialkynylammonium, monoalkanolammonium, dialkanolammonium, $C_5$-$C_6$-cycloalkylammonium, piperidinium, morpholinium, pyrrolidinium, or benzylammonium, moreover phosphonium ions, sulfonium ions, preferably tri($C_1$-$C_4$-alkyl) sulfonium and sulfoxonium ions, preferably tri ($C_1$-$C_4$-alkyl) sulfoxonium.

Depending on the nature of the group W, compounds of formula (I) may exist in different cis- and trans-isomeric forms. When W is equal to $W^1$, for example, compounds of formula (I) may exist as trans- or cis-isomers:

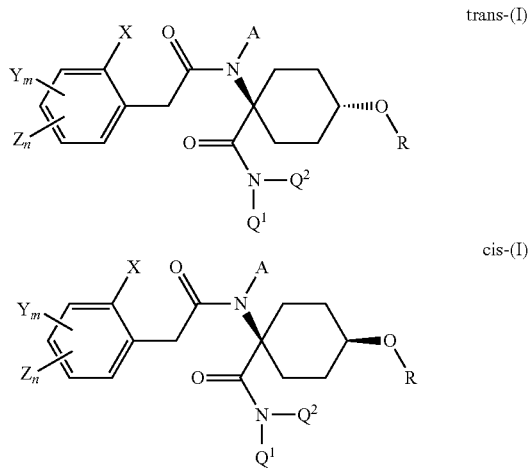

The present invention covers all isomers and mixtures thereof in all proportions Compounds of the formula (I) with cis/trans isomers are $W^1$, $W^4$ for p=1, $W^{10}$, $W^{11}$, $W^{12}$ and $W^{13}$.

Also, when substituents contain double bonds, cis- and trans-isomers can exist. These isomers, too, are within the scope of the claimed compounds of the formula I.

Preferably, X, Y and Z, are selected, independently of one another, from hydrogen, $C_1$-$C_4$alkyl, $C_1$-$C_4$alkoxy and halogen; in particular X, Y and Z, independently of one another, is methyl, ethyl, iso-propyl, n-propyl, methoxy, fluoro, bromo or chloro, when m+n is 1, 2 or 3, in particular, when m+n is 1 or 2.

In an embodiment of the present invention, X is selected from $C_1$-$C_4$alkyl, $C_1$-$C_4$alkoxy and halogen; preferably X is methyl, ethyl, iso-propyl, n-propyl, methoxy, fluoro, bromo or chloro.

In an embodiment of the present invention, Y and Z, independently of each other, are selected from $C_1$-$C_4$alkyl, $C_1$-$C_4$alkoxy, halogen, phenyl and phenyl substituted by $C_{1-4}$alkyl or halogen; preferably Y and Z, independent of each other, are methyl, ethyl, iso-propyl, n-propyl, methoxy, fluoro, chloro, bromo, phenyl or phenyl substituted with halogen, in particular fluoro or chloro; especially suitable are Y or Z at the 4-position when m+n is 1, 2 or 3, in particular, when m+n is 1 or 2.

In another embodiment, n is 1 in the compound of formula (I), Z is at the 4-position and is selected from the group consisting of fluoro, bromo, chloro, methyl, ethyl, iso-propyl and n-propyl. Preferably, Z is methyl, fluoro, bromo or chloro. More preferably, Z is chloro or methyl.

In yet another embodiment, n is 1 in the compound of formula (I), Z is at position 5 and X is selected from the group consisting of bromo, chloro, methyl and ethyl and Z is selected from the group consisting of fluoro, bromo, chloro, methyl, ethyl, iso-propyl and n-propyl. Preferably, Z is methyl, fluoro, bromo or chloro. More preferably, Z is chloro or methyl and X is methyl.

In another embodiment, m and n in the compound of formula (I) are each 1, Y is at the 6-position and X and Y are selected independently from the group consisting of bromo, chloro, methyl and ethyl, and Z is at the 4-position and is selected from the group consisting of methyl, ethyl, fluoro, bromo and chloro. Preferably, X and Y are each methyl with Y at the 6-position and preferably Z is at the 4-position and is chloro or methyl.

In the compounds of the present invention, the substituent A is preferably hydrogen, $C_{1-6}$alkyl, $C_{1-6}$haloalkyl, $C_{2-6}$alkenyl, $C_{3-6}$alkynyl, $C_{1-4}$alkoxy($C_{1-4}$)alkyl, benzyl, phenyl or phenyl substituted by $C_{1-4}$alkyl, $C_{1-4}$haloalkyl, $C_{1-4}$alkoxy, halogen or cyano. Even more preferably A is selected from hydrogen, $C_{1-6}$alkyl, $C_{1-6}$haloalkyl, $C_{2-6}$alkenyl, $C_{3-6}$alkynyl, $C_{1-4}$alkoxy($C_{1-4}$)alkyl, benzyl or phenyl, in particular A is hydrogen, methyl, ethyl, n-propyl, iso-propyl, n-butyl, iso-butyl, sec-butyl, tert-butyl, 2,2,2-trifluoroethyl, allyl, propargyl, methoxymethyl, ethoxymethyl, methoxyethyl, methoxypropyl, benzyl or phenyl.

In one embodiment, A is preferably hydrogen.

In another embodiment, A is preferably $C_{1-6}$alkyl. In a preferred embodiment, A is selected from the group consisting of methyl, ethyl, n-propyl, iso-propyl, n-butyl, iso-butyl, sec-butyl and tert-butyl. In an even more preferred embodiment, A is methyl.

For any one of W selected from $W^1$, $W^2$, $W^6$, $W^9$, $W^{11}$, $W^{13}$, and $W^{15}$ in the compounds of the formula (I), the substituent R, independent of W, is preferably hydrogen, $C_{1-6}$alkyl, $C_{1-6}$haloalkyl, $C_{2-6}$alkenyl, $C_{3-6}$alkynyl, benzyl or $C_{1-4}$alkoxy($C_{1-4}$)alkyl, in particular hydrogen, methyl, ethyl, iso-propyl, n-propyl, tert-butyl, trifluoromethyl, 2,2,2-trifluoroethyl, allyl, propargyl, benzyl, methoxymethyl, ethoxymethyl or methoxyethyl.

Preferably, W is a group selected from one of $W^1$ to $W^6$, and $W^{13}$ to $W^{15}$:

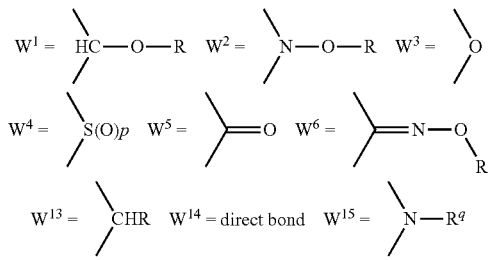

wherein for $W^4$ p is 0, 1 or 2, and for $W^1$, $W^2$, $W^6$ and $W^{13}$, R, independent of W, is preferably hydrogen, $C_{1-6}$alkyl, $C_{1-6}$haloalkyl, $C_{2-6}$alkenyl, $C_{3-6}$alkynyl, benzyl or $C_{1-4}$alkoxy($C_{1-4}$)alkyl, in particular hydrogen, methyl, ethyl, iso-propyl, n-propyl, tert-butyl, trifluoromethyl, 2,2,2-trifluoroethyl, allyl, propargyl, benzyl, methoxymethyl, ethoxymethyl or methoxyethyl, and wherein for $W^{15}$ $R^q$ is preferably hydrogen, $C_{1-6}$alkyl, benzyl or $Q^2$, in particular hydrogen, methyl, ethyl, iso-propyl, n-propyl, tert-butyl, benzyl, formyl, methylcarbonyl, ethylcarbonyl, propylcarbonyl, iso-propylcarbonyl, n-butylcarbonyl or t-butylcarbonyl, methoxycarbonyl, ethoxycarbonyl, propyloxycarbonyl, iso-propyloxycarbonyl, n-butyloxycarbonyl or t-butyloxycarbonyl; more preferably for $W^1$, $W^2$, $W^6$ and $W^{13}$, R, independent of W, is hydrogen, methyl, ethyl, iso-propyl, n-propyl, allyl, propargyl or benzyl and for $W^{15}$ $R^q$ is hydrogen, methyl, ethyl, iso-propyl, n-propyl, tert-butyl, benzyl, formyl, methylcarbonyl, ethylcarbonyl, iso-propylcarbonyl or t-butylcarbonyl, methoxycarbonyl, ethoxycarbonyl, iso-propyloxycarbonyl or t-butyloxycarbonyl. Most preferably, R is methyl for $W^1$, $W^2$ and $W^6$, and hydrogen or methyl for $W^{13}$, and most preferably, $R^q$ is hydrogen, methyl, ethyl, benzyl, formyl, methylcarbonyl, ethylcarbonyl, t-butylcarbonyl, methoxycarbonyl, ethoxycarbonyl or t-butyloxycarbonyl for $W^{15}$.

More preferably, W is a group selected from one of $W^1$ to $W^4$, and $W^{13}$ to $W^{15}$;

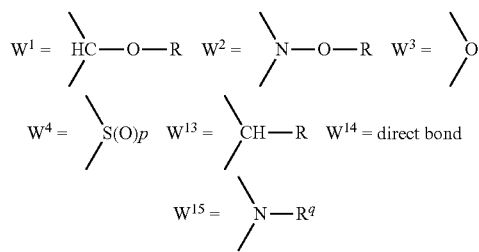

wherein for $W^4$ p is 0, 1 or 2, and for $W^1$, $W^2$ and $W^{13}$, R, independent of W, is preferably hydrogen, $C_{1-6}$alkyl, $C_{1-6}$haloalkyl, $C_{2-6}$alkenyl, $C_{3-6}$alkynyl, benzyl or $C_{1-4}$alkoxy($C_{1-4}$)alkyl, in particular hydrogen, methyl, ethyl, iso-propyl, n-propyl, tert-butyl, trifluoromethyl, 2,2,2-trifluoroethyl, allyl, propargyl, benzyl, methoxymethyl, ethoxymethyl or methoxyethyl, and wherein for $W^{15}$ $R^q$ is preferably hydrogen, $C_{1-6}$alkyl, benzyl or $Q^2$, in particular hydrogen, methyl, ethyl, iso-propyl, n-propyl, tert-butyl, benzyl, formyl, methylcarbonyl, ethylcarbonyl, propylcarbonyl, iso-propylcarbonyl, n-butylcarbonyl or t-butylcarbonyl, methoxycarbonyl, ethoxycarbonyl, propyloxycarbonyl, iso-propyloxycarbonyl, n-butyloxycarbonyl or t-butyloxycarbonyl; more preferably wherein R is methyl for both $W^1$ and $W^2$, and hydrogen or methyl for $W^{13}$, and wherein $R^q$ is hydrogen, methyl, ethyl, benzyl, formyl, methylcarbonyl, ethylcarbonyl, t-butylcarbonyl, methoxycarbonyl, ethoxycarbonyl or t-butyloxycarbonyl for $W^{15}$.

Most preferably, W is a group selected from one of $W^1$ to $W^2$:

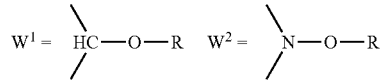

wherein for both $W^1$ and $W^2$, R, independent of W, is preferably hydrogen, $C_{1-6}$alkyl, $C_{1-6}$haloalkyl, $C_{2-6}$alkenyl, $C_{3-6}$alkynyl, benzyl or $C_{1-4}$alkoxy($C_{1-4}$)alkyl, in particular hydrogen, methyl, ethyl, iso-propyl, n-propyl, tert-butyl, trifluoromethyl, 2,2,2-trifluoroethyl, allyl, propargyl, benzyl, methoxymethyl, ethoxymethyl or methoxyethyl; more preferably wherein R is methyl for both $W^1$ and $W^2$.

In an embodiment of the first aspect, $Q^1$ is preferably cyclohexyl, methoxycarbonylmethyl, ethoxycarbonylmethyl, p-tolylsulfonylmethyl, phenyl or phenyl substituted by one or more substituent selected from the group consisting of $C_{1-4}$alkyl, $C_{1-4}$haloalkyl, $C_{1-4}$alkoxy, halogen, and nitro. More preferably, $Q^1$ is cyclohexyl, methoxycarbonylmethyl, ethoxycarbonylmethyl, p-tolylsulfonylmethyl, phenyl or phenyl substituted by one or more substituent selected from the group consisting of methyl, ethyl, iso-propyl, trifluoromethyl, methoxy, ethoxy, fluoro, chloro and nitro. Especially preferred for $Q^1$ is phenyl.

In an embodiment of the second aspect, $Q^1$ is preferably n-butyl, tert-butyl, cyclohexyl, methoxycarbonylmethyl, ethoxycarbonylmethyl, p-tolylsulfonylmethyl, phenyl or phenyl substituted by one or more substituent selected from the group consisting of $C_{1-4}$alkyl, $C_{1-4}$haloalkyl, $C_{1-4}$alkoxy, halogen, and nitro. More preferably, $Q^1$ is n-butyl, tert-butyl, cyclohexyl, methoxycarbonylmethyl, ethoxycarbonylmethyl, p-tolylsulfonylmethyl, phenyl or phenyl substituted by one or more substituent selected from the group consisting of methyl, ethyl, iso-propyl, trifluoromethyl, methoxy, ethoxy, fluoro, chloro and nitro. Especially preferred for $Q^1$ is phenyl.

$Q^2$, independent of the aspects, is preferably hydrogen, formyl, $C_{1-6}$alkylcarbonyl I or $C_{1-6}$alkoxycarbonyl. Even more preferably, $Q^2$ is selected from one of hydrogen, formyl, methylcarbonyl, ethylcarbonyl, propylcarbonyl, iso-propylcarbonyl, n-butylcarbonyl or t-butylcarbonyl, methoxycarbonyl, ethoxycarbonyl, propyloxycarbonyl, iso-propyloxycarbonyl, n-butyloxycarbonyl or t-butyloxycarbonyl. Especially preferred $Q^2$ for compound of formula (I) is hydrogen.

In a further aspect, the present invention provide a compound of formula (I-I),

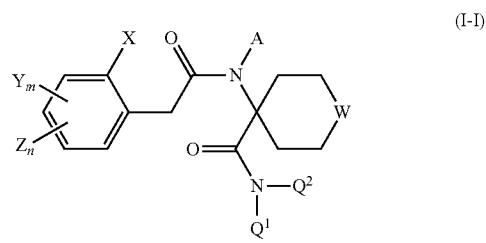

wherein X, Y, Z, m, n, A, W, $Q^1$ is as defined in the second aspect and each embodiment thereof, and $Q^2$ is either formyl, $C_{1-6}$alkylcarbonyl or $C_{1-6}$alkoxycarbonyl, preferably formyl, methylcarbonyl, ethylcarbonyl, methoxycarbonyl or ethoxycarbonyl.

In a preferred embodiment of the second aspect of the invention, for a compound of formula (I), X, Y and Z independently of each other, are selected from hydrogen, methyl, ethyl, iso-propyl, n-propyl, methoxy, fluoro, bromo and chloro, when m+n is 1, 2 or 3, in particular, when m+n is 1 or 2; A is hydrogen, methyl, ethyl, n-propyl, iso-propyl, n-butyl, iso-butyl, sec-butyl, tert-butyl, 2,2,2-trifluoroethyl, allyl, propargyl, methoxymethyl, ethoxymethyl, methoxyethyl, methoxypropyl, benzyl or phenyl; W is a group selected from $W^1$ to $W^4$, and $W^{13}$ to $W^{15}$ (as defined in the second aspect); $Q^1$ is n-butyl, tert-butyl, cyclohexyl, methoxycarbonylmethyl, ethoxycarbonylmethyl, p-tolylsulfonylmethyl, phenyl or phenyl substituted by one or more substituent selected from the group consisting of $C_{1-4}$alkyl, $C_{1-4}$haloalkyl, $C_{1-4}$alkoxy, halogen, and nitro; and $Q^2$ is hydrogen.

In a further preferred embodiment of the second aspect of the invention, for a compound of formula (I), X, Y and Z independently of each other, are selected from hydrogen, methyl and chloro, when m+n is 1, 2 or 3, in particular, when m+n is 1 or 2; A is hydrogen, methyl, allyl, benzyl or phenyl; W is a group selected from $W^1$ to $W^3$, and $W^{13}$ with R being hydrogen or $C_{1-4}$alkyl; $Q^1$ is n-butyl, p-tolylsulfonylmethyl, phenyl or phenyl substituted by one or more substituent selected from the group consisting of $C_{1-4}$alkyl, $C_{1-4}$alkoxy, halogen, and nitro; and $Q^2$ is hydrogen.

In any embodiment of formula (I) herein defined, m and n are each 1 and Y is at position 6 on the phenyl ring and is either hydrogen or methyl, and Z is at position 4 and is selected from chloro, methyl or hydrogen.

Alternatively, in any embodiment of formula (I) herein defined, n is 1 and m is 0, and Z is at position 5 and is methyl.

In a preferred embodiment of the third aspect of the invention, for a compound of formula (I-I), X, Y and Z independently of each other, are selected from hydrogen, methyl, ethyl, iso-propyl, n-propyl, methoxy, fluoro, bromo and chloro, when m+n is 1, 2 or 3, in particular, when m+n is 1 or 2; A is hydrogen, methyl, ethyl, n-propyl, iso-propyl, n-butyl, iso-butyl, sec-butyl, tert-butyl, 2,2,2-trifluoroethyl, allyl, propargyl, methoxymethyl, ethoxymethyl, methoxyethyl, methoxypropyl, benzyl or phenyl; W is a group selected from $W^1$ to $W^4$, and $W^{13}$ to $W^{15}$ (as defined in the second aspect); $Q^1$ is n-butyl, tert-butyl, cyclohexyl, methoxycarbonylmethyl, ethoxycarbonylmethyl, p-tolylsulfonylmethyl, phenyl or phenyl substituted by one or more substituent selected from the group consisting of $C_{1-4}$alkyl, $C_{1-4}$haloalkyl, $C_{1-4}$alkoxy, halogen, and nitro; and $Q^2$ is formyl, $C_{1-6}$alkylcarbonyl or $C_{1-6}$alkoxycarbonyl.

In a further preferred embodiment of the third aspect of the invention, for a compound of formula (I-I), X, Y and Z independently of each other, are selected from hydrogen, methyl, and chloro, when m+n is 1, 2 or 3, in particular, when m+n is 1 or 2; A is is hydrogen, methyl, allyl, benzyl or phenyl; W is a group selected from $W^1$ to $W^3$, and $W^{13}$, with R being hydrogen or $C_{1-4}$alkyl; $Q^1$ is n-butyl, p-tolylsulfonylmethyl, phenyl or phenyl substituted by one or more substituent selected from the group consisting of $C_{1-4}$alkyl, $C_{1-4}$alkoxy, halogen, and nitro; and $Q^2$ is formyl.

Compounds of formula (I) can be prepared by a Ugi-type reaction (Scheme 1).

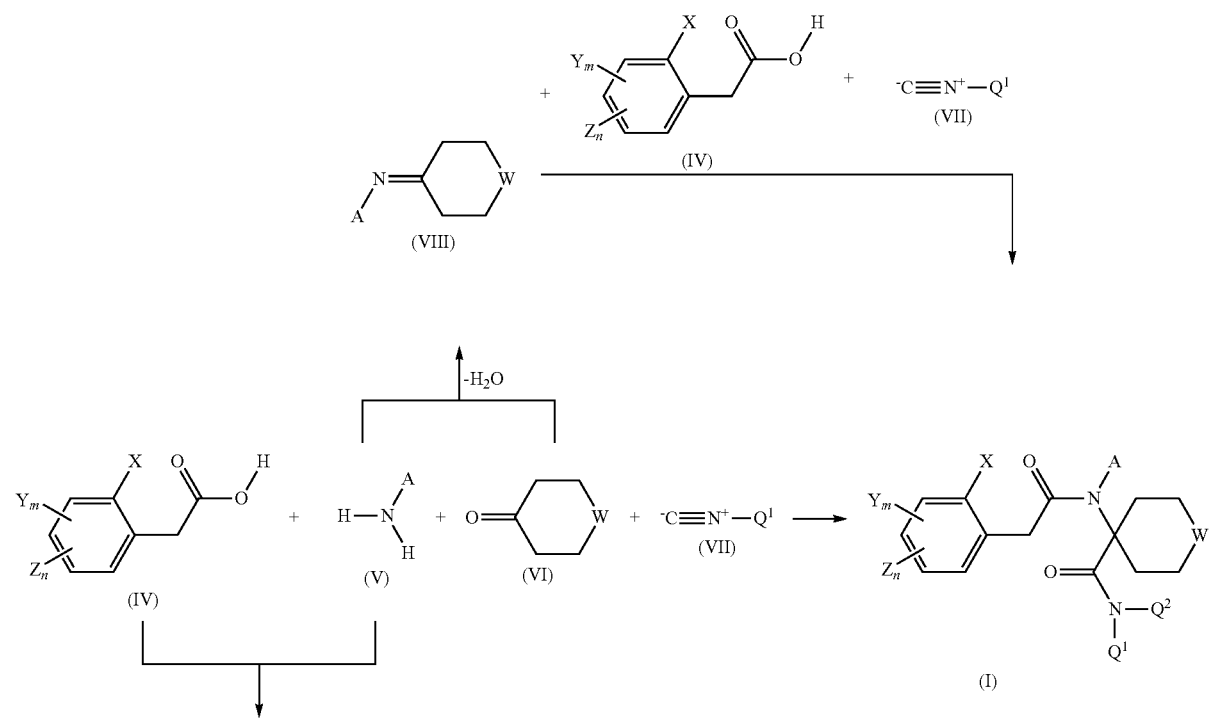

SCHEME 1

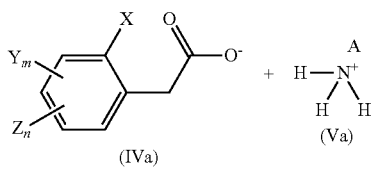 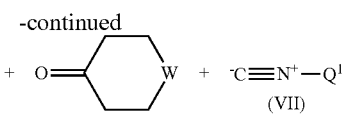 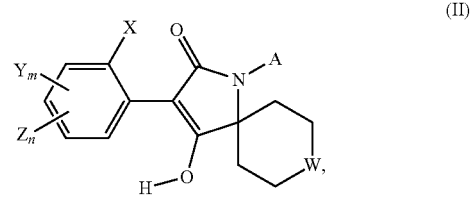

wherein $Q^2$ is hydrogen.

The Ugi multi-component reaction (Ugi-MCR) is a one-pot condensation of a carboxylic acid (IV), a primary amine (V), an oxo component (VI) and an isocyanide (VII), each of which can be introduced simultaneously or in any sequence into the reactor. The relative molar ratio of any two of (IV), (V), (VI), (VII) may range from 1:1 to 1:10, preferably between 1:1 to 1:2.

It may be sometimes advantageous to pre-form imine (VIII) by reaction of (V) and (VI) or to use suitable surrogates for (IV) and (V) such as the corresponding salts (IVa) and (Va) thereof. When A is hydrogen, the source for the reagent (V) may be ammonia ($NH_3$) or an ammonia equivalent such as for example ammonium hydroxide $NH_4OH$, ammonium chloride $NH_4Cl$, ammonium acetate $NH_4OAc$, ammonium carbonate $(NH_4)_2CO_3$, ammonium formate $HCONH_2$, and other $NH_3$ surrogates.

In most cases, it is advantageous to conduct the reaction in a suitable solvent (or diluent). It is preferred that the molar concentration of the each of the reactants in the reaction mixture is higher than 0.1M, particularly preferred are concentrations higher than 0.5M. Suitable solvents (or diluents) include polar solvents (or diluents) such as alcohols, amides, esters, ethers, nitriles and water, particularly preferred are methanol, ethanol, 2,2,2-trifluoroethanol, propanol, iso-propanol, N,N-dimethylformamide, N,N-dimethylacetamide, dioxane, tetrahydrofuran, dimethoxyethane, acetonitrile, ethyl acetate, water or mixtures thereof. The reaction temperature could be from −50° C. to 150° C., preferably between −20° C. and 100° C., most preferably between 0° C. and 60° C. The reaction time is usually between 0.1 hour and 96 hours, preferably between 1 hour and 24 hours. Various catalysts and additives may be used such as dehydrating agents ($Na_2SO_4$, $MgSO_4$, molecular sieves), water, Lewis acids ($Ti(O-i-Pr)_4$, $Sm(Otf)_3$, $Yb(Otf)_3$, $ZnCl_2$, $ZnBr_2$). The amount of a catalyst or an additive is usually between 0.01 and 1 molar equivalents.

Spiroheterocyclic pyrrolidine dione derivatives of the formula (II)

wherein X, Y, Z, m, n, A and W are as defined in the first aspect above, are useful for combating and controlling pests such as insect, acarine, mollusc and nematode pests and are disclosed for example in WO 1998/005638, WO 2004/007448, WO 2009/049851 and WO 2010/066780. Carbonate analogs of compounds of formula (II) can also be useful for combating and controlling pests such as insect, acarine, mollusc and nematode pests.

Depending on the nature of the substituents, compounds of formula II may exist in different isomeric forms. Also, compounds of formula (II) may exist in different tautomeric forms:

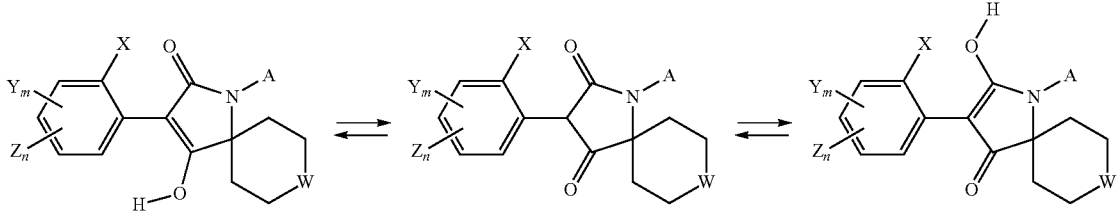

The present invention covers all isomers and tautomers and mixtures thereof in all proportions. Also, when substituents contain double bonds, cis- and trans-isomers can exist. These isomers, too, are within the scope of the claimed compounds of the formula (II).

Depending on the nature of the group W, compounds of formula (II) may exist in different cis- and trans-isomeric forms. When W is equal to $W^1$, for example, compounds of formula I may exist as trans- or cis-isomers:

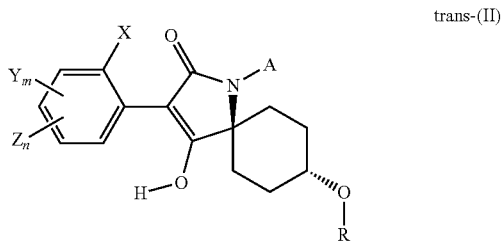

trans-(II)

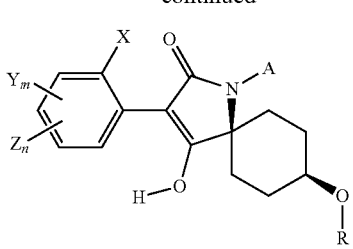

cis-(II)

The present invention covers all isomers and mixtures thereof in all proportions. Compounds of formula (I) and (II) with cis/trans isomers are those where W is selected from $W^1$, $W^4$ for p=1, $W^{10}$, $W^{11}$, $W^{12}$ and $W^{13}$.

In an embodiment, X, Y, Z, m, n, A and W for formula (II) are as those defined for formula (I) above.

In an embodiment, a compound of formula (III) and a compound of formula (I) are treated with a suitable base, in an appropriate solvent (or diluent) or solvent (or diluent) combination to produce the compound of the formula (II).

In an alternative embodiment, a compound of formula (I) is treated, in the absence of a compound of formula (III), with a suitable base, in an appropriate solvent (or diluent) or solvent (or diluent) combination to produce the compound of the formula (II).

The solvent (and if necessary the compound of formula (III)), are selected to activate the $-NQ^1Q^2$ group to become a leaving group thereby forming a compound of formula (II) through cyclisation, in which cyclisation the selected base would be mediating. Examples of suitable compounds of formula (III), bases and solvents are given below.

Examples of suitable and preferred bases, as well as examples of suitable and preferred reaction conditions (such as solvent (or diluent), solvent (or diluent) mixtures and temperature), are given below.

Preferably step (a) comprises
- a-1: reacting a compound of the formula (I) wherein $Q^2$ is hydrogen with the compound of formula (III) to produce the compound of the formula (I-I), wherein $Q^2$ is formyl, $C_{1-6}$alkylcarbonyl, or $C_{1-6}$alkoxycarbonyl; and
- a-2: ring closing the compound of the formula (I-I) wherein $Q^2$ is formyl, $C_{1-6}$alkylcarbonyl, or $C_{1-6}$alkoxycarbonyl into the compound of the formula (II).

Examples of suitable and preferred bases for steps a-1 and a-2 are given below. The base(s) for step a-1 and step a-2 may be the same or different. Examples of suitable and preferred solvents (or diluents) and solvent (or diluent) combinations for steps a-1 and a-2 are given below.

In an alternative embodiment, step (a) comprises
- a-3: reacting a compound of the formula (I) wherein $Q^2$ is hydrogen with a suitable base in the presence of suitable solvent (or diluent) under conditions which are free of the compound of formula (III) to directly produce the compound of the formula (II).

Examples of suitable and preferred bases for step a-3 are given below. Examples of such suitable and preferred solvents (or diluents) for step a-3 are given below.

In a further embodiment, step (a) comprises
- a-4: reacting a compound of the formula (I) wherein $Q^2$ is hydrogen with the compound of formula (III) and a suitable base in the presence of suitable solvent (or diluent) to directly produce the compound of the formula (II).

Examples of suitable and preferred bases for step a-4 are given below. Examples of such suitable and preferred solvents (or diluents) for step a-4 are given below.

In a further aspect the invention provides a process for the preparation of a compound of formula (I-I), wherein $Q^2$ is formyl, $C_{1-6}$alkylcarbonyl or $C_{1-6}$alkoxycarbonyl, comprising performing step a-1 as defined above.

In an embodiment, the invention provides a process for the preparation of a compound of formula (II) comprising performing step a-2 as defined above.

In an embodiment, the invention provides a process for the preparation of a compound of formula (II) comprising performing step a-3 as defined above.

In an embodiment, the invention provides a process for the preparation of a compound of formula (II) comprising performing step a-4 as defined above.

In a further aspect, the present invention provides a process for making a compound of formula (II) comprising:
1. preparing a compound of formula (I)

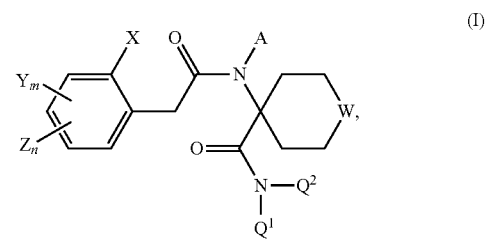

(I)

wherein X, Y, Z, m, n, A and W have the meanings given in the formula (II) above and $Q^1$ is n-butyl, s-butyl, i-butyl, tert-butyl, $C_{3-6}$cycloalkyl, $C_{1-6}$alkoxycarbonyl ($C_{1-6}$)alkyl, p-tolylsulfonylmethyl, phenyl or phenyl substituted by one or more substituent selected from the group consisting of $C_{1-4}$alkyl, $C_{1-4}$haloalkyl, $C_{1-4}$alkoxy, halogen, and nitro; and $Q^2$ is hydrogen; using the Ugi multi-component reaction (Ugi-MCR) with a carboxylic acid (IV), a primary amine (V), an oxo component (VI) and an isocyanide (VII)—as depicted in Scheme 1;
2. treating the resulting compound of the formula (I) or a salt thereof with a suitable base in an appropriate solvent (or diluent); and
3. optionally a compound of formula (III) is included in step 2 above.

The reactions described hereinabove and hereinbelow (for formula (I) and (II)) can be carried out in the absence or, normally, in the presence of a suitable solvent (or diluent) or of a mixture of these. The processes being carried out, as required, with cooling, at room temperature or with heating, for example in a temperature range of from approximately −80° C. to the boiling point of the reaction mixture, preferably from approximately −20° C. to approximately +250° C., and, if required, in a sealed vessel, under reduced, normal or elevated pressure, in an inert gas atmosphere and/or under anhydrous conditions.

The reactants for the preparation of compounds of formula (II) can be reacted as such, i. e. without addition of a solvent (or diluent), for example in the melt. In most cases, however, it is advantageous to add a solvent (or diluent) or a mixture thereof. It is preferred that the solvent (or diluent) is not water. Preferred solvents are amides, amines, ethers, nitriles, sulfoxides, or any combination thereof.

In an embodiment, it is preferred that in step (a) there is a dipolar aprotic compound to activate the $-NQ^1Q^2$ group to become a leaving group. The dipolar aprotic compound can be a solvent (or diluent) or a compound of formula (III); examples of dipolar aprotic compounds are amides, sulfoxides, or any combination thereof.

Examples of such solvents (or diluents) which may be mentioned are: aromatic, aliphatic and alicyclic hydrocarbons and halohydrocarbons or alkoxyhydrocarbons such as benzene, toluene, xylene, mesitylene, tetralin, chlorobenzene, dichlorobenzene, bromo-benzene, methoxybenzene, petroleum ether, hexane, cyclohexane, dichloromethane, trichloromethane, tetrachloromethane, dichloroethane, trichloroethene or tetrachloroethene; esters such as ethyl acetate, methlyformate, ethylformate, propylformate, butylformate, methylchloroformate, ethylchloroformate, dimethlycarbonate and diethlycarbonate; ethers such as diethyl ether, dipropyl ether, diisopropyl ether, dibutyl ether, tert-butyl methyl ether, cyclopentyl methyl ether, ethyleneglycol monomethyl ether, ethylene glycol monoethyl ether, ethylene glycol dimethyl ether, dimethoxydiethyl ether, tetrahydrofuran, anisol or dioxane; ketones, such as acetone, methyl ethyl ketone or methyl isobutyl ketone; alcohols, such as methanol, ethanol, propanol, isopropanol, butanol, ethylene glycol or glycerol; amides such as N,N-di-methylformamide, N,N-diethylformamide, N,N-dimethylacetamide, N-methylpyrrolidone or hexamethylphosphoric triamide; nitriles, such as acetonitrile, propionitrile or benzonitrile; amines, such as triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, 5-ethyl-2-methyl-pyridine, quinuclidine, N-methylmorpholine, tri-n-propylamine; and sulfoxides, such as dimethyl sulfoxide and any combination thereof.

The reaction is advantageously carried out in a temperature range from approximately −80° C. to approximately +250° C., preferably from approximately −30° C. to approximately +220° C., in many cases in the range between room temperature and approximately +200° C.

In an embodiment, $Q^3$ in formula (III) is hydrogen, chloro, $C_{1-2}$alkyl or $C_{1-2}$alkoxy.

In a further embodiment, L in formula (III) is O and $Q^4$ in formula (III) is $C_{1-4}$alkyl.

In a still further embodiment, L in formula (III) is $NC_{1-2}$alkyl and $Q^4$ in formula (III) is $C_{1-2}$alkyl.

Suitable examples of compound of formula (III) are N,N-dimethylformamide, N,N-diethylformamide, N,N-dimethylacetamide, methlyformate, ethylformate, propylformate, butylformate, methylchloroformate, ethylchloroformate, dimethlycarbonate and diethlycarbonate.

Examples of suitable bases for steps a-1, a-2, a-3 and a-4 are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium ethoxide, sodium acetate, sodium carbonate, sodium tert-butoxide, potassium hydroxide, potassium hydride, potassium amide, potassium methoxide, potassium ethoxide, potassium acetate, potassium carbonate, potassium tert-butoxide, lithium diisopropylamide, potassium bis(trimethylsilyl)amide, sodium bis (trimethylsilyl)amide, lithium bis(trimethylsilyl)amide, calcium hydride, triethylamine, diisopropylethylamine, tri-n-propylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo[5.4.0]undec-7-ene (DBU) or any mixture thereof. If the reaction is carried out in the presence of a base, bases which are employed in excess, such as triethylamine, pyridine, N-methylmorpholine or N,N-diethylaniline, may also act as solvents (or diluents).

The amount of base for steps a-1, a-2, a-3 and a-4 is generally between 0.5 and 5 equivalents, preferably the amount is between 0.75 and 3 equivalents, more preferably the amount is between 1 and 2 equivalents, based on compound of formula (I).

The amount of compound of formula (III) for step a-1 and step a-4 is generally between 1-20 equivalents, preferably the amount is between 1 and 15 equivalents, more preferably between 1.5 and 10 equivalents, based on compound of formula (I).

The concentration of (I) in the reaction mixture is generally between 1 and 75 w/w %, preferably between 5 and 50 w/w %.

In an embodiment, bases preferred for step a-1 are sodium hydride, sodium amide, sodium methoxide, sodium ethoxide, sodium tert-butoxide, potassium hydride, potassium amide, potassium methoxide, potassium ethoxide, and potassium tert-butoxide.

In an embodiment, bases preferred for step a-2 are sodium hydride, sodium amide, sodium methoxide, sodium ethoxide, sodium tert-butoxide, potassium hydride, potassium amide, potassium methoxide, potassium ethoxide, and potassium tert-butoxide.

In an embodiment, bases preferred for step a-3 are sodium hydride, sodium amide, sodium methoxide, sodium ethoxide, sodium tert-butoxide, potassium hydride, potassium amide, potassium methoxide, potassium ethoxide, and potassium tert-butoxide.

In an embodiment, bases preferred for step a-4 are sodium hydride, sodium amide, sodium methoxide, sodium ethoxide, sodium tert-butoxide, potassium hydride, potassium amide, potassium methoxide, potassium ethoxide, and potassium tert-butoxide.

Accordingly, bases preferred for step a are sodium hydride, sodium amide, sodium methoxide, sodium ethoxide, sodium tert-butoxide, potassium hydride, potassium amide, potassium methoxide, potassium ethoxide, and potassium tert-butoxide.

In an embodiment, solvent (or diluent) preferred for step a-1 are toluene, xylene, chlorobenzene, methoxybenzene, ethylene glycol dimethyl ether, dimethoxydiethyl ether, tetrahydrofuran, methanol, N,N-dimethylformamide, N,N-dimethylacetamide, N-methylpyrrolidone, tri-n-propylamine, diisopropylethylamine, dimethyl sulfoxide and any mixture thereof.

In an embodiment, solvent (or diluent) preferred for step a-2 are toluene, xylene, chlorobenzene, methoxybenzene, ethylene glycol dimethyl ether, dimethoxydiethyl ether, tetrahydrofuran, methanol, N,N-dimethylformamide, N,N-dimethylacetamide, N-methylpyrrolidone, tri-n-propylamine, diisopropylethylamine, dimethyl sulfoxide and any mixture thereof.

In an embodiment, solvent (or diluent) preferred for step a-3 are toluene, xylene, chlorobenzene, methoxybenzene, ethylene glycol dimethyl ether, dimethoxydiethyl ether, tetrahydrofuran, methanol, N,N-dimethylformamide, N,N-dimethylacetamide, N-methylpyrrolidone, tri-n-propylamine, diisopropylethylamine, dimethyl sulfoxide and any mixture thereof.

In an embodiment, solvent (or diluent) preferred for step a-4 are toluene, xylene, chlorobenzene, methoxybenzene, ethylene glycol dimethyl ether, dimethoxydiethyl ether, tetrahydrofuran, methanol, N,N-dimethylformamide, N,N-dimethylacetamide, N-methylpyrrolidone, tri-n-propylamine, diisopropylethylamine, dimethyl sulfoxide and any mixture thereof.

Accordingly, solvent (or diluent) preferred for step a are toluene, xylene, chlorobenzene, methoxybenzene, ethylene glycol dimethyl ether, dimethoxydiethyl ether, tetrahydrofuran, methanol, N,N-dimethylformamide, N,N-dimethylacetamide, N-methylpyrrolidone, tri-n-propylamine, diisopropylethylamine, dimethyl sulfoxide and any mixture thereof; more preferably N,N-di-methylformamide, N,N-dimethylacetamide, N-methylpyrrolidone, tri-n-propylamine, diisopropylethylamine, dimethyl sulfoxide and any mixture thereof.

A skilled person would realize that certain compounds of formula (III) can also be used as a solvent (or diluent) and certain bases can also be used as a solvent (or diluent).

Specific examples of compounds of formula (I) are illustrated in the Tables 1 to 300 below:

TABLE 1

This table discloses the 169 compounds T1.001 to T1.169 of the formula Ia:

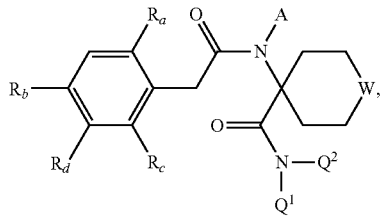

(Ia)

wherein W is $W^{14}$, A is hydrogen, $Q^1$ is n-butyl, $Q^2$ is hydrogen and $R_a$, $R_b$, $R_c$ and $R_d$ are as defined below:

| No. | $R_a$ | $R_b$ | $R_c$ | $R_d$ |
|---|---|---|---|---|
| T1.001 | Br | H | H | H |
| T1.002 | Cl | H | H | H |
| T1.003 | CH$_3$ | H | H | H |
| T1.004 | CH$_2$CH$_3$ | H | H | H |
| T1.005 | OCH$_3$ | H | H | H |
| T1.006 | Br | Cl | H | H |
| T1.007 | Cl | Br | H | H |
| T1.008 | Cl | Cl | H | H |
| T1.009 | Cl | CH$_3$ | H | H |
| T1.010 | CH$_3$ | Cl | H | H |
| T1.011 | CH$_3$ | CH$_3$ | H | H |
| T1.012 | Cl | H | Cl | H |
| T1.013 | Cl | H | CH$_3$ | H |
| T1.014 | Cl | H | CH$_2$CH$_3$ | H |
| T1.015 | Cl | H | OCH$_3$ | H |
| T1.016 | CH$_3$ | H | CH$_3$ | H |
| T1.017 | CH$_3$ | H | CH$_2$CH$_3$ | H |
| T1.018 | CH$_3$ | H | OCH$_3$ | H |
| T1.019 | CH$_2$CH$_3$ | H | CH$_2$CH$_3$ | H |
| T1.020 | CH$_2$CH$_3$ | H | OCH$_3$ | H |
| T1.021 | OCH$_3$ | H | OCH$_3$ | H |
| T1.022 | Br | H | H | Cl |
| T1.023 | Br | H | H | CH$_3$ |
| T1.024 | Br | H | H | 4-Cl—C$_6$H$_4$ |
| T1.025 | Cl | H | H | Cl |
| T1.026 | Cl | H | H | CH$_3$ |
| T1.027 | Cl | H | H | 4-Cl—C$_6$H$_4$ |

TABLE 1-continued

This table discloses the 169 compounds T1.001 to T1.169 of the formula Ia:

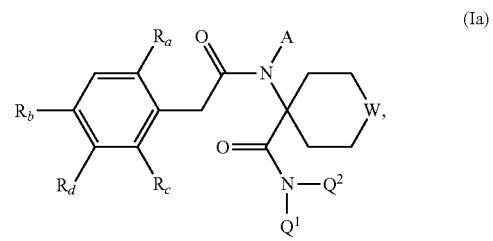

(Ia)

wherein W is $W^{14}$, A is hydrogen, $Q^1$ is n-butyl, $Q^2$ is hydrogen and $R_a$, $R_b$, $R_c$ and $R_d$ are as defined below:

| No. | $R_a$ | $R_b$ | $R_c$ | $R_d$ |
|---|---|---|---|---|
| T1.028 | CH$_3$ | H | H | Br |
| T1.029 | CH$_3$ | H | H | Cl |
| T1.030 | CH$_3$ | H | H | CH$_3$ |
| T1.031 | CH$_3$ | H | H | C$_6$H$_5$ |
| T1.032 | CH$_3$ | H | H | 4-Cl—C$_6$H$_4$ |
| T1.033 | CH$_2$CH$_3$ | H | H | CH$_3$ |
| T1.034 | CH$_2$CH$_3$ | H | H | 4-Cl—C$_6$H$_4$ |
| T1.035 | OCH$_3$ | H | H | CH$_3$ |
| T1.036 | OCH$_3$ | H | H | 4-Cl—C$_6$H$_4$ |
| T1.037 | Cl | H | Cl | Br |
| T1.038 | CH$_3$ | H | CH$_3$ | Br |
| T1.039 | CH$_3$ | H | CH$_3$ | Cl |
| T1.040 | CH$_3$ | H | CH$_3$ | 4-Cl—C$_6$H$_4$ |
| T1.041 | Br | Cl | H | CH$_3$ |
| T1.042 | Br | CH$_3$ | H | CH$_3$ |
| T1.043 | Cl | Cl | H | Cl |
| T1.044 | Cl | Br | H | CH$_3$ |
| T1.045 | Cl | Cl | H | CH$_3$ |
| T1.046 | Cl | CH$_3$ | H | Cl |
| T1.047 | Cl | CH$_3$ | H | CH$_3$ |
| T1.048 | CH$_3$ | Br | H | CH$_3$ |
| T1.049 | CH$_3$ | Cl | H | CH$_3$ |
| T1.050 | CH$_3$ | CH$_3$ | H | CH$_3$ |
| T1.051 | CH$_3$ | CH$_3$ | H | 4-Cl—C$_6$H$_4$ |
| T1.052 | Br | Br | CH$_3$ | H |
| T1.053 | Br | Cl | CH$_3$ | H |
| T1.054 | Br | CH$_3$ | Br | H |
| T1.055 | Br | CH$_3$ | Cl | H |
| T1.056 | Cl | Br | CH$_3$ | H |
| T1.057 | Cl | Cl | Cl | H |
| T1.058 | Cl | Cl | CH$_3$ | H |
| T1.059 | Cl | CH$_3$ | Cl | H |
| T1.060 | Cl | CH$_3$ | CH$_2$CH$_3$ | H |
| T1.061 | Cl | CH$_3$ | OCH$_3$ | H |
| T1.062 | Cl | 4-Cl—C$_6$H$_4$ | Cl | H |
| T1.063 | Cl | 4-Cl—C$_6$H$_4$ | CH$_3$ | H |
| T1.064 | Cl | 4-Cl—C$_6$H$_4$ | CH$_2$CH$_3$ | H |
| T1.065 | Cl | 4-Cl—C$_6$H$_4$ | OCH$_3$ | H |
| T1.066 | CH$_3$ | Br | CH$_3$ | H |
| T1.067 | CH$_3$ | Cl | CH$_3$ | H |
| T1.068 | CH$_3$ | CH$_3$ | Br | H |
| T1.069 | CH$_3$ | CH$_3$ | Cl | H |
| T1.070 | CH$_3$ | CH$_3$ | CH$_3$ | H |
| T1.071 | CH$_3$ | CH$_3$ | CH$_2$CH$_3$ | H |
| T1.072 | CH$_3$ | CH$_3$ | OCH$_3$ | H |
| T1.073 | CH$_3$ | 4-Cl—C$_6$H$_4$ | CH$_3$ | H |
| T1.074 | CH$_3$ | 4-Cl—C$_6$H$_4$ | CH$_2$CH$_3$ | H |
| T1.075 | CH$_3$ | 4-Cl—C$_6$H$_4$ | OCH$_3$ | H |
| T1.076 | CH$_2$CH$_3$ | Br | Br | H |
| T1.077 | CH$_2$CH$_3$ | Br | Cl | H |
| T1.078 | CH$_2$CH$_3$ | Br | CH$_3$ | H |
| T1.079 | CH$_2$CH$_3$ | Br | CH$_2$CH$_3$ | H |
| T1.080 | CH$_2$CH$_3$ | Br | OCH$_3$ | H |
| T1.081 | CH$_2$CH$_3$ | Cl | Br | H |
| T1.082 | CH$_2$CH$_3$ | Cl | Cl | H |
| T1.083 | CH$_2$CH$_3$ | Cl | CH$_3$ | H |
| T1.084 | CH$_2$CH$_3$ | Cl | CH$_2$CH$_3$ | H |
| T1.085 | CH$_2$CH$_3$ | Cl | OCH$_3$ | H |
| T1.086 | CH$_2$CH$_3$ | CH$_3$ | Br | H |
| T1.087 | CH$_2$CH$_3$ | CH$_3$ | Cl | H |

TABLE 1-continued

This table discloses the 169 compounds T1.001 to T1.169 of the formula Ia:

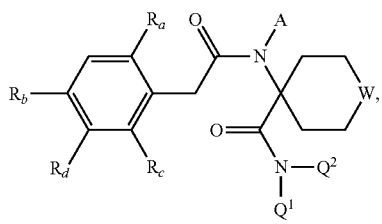

(Ia)

wherein W is $W^{14}$, A is hydrogen, $Q^1$ is n-butyl, $Q^2$ is hydrogen and $R_a$, $R_b$, $R_c$ and $R_d$ are as defined below:

| No. | $R_a$ | $R_b$ | $R_c$ | $R_d$ |
|---|---|---|---|---|
| T1.088 | $CH_2CH_3$ | $CH_3$ | $CH_2CH_3$ | H |
| T1.089 | $CH_2CH_3$ | $CH_3$ | $OCH_3$ | H |
| T1.090 | $CH_2CH_3$ | $CH_2CH_3$ | $CH_3$ | H |
| T1.091 | $CH_2CH_3$ | $CH_2CH_3$ | $CH_2CH_3$ | H |
| T1.092 | $CH_2CH_3$ | $4\text{-Cl}-C_6H_4$ | Br | H |
| T1.093 | $CH_2CH_3$ | $4\text{-Cl}-C_6H_4$ | $CH_2CH_3$ | H |
| T1.094 | $CH_2CH_3$ | $4\text{-Cl}-C_6H_4$ | $OCH_3$ | H |
| T1.095 | $OCH_3$ | Br | $CH_3$ | H |
| T1.096 | $OCH_3$ | Cl | $CH_3$ | H |
| T1.097 | $OCH_3$ | $CH_3$ | Br | H |
| T1.098 | $OCH_3$ | $CH_3$ | Cl | H |
| T1.099 | $OCH_3$ | $CH_3$ | $OCH_3$ | H |
| T1.100 | $OCH_3$ | $4\text{-Cl}-C_6H_4$ | $OCH_3$ | H |
| T1.101 | $CH_3$ | $CH_3$ | $CH_3$ | F |
| T1.102 | $CH_3$ | $CH_3$ | $CH_3$ | Cl |
| T1.103 | $CH_3$ | $CH_3$ | $CH_3$ | Br |
| T1.104 | $CH_3$ | $CH_3$ | $CH_3$ | $CH_3$ |
| T1.105 | $CH_3$ | $CH_3$ | $CH_3$ | $4\text{-Cl}-C_6H_4$ |
| T1.106 | Cl | $CH_3$ | $CH_3$ | $CH_3$ |
| T1.107 | $CH_3$ | Cl | $CH_3$ | $CH_3$ |
| T1.108 | $CH_3$ | $CH_3$ | Cl | $CH_3$ |
| T1.109 | $CH_2CH_3$ | $CH_3$ | $CH_3$ | $CH_3$ |
| T1.110 | $OCH_3$ | $CH_3$ | $CH_3$ | $CH_3$ |
| T1.111 | Cyclo-C3 | $CH_3$ | $CH_3$ | $CH_3$ |
| T1.112 | $CH_3$ | $CH_3$ | Cyclo-C3 | H |
| T1.113 | $CH_3$ | F | H | Br |
| T1.114 | $CH_3$ | $CH_3$ | H | Br |
| T1.115 | $CH_2CH_3$ | $CH_3$ | H | $CH_3$ |
| T1.116 | $OCH_3$ | $CH_3$ | H | $CH_3$ |
| T1.117 | Cyclo-C3 | $CH_3$ | H | $CH_3$ |
| T1.118 | $CH_2CH_3$ | Cl | H | $CH_3$ |
| T1.119 | $OCH_3$ | Cl | H | $CH_3$ |
| T1.120 | Cyclo-C3 | Cl | H | $CH_3$ |
| T1.121 | Cl | H | $CH_3$ | $CH_3$ |
| T1.122 | $CH_3$ | H | $CH_3$ | $CH_3$ |
| T1.123 | $CH_2CH_3$ | H | $CH_3$ | $CH_3$ |
| T1.124 | $OCH_3$ | H | $CH_3$ | $CH_3$ |
| T1.125 | Cyclo-C3 | H | $CH_3$ | $CH_3$ |
| T1.126 | F | H | Cl | $CH_3$ |
| T1.127 | Cl | H | F | $CH_3$ |
| T1.128 | H | $CH_3$ | $CH_3$ | $CH_3$ |
| T1.129 | Br | $CH_3$ | $CH_3$ | $CH_3$ |
| T1.130 | $CH_3$ | H | Cl | $CH_3$ |
| T1.131 | $CH_3$ | H | Br | $CH_3$ |
| T1.132 | Br | H | $CH_3$ | $CH_3$ |
| T1.133 | $CH_3$ | $CH=CH_2$ | $CH_3$ | H |
| T1.134 | $CH_3$ | $CH_3$ | $CH=CH_2$ | H |
| T1.135 | $CH_3$ | $C\equiv CH$ | $CH_3$ | H |
| T1.136 | $CH_3$ | $CH_3$ | $C\equiv CH$ | H |
| T1.137 | $CH_3$ | I | $CH_3$ | H |
| T1.138 | $CH_3$ | $CH_3$ | I | H |
| T1.139 | $CH_3$ | $CH_3$ | H | I |
| T1.140 | $CH_3$ | $CF_3$ | $CH_3$ | H |
| T1.141 | $CH_3$ | $CH_3$ | $CF_3$ | H |
| T1.142 | $CH_3$ | $CHF_2$ | $CH_3$ | H |
| T1.143 | $CH_3$ | $CH_3$ | $CHF_2$ | H |
| T1.144 | $CH_3$ | Cyclo-C3 | $CH_3$ | H |
| T1.145 | $CH=CH_2$ | $CH_3$ | $CH=CH_2$ | H |
| T1.146 | $C\equiv CH$ | $CH_3$ | $C\equiv CH$ | H |
| T1.147 | H | H | H | H |
| T1.148 | $CH_3CH_2$ | $C\equiv CH$ | H | H |
| T1.149 | $CH_3O$ | $C\equiv CH$ | H | H |
| T1.150 | $CH=CH_2$ | $CH_3$ | H | H |
| T1.151 | $CH=CH_2$ | $4\text{-Cl}-C_6H_4$ | H | H |
| T1.152 | $C\equiv CH$ | $CH_3$ | H | H |
| T1.153 | $C\equiv CH$ | $4\text{-Cl}-C_6H_4$ | H | H |
| T1.154 | $CH_3$ | H | $C\equiv CH$ | H |
| T1.155 | $CH_3CH_2$ | H | $C\equiv CH$ | H |
| T1.156 | $CH_3O$ | H | $C\equiv CH$ | H |
| T1.157 | $CH=CH_2$ | H | H | $4\text{-Cl}-C_6H_4$ |
| T1.158 | $C\equiv CH$ | H | H | $4\text{-Cl}-C_6H_4$ |
| T1.159 | $CH_3CH_2$ | $C\equiv CH$ | $CH_3$ | H |
| T1.160 | $CH_3O$ | $C\equiv CH$ | $CH_3$ | H |
| T1.161 | $CH=CH_2$ | $4\text{-Cl}-C_6H_4$ | $CH_3$ | H |
| T1.162 | $C\equiv CH$ | $4\text{-Cl}-C_6H_4$ | $CH_3$ | H |
| T1.163 | $CH_3CH_2$ | $CH_3$ | $C\equiv CH$ | H |
| T1.164 | $CH_3O$ | $CH_3$ | $C\equiv CH$ | H |
| T1.165 | $CH=CH_2$ | $CH_3$ | H | $4\text{-Cl}-C_6H_4$ |
| T1.166 | $C\equiv CH$ | $CH_3$ | H | $4\text{-Cl}-C_6H_4$ |
| T1.167 | $CH=CH_2$ | H | $CH_3$ | $4\text{-Cl}-C_6H_4$ |
| T1.168 | $C\equiv CH$ | H | $CH_3$ | $4\text{-Cl}-C_6H_4$ |
| T1.169 | $CH_3$ | Cl | $CH_3$ | Cl |

Note:
Cyclo-C3 means cyclopropyl.

Table 2: This table discloses the 169 compounds T2.001 to T2.169 of the formula Ia, wherein W is $W^{14}$, A is methyl, $Q^1$ is n-butyl, $Q^2$ is hydrogen and $R_a$, $R_b$, $R_c$ and $R_d$ are as defined in Table 1.

Table 3: This table discloses the 169 compounds T3.001 to T3.169 of the formula Ia, wherein W is $W^{14}$, A is $-CH_2CH=CH_2$, $Q^1$ is n-butyl, $Q^2$ is hydrogen and $R_a$, $R_b$, $R_c$ and $R_d$ are as defined in Table 1.

Table 4: This table discloses the 169 compounds T4.001 to T4.169 of the formula Ia, wherein W is $W^{14}$, A is $-CH_2C\equiv CH$, $Q^1$ is n-butyl, $Q^2$ is hydrogen and $R_a$, $R_b$, $R_c$ and $R_d$ are as defined in Table 1.

Table 5: This table discloses the 169 compounds T5.001 to T5.169 of the formula Ia, wherein W is $W^{14}$, A is phenyl, $Q^1$ is n-butyl, $Q^2$ is hydrogen and $R_a$, $R_b$, $R_c$ and $R_d$ are as defined in Table 1.

Table 6: This table discloses the 169 compounds T6.001 to T6.169 of the formula Ia, wherein W is $W^{14}$, A is hydrogen, $Q^1$ is 4-methyl-phenyl, $Q^2$ is hydrogen and $R_a$, $R_b$, $R_c$ and $R_d$ are as defined in Table 1.

Table 7: This table discloses the 169 compounds T7.001 to T7.169 of the formula Ia, wherein W is $W^{14}$, A is methyl, $Q^1$ is 4-methyl-phenyl, $Q^2$ is hydrogen and $R_a$, $R_b$, $R_c$ and $R_d$ are as defined in Table 1.

Table 8: This table discloses the 169 compounds T8.001 to T8.169 of the formula Ia, wherein W is $W^{14}$, A is $-CH_2CH=CH_2$, $Q^1$ is 4-methyl-phenyl, $Q^2$ is hydrogen and $R_a$, $R_b$, $R_c$ and $R_d$ are as defined in Table 1.

Table 9: This table discloses the 169 compounds T9.001 to T9.169 of the formula Ia, wherein W is $W^{14}$, A is —CH$_2$C≡CH, $Q^1$ is 4-methyl-phenyl, $Q^2$ is hydrogen and $R_a$, $R_b$, $R_c$ and $R_d$ are as defined in Table 1.

Table 10: This table discloses the 169 compounds T10.001 to T10.169 of the formula Ia, wherein W is $W^{14}$, A is phenyl, $Q^1$ is 4-methyl-phenyl, $Q^2$ is hydrogen and $R_a$, $R_b$, $R_c$ and $R_d$ are as defined in Table 1.

Table 11: This table discloses the 169 compounds T11.001 to T11.169 of the formula Ia, wherein W is $W^{14}$, A is hydrogen, $Q^1$ is 4-fluoro-phenyl, $Q^2$ is hydrogen and $R_a$, $R_b$, $R_c$ and $R_d$ are as defined in Table 1.

Table 12: This table discloses the 169 compounds T12.001 to T12.169 of the formula Ia, wherein W is $W^{14}$, A is methyl, $Q^1$ is 4-fluoro-phenyl, $Q^2$ is hydrogen and $R_a$, $R_b$, $R_c$ and $R_d$ are as defined in Table 1.

Table 13: This table discloses the 169 compounds T13.001 to T13.169 of the formula Ia, wherein W is $W^{14}$, A is —CH$_2$CH═CH$_2$, $Q^1$ is 4-fluoro-phenyl, $Q^2$ is hydrogen and $R_a$, $R_b$, $R_c$ and $R_d$ are as defined in Table 1.

Table 14: This table discloses the 169 compounds T14.001 to T14.169 of the formula Ia, wherein W is $W^{14}$, A is —CH$_2$C≡CH, $Q^1$ is 4-fluoro-phenyl, $Q^2$ is hydrogen and $R_a$, $R_b$, $R_c$ and $R_d$ are as defined in Table 1.

Table 15: This table discloses the 169 compounds T15.001 to T15.169 of the formula Ia, wherein W is $W^{14}$, A is phenyl, $Q^1$ is 4-fluoro-phenyl, $Q^2$ is hydrogen and $R_a$, $R_b$, $R_c$ and $R_d$ are as defined in Table 1.

Table 16: This table discloses the 169 compounds T16.001 to T16.169 of the formula Ia, wherein W is $W^{14}$, A is hydrogen, $Q^1$ is 4-methoxy-phenyl, $Q^2$ is hydrogen and $R_a$, $R_b$, $R_c$ and $R_d$ are as defined in Table 1.

Table 17: This table discloses the 169 compounds T17.001 to T17.169 of the formula Ia, wherein W is $W^{14}$, A is methyl, $Q^1$ is 4-methoxy-phenyl, $Q^2$ is hydrogen and $R_a$, $R_b$, $R_c$ and $R_d$ are as defined in Table 1.

Table 18: This table discloses the 169 compounds T18.001 to T18.169 of the formula Ia, wherein W is $W^{14}$, A is —CH$_2$CH═CH$_2$, $Q^1$ is 4-methoxy-phenyl, $Q^2$ is hydrogen and $R_a$, $R_b$, $R_c$ and $R_d$ are as defined in Table 1.

Table 19: This table discloses the 169 compounds T19.001 to T19.169 of the formula Ia, wherein W is $W^{14}$, A is —CH$_2$C≡CH, $Q^1$ is 4-methoxy-phenyl, $Q^2$ is hydrogen and $R_a$, $R_b$, $R_c$ and $R_d$ are as defined in Table 1.

Table 20: This table discloses the 169 compounds T20.001 to T20.169 of the formula Ia, wherein W is $W^{14}$, A is phenyl, $Q^1$ is 4-methoxy-phenyl, $Q^2$ is hydrogen and $R_a$, $R_b$, $R_c$ and $R_d$ are as defined in Table 1.

Table 21: This table discloses the 169 compounds T21.001 to T21.169 of the formula Ia, wherein W is $W^{14}$, A is hydrogen, $Q^1$ is 2-chloro-phenyl, $Q^2$ is hydrogen and $R_a$, $R_b$, $R_c$ and $R_d$ are as defined in Table 1.

Table 22: This table discloses the 169 compounds T22.001 to T22.169 of the formula Ia, wherein W is $W^{14}$, A is methyl, $Q^1$ is 2-chloro-phenyl, $Q^2$ is hydrogen and $R_a$, $R_b$, $R_c$ and $R_d$ are as defined in Table 1.

Table 23: This table discloses the 169 compounds T23.001 to T23.169 of the formula Ia, wherein W is $W^{14}$, A is —CH$_2$CH═CH$_2$, $Q^1$ is 2-chloro-phenyl, $Q^2$ is hydrogen and $R_a$, $R_b$, $R_c$ and $R_d$ are as defined in Table 1.

Table 24: This table discloses the 169 compounds T24.001 to T24.169 of the formula Ia, wherein W is $W^{14}$, A is —CH$_2$C≡CH, $Q^1$ is 2-chloro-phenyl, $Q^2$ is hydrogen and $R_a$, $R_b$, $R_c$ and $R_d$ are as defined in Table 1.

Table 25: This table discloses the 169 compounds T25.001 to T25.169 of the formula Ia, wherein W is $W^{14}$, A is phenyl, $Q^1$ is 2-chloro-phenyl, $Q^2$ is hydrogen and $R_a$, $R_b$, $R_c$ and $R_d$ are as defined in Table 1.

Table 26: This table discloses the 169 compounds T26.001 to T26.169 of the formula Ia, wherein W is $W^{14}$, A is hydrogen, $Q^1$ is phenyl, $Q^2$ is hydrogen and $R_a$, $R_b$, $R_c$ and $R_d$ are as defined in Table 1.

Table 27: This table discloses the 169 compounds T27.001 to T27.169 of the formula Ia, wherein W is $W^{14}$, A is methyl, $Q^1$ is phenyl, $Q^2$ is hydrogen and $R_a$, $R_b$, $R_c$ and $R_d$ are as defined in Table 1.

Table 28: This table discloses the 169 compounds T28.001 to T28.169 of the formula Ia, wherein W is $W^{14}$, A is —CH$_2$CH═CH$_2$, $Q^1$ is phenyl, $Q^2$ is hydrogen and $R_a$, $R_b$, $R_c$ and $R_d$ are as defined in Table 1.

Table 29: This table discloses the 169 compounds T29.001 to T29.169 of the formula Ia, wherein W is $W^{14}$, A is —CH$_2$C≡CH, $Q^1$ is phenyl, $Q^2$ is hydrogen and $R_a$, $R_b$, $R_c$ and $R_d$ are as defined in Table 1.

Table 30: This table discloses the 169 compounds T30.001 to T30.169 of the formula Ia, wherein W is $W^{14}$, A is phenyl, $Q^1$ is phenyl, $Q^2$ is hydrogen and $R_a$, $R_b$, $R_c$ and $R_d$ are as defined in Table 1.

Table 31: This table discloses the 169 compounds T31.001 to T31.169 of the formula Ia, wherein W is $W^{14}$, A is hydrogen, $Q^1$ is 4-nitro-phenyl, $Q^2$ is hydrogen and $R_a$, $R_b$, $R_c$ and $R_d$ are as defined in Table 1.

Table 32: This table discloses the 169 compounds T32.001 to T32.169 of the formula Ia, wherein W is $W^{14}$, A is methyl, $Q^1$ is 4-nitro-phenyl, $Q^2$ is hydrogen and $R_a$, $R_b$, $R_c$ and $R_d$ are as defined in Table 1.

Table 33: This table discloses the 169 compounds T33.001 to T33.169 of the formula Ia, wherein W is $W^{14}$, A is —CH$_2$CH═CH$_2$, $Q^1$ is 4-nitro-phenyl, $Q^2$ is hydrogen and $R_a$, $R_b$, $R_c$ and $R_d$ are as defined in Table 1.

Table 34: This table discloses the 169 compounds T34.001 to T34.169 of the formula Ia, wherein W is $W^{14}$, A is —CH$_2$C≡CH, $Q^1$ is 4-nitro-phenyl, $Q^2$ is hydrogen and $R_a$, $R_b$, $R_c$ and $R_d$ are as defined in Table 1.

Table 35: This table discloses the 169 compounds T35.001 to T35.169 of the formula Ia, wherein W is $W^{14}$, A is phenyl, $Q^1$ is 4-nitro-phenyl, $Q^2$ is hydrogen and $R_a$, $R_b$, $R_c$ and $R_d$ are as defined in Table 1.

Table 36: This table discloses the 169 compounds T36.001 to T36.169 of the formula Ia, wherein W is $W^{14}$, A is hydrogen, $Q^1$ is 2,6-dimethyl-phenyl, $Q^2$ is hydrogen and $R_a$, $R_b$, $R_c$ and $R_d$ are as defined in Table 1.

Table 37: This table discloses the 169 compounds T37.001 to T37.169 of the formula Ia, wherein W is $W^{14}$, A is methyl, $Q^1$ is 2,6-dimethyl-phenyl, $Q^2$ is hydrogen and $R_a$, $R_b$, $R_c$ and $R_d$ are as defined in Table 1.

Table 38: This table discloses the 169 compounds T38.001 to T38.169 of the formula Ia, wherein W is $W^{14}$, A is —CH$_2$CH═CH$_2$, $Q^1$ is 2,6-dimethyl-phenyl, $Q^2$ is hydrogen and $R_a$, $R_b$, $R_c$ and $R_d$ are as defined in Table 1.

Table 39: This table discloses the 169 compounds T39.001 to T39.169 of the formula Ia, wherein W is $W^{14}$, A is —CH$_2$C≡CH, $Q^1$ is 2,6-dimethyl-phenyl, $Q^2$ is hydrogen and $R_a$, $R_b$, $R_c$ and $R_d$ are as defined in Table 1.

Table 40: This table discloses the 169 compounds T40.001 to T40.169 of the formula Ia, wherein W is $W^{14}$, A is phenyl, $Q^1$ is 2,6-dimethyl-phenyl, $Q^2$ is hydrogen and $R_a$, $R_b$, $R_c$ and $R_d$ are as defined in Table 1.

Table 41: This table discloses the 169 compounds T41.001 to T41.169 of the formula Ia, wherein W is $W^{14}$, A is hydrogen, $Q^1$ is 2-methoxy-4-nitro-phenyl, $Q^2$ is hydrogen and $R_a$, $R_b$, $R_c$ and $R_d$ are as defined in Table 1.
Table 42: This table discloses the 169 compounds T42.001 to T42.169 of the formula Ia, wherein W is $W^{14}$, A is methyl, $Q^1$ is 2-methoxy-4-nitro-phenyl, $Q^2$ is hydrogen and $R_a$, $R_b$, $R_c$ and $R_d$ are as defined in Table 1.
Table 43: This table discloses the 169 compounds T43.001 to T43.169 of the formula Ia, wherein W is $W^{14}$, A is —$CH_2CH=CH_2$, $Q^1$ is 2-methoxy-4-nitro-phenyl, $Q^2$ is hydrogen and $R_a$, $R_b$, $R_c$ and $R_d$ are as defined in Table 1.
Table 44: This table discloses the 169 compounds T44.001 to T44.169 of the formula Ia, wherein W is $W^{14}$, A is —$CH_2C\equiv CH$, $Q^1$ is 2-methoxy-4-nitro-phenyl, $Q^2$ is hydrogen and $R_a$, $R_b$, $R_c$ and $R_d$ are as defined in Table 1.
Table 45: This table discloses the 169 compounds T45.001 to T45.169 of the formula Ia, wherein W is $W^{14}$, A is phenyl, $Q^1$ is 2-methoxy-4-nitro-phenyl, $Q^2$ is hydrogen and $R_a$, $R_b$, $R_c$ and $R_d$ are as defined in Table 1.
Table 46: This table discloses the 169 compounds T46.001 to T46.169 of the formula Ia, wherein W is $W^{13}$, R is hydrogen, A is hydrogen, $Q^1$ is n-butyl, $Q^2$ is hydrogen and $R_a$, $R_b$, $R_c$ and $R_d$ are as defined in Table 1.
Table 47: This table discloses the 169 compounds T47.001 to T47.169 of the formula Ia, wherein W is $W^{13}$, R is hydrogen, A is methyl, $Q^1$ is n-butyl, $Q^2$ is hydrogen and $R_a$, $R_b$, $R_c$ and $R_d$ are as defined in Table 1.
Table 48: This table discloses the 169 compounds T48.001 to T48.169 of the formula Ia, wherein W is $W^{13}$, R is hydrogen, A is —$CH_2CH=CH_2$, $Q^1$ is n-butyl, $Q^2$ is hydrogen and $R_a$, $R_b$, $R_c$ and $R_d$ are as defined in Table 1.
Table 49: This table discloses the 169 compounds T49.001 to T49.169 of the formula Ia, wherein W is $W^{13}$, R is hydrogen, A is —$CH_2C\equiv CH$, $Q^1$ is n-butyl, $Q^2$ is hydrogen and $R_a$, $R_b$, $R_c$ and $R_d$ are as defined in Table 1.
Table 50: This table discloses the 169 compounds T50.001 to T50.169 of the formula Ia, wherein W is $W^{13}$, R is hydrogen, A is phenyl, $Q^1$ is n-butyl, $Q^2$ is hydrogen and $R_a$, $R_b$, $R_c$ and $R_d$ are as defined in Table 1.
Table 51: This table discloses the 169 compounds T51.001 to T51.169 of the formula Ia, wherein W is $W^{13}$, R is hydrogen, A is hydrogen, $Q^1$ is 4-methyl-phenyl, $Q^2$ is hydrogen and $R_a$, $R_b$, $R_c$ and $R_d$ are as defined in Table 1.
Table 52: This table discloses the 169 compounds T52.001 to T52.169 of the formula Ia, wherein W is $W^{13}$, R is hydrogen, A is methyl, $Q^1$ is 4-methyl-phenyl, $Q^2$ is hydrogen and $R_a$, $R_b$, $R_c$ and $R_d$ are as defined in Table 1.
Table 53: This table discloses the 169 compounds T53.001 to T53.169 of the formula Ia, wherein W is $W^{13}$, R is hydrogen, A is —$CH_2CH=CH_2$, $Q^1$ is 4-methyl-phenyl, $Q^2$ is hydrogen and $R_a$, $R_b$, $R_c$ and $R_d$ are as defined in Table 1.
Table 54: This table discloses the 169 compounds T54.001 to T54.169 of the formula Ia, wherein W is $W^{13}$, R is hydrogen, A is —$CH_2C\equiv CH$, $Q^1$ is 4-methyl-phenyl, $Q^2$ is hydrogen and $R_a$, $R_b$, $R_c$ and $R_d$ are as defined in Table 1.
Table 55: This table discloses the 169 compounds T55.001 to T55.169 of the formula Ia, wherein W is $W^{13}$, R is hydrogen, A is phenyl, $Q^1$ is 4-methyl-phenyl, $Q^2$ is hydrogen and $R_a$, $R_b$, $R_c$ and $R_d$ are as defined in Table 1.
Table 56: This table discloses the 169 compounds T56.001 to T56.169 of the formula Ia, wherein W is $W^{13}$, R is hydrogen, A is hydrogen, $Q^1$ is 4-fluoro-phenyl, $Q^2$ is hydrogen and $R_a$, $R_b$, $R_c$ and $R_d$ are as defined in Table 1.
Table 57: This table discloses the 169 compounds T57.001 to T57.169 of the formula Ia, wherein W is $W^{13}$, R is hydrogen, A is methyl, $Q^1$ is 4-fluoro-phenyl, $Q^2$ is hydrogen and $R_a$, $R_b$, $R_c$ and $R_d$ are as defined in Table 1.
Table 58: This table discloses the 169 compounds T58.001 to T58.169 of the formula Ia, wherein W is $W^{13}$, R is hydrogen, A is —$CH_2CH=CH_2$, $Q^1$ is 4-fluoro-phenyl, $Q^2$ is hydrogen and $R_a$, $R_b$, $R_c$ and $R_d$ are as defined in Table 1.
Table 59: This table discloses the 169 compounds T59.001 to T59.169 of the formula Ia, wherein W is $W^{13}$, R is hydrogen, A is —$CH_2C\equiv CH$, $Q^1$ is 4-fluoro-phenyl, $Q^2$ is hydrogen and $R_a$, $R_b$, $R_c$ and $R_d$ are as defined in Table 1.
Table 60: This table discloses the 169 compounds T60.001 to T60.169 of the formula Ia, wherein W is $W^{13}$, R is hydrogen, A is phenyl, $Q^1$ is 4-fluoro-phenyl, $Q^2$ is hydrogen and $R_a$, $R_b$, $R_c$ and $R_d$ are as defined in Table 1.
Table 61: This table discloses the 169 compounds T61.001 to T61.169 of the formula Ia, wherein W is $W^{13}$, R is hydrogen, A is hydrogen, $Q^1$ is 4-methoxy-phenyl, $Q^2$ is hydrogen and $R_a$, $R_b$, $R_c$ and $R_d$ are as defined in Table 1.
Table 62: This table discloses the 169 compounds T62.001 to T62.169 of the formula Ia, wherein W is $W^{13}$, R is hydrogen, A is methyl, $Q^1$ is 4-methoxy-phenyl, $Q^2$ is hydrogen and $R_a$, $R_b$, $R_c$ and $R_d$ are as defined in Table 1.
Table 63: This table discloses the 169 compounds T63.001 to T63.169 of the formula Ia, wherein W is $W^{13}$, R is hydrogen, A is —$CH_2CH=CH_2$, $Q^1$ is 4-methoxy-phenyl, $Q^2$ is hydrogen and $R_a$, $R_b$, $R_c$ and $R_d$ are as defined in Table 1.
Table 64: This table discloses the 169 compounds T64.001 to T64.169 of the formula Ia, wherein W is $W^{13}$, R is hydrogen, A is —$CH_2C\equiv CH$, $Q^1$ is 4-methoxy-phenyl, $Q^2$ is hydrogen and $R_a$, $R_b$, $R_c$ and $R_d$ are as defined in Table 1.
Table 65: This table discloses the 169 compounds T65.001 to T65.169 of the formula Ia, wherein W is $W^{13}$, R is hydrogen, A is phenyl, $Q^1$ is 4-methoxy-phenyl, $Q^2$ is hydrogen and $R_a$, $R_b$, $R_c$ and $R_d$ are as defined in Table 1.
Table 66: This table discloses the 169 compounds T66.001 to T66.169 of the formula Ia, wherein W is $W^{13}$, R is hydrogen, A is hydrogen, $Q^1$ is 2-chloro-phenyl, $Q^2$ is hydrogen and $R_a$, $R_b$, $R_c$ and $R_d$ are as defined in Table 1.
Table 67: This table discloses the 169 compounds T67.001 to T67.169 of the formula Ia, wherein W is $W^{13}$, R is hydrogen, A is methyl, $Q^1$ is 2-chloro-phenyl, $Q^2$ is hydrogen and $R_a$, $R_b$, $R_c$ and $R_d$ are as defined in Table 1.
Table 68: This table discloses the 169 compounds T68.001 to T68.169 of the formula Ia, wherein W is $W^{13}$, R is hydrogen, A is —$CH_2CH=CH_2$, $Q^1$ is 2-chloro-phenyl, $Q^2$ is hydrogen and $R_a$, $R_b$, $R_c$ and $R_d$ are as defined in Table 1.
Table 69: This table discloses the 169 compounds T69.001 to T69.169 of the formula Ia, wherein W is $W^{13}$, R is hydrogen, A is —$CH_2C\equiv CH$, $Q^1$ is 2-chloro-phenyl, $Q^2$ is hydrogen and $R_a$, $R_b$, $R_c$ and $R_d$ are as defined in Table 1.
Table 70: This table discloses the 169 compounds T70.001 to T70.169 of the formula Ia, wherein W is $W^{13}$, R is hydrogen, A is phenyl, $Q^1$ is 2-chloro-phenyl, $Q^2$ is hydrogen and $R_a$, $R_b$, $R_c$ and $R_d$ are as defined in Table 1.
Table 71: This table discloses the 169 compounds T71.001 to T71.169 of the formula Ia, wherein W is $W^{13}$, R is hydrogen, A is hydrogen, $Q^1$ is phenyl, $Q^2$ is hydrogen and $R_a$, $R_b$, $R_c$ and $R_d$ are as defined in Table 1.
Table 72: This table discloses the 169 compounds T72.001 to T72.169 of the formula Ia, wherein W is $W^{13}$, R is hydrogen, A is methyl, $Q^1$ is phenyl, $Q^2$ is hydrogen and $R_a$, $R_b$, $R_c$ and $R_d$ are as defined in Table 1.
Table 73: This table discloses the 169 compounds T73.001 to T73.169 of the formula Ia, wherein W is $W^{13}$, R is hydrogen, A is —$CH_2CH=CH_2$, $Q^1$ is phenyl, $Q^2$ is hydrogen and $R_a$, $R_b$, $R_c$ and $R_d$ are as defined in Table 1.
Table 74: This table discloses the 169 compounds T74.001 to T74.169 of the formula Ia, wherein W is $W^{13}$, R is hydrogen, A is —CH$_2$C≡CH, Q$^1$ is phenyl, Q$^2$ is hydrogen and R$_a$, R$_b$, R$_c$ and R$_d$ are as defined in Table 1.
Table 75: This table discloses the 169 compounds T75.001 to T75.169 of the formula Ia, wherein W is W$^{13}$, R is hydrogen, A is phenyl, Q$^1$ is phenyl, Q$^2$ is hydrogen and R$_a$, R$_b$, R$_c$ and R$_d$ are as defined in Table 1.
Table 76: This table discloses the 169 compounds T76.001 to T76.169 of the formula Ia, wherein W is W$^{13}$, R is hydrogen, A is hydrogen, Q$^1$ is 4-nitro-phenyl, Q$^2$ is hydrogen and R$_a$, R$_b$, R$_c$ and R$_d$ are as defined in Table 1.
Table 77: This table discloses the 169 compounds T77.001 to T77.169 of the formula Ia, wherein W is W$^{13}$, R is hydrogen, A is methyl, Q$^1$ is 4-nitro-phenyl, Q$^2$ is hydrogen and R$_a$, R$_b$, R$_c$ and R$_d$ are as defined in Table 1.
Table 78: This table discloses the 169 compounds T78.001 to T78.169 of the formula Ia, wherein W is W$^{13}$, R is hydrogen, A is —CH$_2$CH=CH$_2$, Q$^1$ is 4-nitro-phenyl, Q$^2$ is hydrogen and R$_a$, R$_b$, R$_c$ and R$_d$ are as defined in Table 1.
Table 79: This table discloses the 169 compounds T79.001 to T79.169 of the formula Ia, wherein W is W$^{13}$, R is hydrogen, A is —CH$_2$C≡CH, Q$^1$ is 4-nitro-phenyl, Q$^2$ is hydrogen and R$_a$, R$_b$, R$_c$ and R$_d$ are as defined in Table 1.
Table 80: This table discloses the 169 compounds T80.001 to T80.169 of the formula Ia, wherein W is W$^{13}$, R is hydrogen, A is phenyl, Q$^1$ is 4-nitro-phenyl, Q$^2$ is hydrogen and R$_a$, R$_b$, R$_c$ and R$_d$ are as defined in Table 1.
Table 81: This table discloses the 169 compounds T81.001 to T81.169 of the formula Ia, wherein W is W$^{13}$, R is hydrogen, A is hydrogen, Q$^1$ is 2,6-dimethyl-phenyl, Q$^2$ is hydrogen and R$_a$, R$_b$, R$_c$ and R$_d$ are as defined in Table 1.
Table 82: This table discloses the 169 compounds T82.001 to T82.169 of the formula Ia, wherein W is W$^{13}$, R is hydrogen, A is methyl, Q$^1$ is 2,6-dimethyl-phenyl, Q$^2$ is hydrogen and R$_a$, R$_b$, R$_c$ and R$_d$ are as defined in Table 1.
Table 83: This table discloses the 169 compounds T83.001 to T83.169 of the formula Ia, wherein W is W$^{13}$, R is hydrogen, A is —CH$_2$CH=CH$_2$, Q$^1$ is 2,6-dimethyl-phenyl, Q$^2$ is hydrogen and R$_a$, R$_b$, R$_c$ and R$_d$ are as defined in Table 1.
Table 84: This table discloses the 169 compounds T84.001 to T84.169 of the formula Ia, wherein W is W$^{13}$, R is hydrogen, A is —CH$_2$C≡CH, Q$^1$ is 2,6-dimethyl-phenyl, Q$^2$ is hydrogen and R$_a$, R$_b$, R$_c$ and R$_d$ are as defined in Table 1.
Table 85: This table discloses the 169 compounds T85.001 to T85.169 of the formula Ia, wherein W is W$^{13}$, R is hydrogen, A is phenyl, Q$^1$ is 2,6-dimethyl-phenyl, Q$^2$ is hydrogen and R$_a$, R$_b$, R$_c$ and R$_d$ are as defined in Table 1.
Table 86: This table discloses the 169 compounds T86.001 to T86.169 of the formula Ia, wherein W is W$^{13}$, R is hydrogen, A is hydrogen, Q$^1$ is 2-methoxy-4-nitro-phenyl, Q$^2$ is hydrogen and R$_a$, R$_b$, R$_c$ and R$_d$ are as defined in Table 1.
Table 87: This table discloses the 169 compounds T87.001 to T87.169 of the formula Ia, wherein W is W$^{13}$, R is hydrogen, A is methyl, Q$^1$ is 2-methoxy-4-nitro-phenyl, Q$^2$ is hydrogen and R$_a$, R$_b$, R$_c$ and R$_d$ are as defined in Table 1.
Table 88: This table discloses the 169 compounds T88.001 to T88.169 of the formula Ia, wherein W is W$^{13}$, R is hydrogen, A is —CH$_2$CH=CH$_2$, Q$^1$ is 2-methoxy-4-nitro-phenyl, Q$^2$ is hydrogen and R$_a$, R$_b$, R$_c$ and R$_d$ are as defined in Table 1.
Table 89: This table discloses the 169 compounds T89.001 to T89.169 of the formula Ia, wherein W is W$^{13}$, R is hydrogen, A is —CH$_2$C≡CH, Q$^1$ is 2-methoxy-4-nitro-phenyl, Q$^2$ is hydrogen and R$_a$, R$_b$, R$_c$ and R$_d$ are as defined in Table 1.
Table 90: This table discloses the 169 compounds T90.001 to T90.169 of the formula Ia, wherein W is W$^{13}$, R is hydrogen, A is phenyl, Q$^1$ is 2-methoxy-4-nitro-phenyl, Q$^2$ is hydrogen and R$_a$, R$_b$, R$_c$ and R$_d$ are as defined in Table 1.
Table 91: This table discloses the 169 compounds T91.001 to T91.169 of the formula Ia, wherein W is W$^1$, R is methyl, A is hydrogen, Q$^1$ is n-butyl, Q$^2$ is hydrogen and R$_a$, R$_b$, R$_c$ and R$_d$ are as defined in Table 1.
Table 92: This table discloses the 169 compounds T92.001 to T92.169 of the formula Ia, wherein W is W$^1$, R is methyl, A is methyl, Q$^1$ is n-butyl, Q$^2$ is hydrogen and R$_a$, R$_b$, R$_c$ and R$_d$ are as defined in Table 1.
Table 93: This table discloses the 169 compounds T93.001 to T93.169 of the formula Ia, wherein W is W$^1$, R is methyl, A is —CH$_2$CH=CH$_2$, Q$^1$ is n-butyl, Q$^2$ is hydrogen and R$_a$, R$_b$, R$_c$ and R$_d$ are as defined in Table 1.
Table 94: This table discloses the 169 compounds T94.001 to T94.169 of the formula Ia, wherein W is W$^1$, R is methyl, A is —CH$_2$C≡CH, Q$^1$ is n-butyl, Q$^2$ is hydrogen and R$_a$, R$_b$, R$_c$ and R$_d$ are as defined in Table 1.
Table 95: This table discloses the 169 compounds T95.001 to T95.169 of the formula Ia, wherein W is W$^1$, R is methyl, A is phenyl, Q$^1$ is n-butyl, Q$^2$ is hydrogen and R$_a$, R$_b$, R$_c$ and R$_d$ are as defined in Table 1.
Table 96: This table discloses the 169 compounds T96.001 to T96.169 of the formula Ia, wherein W is W$^1$, R is methyl, A is hydrogen, Q$^1$ is 4-methyl-phenyl, Q$^2$ is hydrogen and R$_a$, R$_b$, R$_c$ and R$_d$ are as defined in Table 1.
Table 97: This table discloses the 169 compounds T97.001 to T97.169 of the formula Ia, wherein W is W$^1$, R is methyl, A is methyl, Q$^1$ is 4-methyl-phenyl, Q$^2$ is hydrogen and R$_a$, R$_b$, R$_c$ and R$_d$ are as defined in Table 1.
Table 98: This table discloses the 169 compounds T98.001 to T98.169 of the formula Ia, wherein W is W$^1$, R is methyl, A is —CH$_2$CH=CH$_2$, Q$^1$ is 4-methyl-phenyl, Q$^2$ is hydrogen and R$_a$, R$_b$, R$_c$ and R$_d$ are as defined in Table 1.
Table 99: This table discloses the 169 compounds T99.001 to T99.169 of the formula Ia, wherein W is W$^1$, R is methyl, A is —CH$_2$C≡CH, Q$^1$ is 4-methyl-phenyl, Q$^2$ is hydrogen and R$_a$, R$_b$, R$_c$ and R$_d$ are as defined in Table 1.
Table 100: This table discloses the 169 compounds T100.001 to T100.169 of the formula Ia, wherein W is W$^1$, R is methyl, A is phenyl, Q$^1$ is 4-methyl-phenyl, Q$^2$ is hydrogen and R$_a$, R$_b$, R$_c$ and R$_d$ are as defined in Table 1.
Table 101: This table discloses the 169 compounds T101.001 to T101.169 of the formula Ia, wherein W is W$^1$, R is methyl, A is hydrogen, Q$^1$ is 4-fluoro-phenyl, Q$^2$ is hydrogen and R$_a$, R$_b$, R$_c$ and R$_d$ are as defined in Table 1.
Table 102: This table discloses the 169 compounds T102.001 to T102.169 of the formula Ia, wherein W is W$^1$, R is methyl, A is methyl, Q$^1$ is 4-fluoro-phenyl, Q$^2$ is hydrogen and R$_a$, R$_b$, R$_c$ and R$_d$ are as defined in Table 1.
Table 103: This table discloses the 169 compounds T103.001 to T103.169 of the formula Ia, wherein W is W$^1$, R is methyl, A is —CH$_2$CH=CH$_2$, Q$^1$ is 4-fluoro-phenyl, Q$^2$ is hydrogen and R$_a$, R$_b$, R$_c$ and R$_d$ are as defined in Table 1.
Table 104: This table discloses the 169 compounds T104.001 to T104.169 of the formula Ia, wherein W is W$^1$, R is methyl, A is —CH$_2$C≡CH, Q$^1$ is 4-fluoro-phenyl, Q$^2$ is hydrogen and R$_a$, R$_b$, R$_c$ and R$_d$ are as defined in Table 1.
Table 105: This table discloses the 169 compounds T105.001 to T105.169 of the formula Ia, wherein W is W$^1$, R is methyl, A is phenyl, Q$^1$ is 4-fluoro-phenyl, Q$^2$ is hydrogen and R$_a$, R$_b$, R$_c$ and R$_d$ are as defined in Table 1.
Table 106: This table discloses the 169 compounds T106.001 to T106.169 of the formula Ia, wherein W is W$^1$, R is methyl, A is hydrogen, $Q^1$ is 4-methoxy-phenyl, $Q^2$ is hydrogen and $R_a$, $R_b$, $R_c$ and $R_d$ are as defined in Table 1.

Table 107: This table discloses the 169 compounds T107.001 to T107.169 of the formula Ia, wherein W is $W^1$, R is methyl, A is methyl, $Q^1$ is 4-methoxy-phenyl, $Q^2$ is hydrogen and $R_a$, $R_b$, $R_c$ and $R_d$ are as defined in Table 1.

Table 108: This table discloses the 169 compounds T108.001 to T108.169 of the formula Ia, wherein W is $W^1$, R is methyl, A is —CH$_2$CH=CH$_2$, $Q^1$ is 4-methoxy-phenyl, $Q^2$ is hydrogen and $R_a$, $R_b$, $R_c$ and $R_d$ are as defined in Table 1.

Table 109: This table discloses the 169 compounds T109.001 to T109.169 of the formula Ia, wherein W is $W^1$, R is methyl, A is —CH$_2$C≡CH, $Q^1$ is 4-methoxy-phenyl, $Q^2$ is hydrogen and $R_a$, $R_b$, $R_c$ and $R_d$ are as defined in Table 1.

Table 110: This table discloses the 169 compounds T110.001 to T110.169 of the formula Ia, wherein W is $W^1$, R is methyl, A is phenyl, $Q^1$ is 4-methoxy-phenyl, $Q^2$ is hydrogen and $R_a$, $R_b$, $R_c$ and $R_d$ are as defined in Table 1.

Table 111: This table discloses the 169 compounds T111.001 to T111.169 of the formula Ia, wherein W is $W^1$, R is methyl, A is hydrogen, $Q^1$ is 2-chloro-phenyl, $Q^2$ is hydrogen and $R_a$, $R_b$, $R_c$ and $R_d$ are as defined in Table 1.

Table 112: This table discloses the 169 compounds T112.001 to T112.169 of the formula Ia, wherein W is $W^1$, R is methyl, A is methyl, $Q^1$ is 2-chloro-phenyl, $Q^2$ is hydrogen and $R_a$, $R_b$, $R_c$ and $R_d$ are as defined in Table 1.

Table 113: This table discloses the 169 compounds T113.001 to T113.169 of the formula Ia, wherein W is $W^1$, R is methyl, A is —CH$_2$CH=CH$_2$, $Q^1$ is 2-chloro-phenyl, $Q^2$ is hydrogen and $R_a$, $R_b$, $R_c$ and $R_d$ are as defined in Table 1.

Table 114: This table discloses the 169 compounds T114.001 to T114.169 of the formula Ia, wherein W is $W^1$, R is methyl, A is —CH$_2$C≡CH, $Q^1$ is 2-chloro-phenyl, $Q^2$ is hydrogen and $R_a$, $R_b$, $R_c$ and $R_d$ are as defined in Table 1.

Table 115: This table discloses the 169 compounds T115.001 to T115.169 of the formula Ia, wherein W is $W^1$, R is methyl, A is phenyl, $Q^1$ is 2-chloro-phenyl, $Q^2$ is hydrogen and $R_a$, $R_b$, $R_c$ and $R_d$ are as defined in Table 1.

Table 116: This table discloses the 169 compounds T116.001 to T116.169 of the formula Ia, wherein W is $W^1$, R is methyl, A is hydrogen, $Q^1$ is phenyl, $Q^2$ is hydrogen and $R_a$, $R_b$, $R_c$ and $R_d$ are as defined in Table 1.

Table 117: This table discloses the 169 compounds T117.001 to T117.169 of the formula Ia, wherein W is $W^1$, R is methyl, A is methyl, $Q^1$ is phenyl, $Q^2$ is hydrogen and $R_a$, $R_b$, $R_c$ and $R_d$ are as defined in Table 1.

Table 118: This table discloses the 169 compounds T118.001 to T118.169 of the formula Ia, wherein W is $W^1$, R is methyl, A is —CH$_2$CH=CH$_2$, $Q^1$ is phenyl, $Q^2$ is hydrogen and $R_a$, $R_b$, $R_c$ and $R_d$ are as defined in Table 1.

Table 119: This table discloses the 169 compounds T119.001 to T119.169 of the formula Ia, wherein W is $W^1$, R is methyl, A is —CH$_2$C≡CH, $Q^1$ is phenyl, $Q^2$ is hydrogen and $R_a$, $R_b$, $R_c$ and $R_d$ are as defined in Table 1.

Table 120: This table discloses the 169 compounds T120.001 to T120.169 of the formula Ia, wherein W is $W^1$, R is methyl, A is phenyl, $Q^1$ is phenyl, $Q^2$ is hydrogen and $R_a$, $R_b$, $R_c$ and $R_d$ are as defined in Table 1.

Table 121: This table discloses the 169 compounds T121.001 to T121.169 of the formula Ia, wherein W is $W^1$, R is methyl, A is hydrogen, $Q^1$ is 4-nitro-phenyl, $Q^2$ is hydrogen and $R_a$, $R_b$, $R_c$ and $R_d$ are as defined in Table 1.

Table 122: This table discloses the 169 compounds T122.001 to T122.169 of the formula Ia, wherein W is $W^1$, R is methyl, A is methyl, $Q^1$ is 4-nitro-phenyl, $Q^2$ is hydrogen and $R_a$, $R_b$, $R_c$ and $R_d$ are as defined in Table 1.

Table 123: This table discloses the 169 compounds T123.001 to T123.169 of the formula Ia, wherein W is $W^1$, R is methyl, A is —CH$_2$CH=CH$_2$, $Q^1$ is 4-nitro-phenyl, $Q^2$ is hydrogen and $R_a$, $R_b$, $R_c$ and $R_d$ are as defined in Table 1.

Table 124: This table discloses the 169 compounds T124.001 to T124.169 of the formula Ia, wherein W is $W^1$, R is methyl, A is —CH$_2$C≡CH, $Q^1$ is 4-nitro-phenyl, $Q^2$ is hydrogen and $R_a$, $R_b$, $R_c$ and $R_d$ are as defined in Table 1.

Table 125: This table discloses the 169 compounds T125.001 to T125.169 of the formula Ia, wherein W is $W^1$, R is methyl, A is phenyl, $Q^1$ is 4-nitro-phenyl, $Q^2$ is hydrogen and $R_a$, $R_b$, $R_c$ and $R_d$ are as defined in Table 1.

Table 126: This table discloses the 169 compounds T126.001 to T126.169 of the formula Ia, wherein W is $W^1$, R is methyl, A is hydrogen, $Q^1$ is 2,6-dimethyl-phenyl, $Q^2$ is hydrogen and $R_a$, $R_b$, $R_c$ and $R_d$ are as defined in Table 1.

Table 127: This table discloses the 169 compounds T127.001 to T127.169 of the formula Ia, wherein W is $W^1$, R is methyl, A is methyl, $Q^1$ is 2,6-dimethyl-phenyl, $Q^2$ is hydrogen and $R_a$, $R_b$, $R_c$ and $R_d$ are as defined in Table 1.

Table 128: This table discloses the 169 compounds T128.001 to T128.169 of the formula Ia, wherein W is $W^1$, R is methyl, A is —CH$_2$CH=CH$_2$, $Q^1$ is 2,6-dimethyl-phenyl, $Q^2$ is hydrogen and $R_a$, $R_b$, $R_c$ and $R_d$ are as defined in Table 1.

Table 129: This table discloses the 169 compounds T129.001 to T129.169 of the formula Ia, wherein W is $W^1$, R is methyl, A is —CH$_2$C≡CH, $Q^1$ is 2,6-dimethyl-phenyl, $Q^2$ is hydrogen and $R_a$, $R_b$, $R_c$ and $R_d$ are as defined in Table 1.

Table 130: This table discloses the 169 compounds T130.001 to T130.169 of the formula Ia, wherein W is $W^1$, R is methyl, A is phenyl, $Q^1$ is 2,6-dimethyl-phenyl, $Q^2$ is hydrogen and $R_a$, $R_b$, $R_c$ and $R_d$ are as defined in Table 1.

Table 131: This table discloses the 169 compounds T131.001 to T131.169 of the formula Ia, wherein W is $W^1$, R is methyl, A is hydrogen, $Q^1$ is 2-methoxy-4-nitro-phenyl, $Q^2$ is hydrogen and $R_a$, $R_b$, $R_c$ and $R_d$ are as defined in Table 1.

Table 132: This table discloses the 169 compounds T132.001 to T132.169 of the formula Ia, wherein W is $W^1$, R is methyl, A is methyl, $Q^1$ is 2-methoxy-4-nitro-phenyl, $Q^2$ is hydrogen and $R_a$, $R_b$, $R_c$ and $R_d$ are as defined in Table 1.

Table 133: This table discloses the 169 compounds T133.001 to T133.169 of the formula Ia, wherein W is $W^1$, R is methyl, A is —CH$_2$CH=CH$_2$, $Q^1$ is 2-methoxy-4-nitro-phenyl, $Q^2$ is hydrogen and $R_a$, $R_b$, $R_c$ and $R_d$ are as defined in Table 1.

Table 134: This table discloses the 169 compounds T134.001 to T134.169 of the formula Ia, wherein W is $W^1$, R is methyl, A is —CH$_2$C≡CH, $Q^1$ is 2-methoxy-4-nitro-phenyl, $Q^2$ is hydrogen and $R_a$, $R_b$, $R_c$ and $R_d$ are as defined in Table 1.

Table 135: This table discloses the 169 compounds T135.001 to T135.169 of the formula Ia, wherein W is $W^1$, R is methyl, A is phenyl, $Q^1$ is 2-methoxy-4-nitro-phenyl, $Q^2$ is hydrogen and $R_a$, $R_b$, $R_c$ and $R_d$ are as defined in Table 1.

Table 136: This table discloses the 169 compounds T136.001 to T136.169 of the formula Ia, wherein W is $W^2$, R is methyl, A is hydrogen, $Q^1$ is n-butyl, $Q^2$ is hydrogen and $R_a$, $R_b$, $R_c$ and $R_d$ are as defined in Table 1.

Table 137: This table discloses the 169 compounds T137.001 to T137.169 of the formula Ia, wherein W is $W^2$, R is methyl, A is methyl, $Q^1$ is n-butyl, $Q^2$ is hydrogen and $R_a$, $R_b$, $R_c$ and $R_d$ are as defined in Table 1.

Table 138: This table discloses the 169 compounds T138.001 to T138.169 of the formula Ia, wherein W is $W^2$, R is methyl, A is —CH$_2$CH=CH$_2$, Q$^1$ is n-butyl, Q$^2$ is hydrogen and R$_a$, R$_b$, R$_c$ and R$_d$ are as defined in Table 1.
Table 139: This table discloses the 169 compounds T139.001 to T139.169 of the formula Ia, wherein W is W$^2$, R is methyl, A is —CH$_2$C≡CH, Q$^1$ is n-butyl, Q$^2$ is hydrogen and R$_a$, R$_b$, R$_c$ and R$_d$ are as defined in Table 1.
Table 140: This table discloses the 169 compounds T140.001 to T140.169 of the formula Ia, wherein W is W$^2$, R is methyl, A is phenyl, Q$^1$ is n-butyl, Q$^2$ is hydrogen and R$_a$, R$_b$, R$_c$ and R$_d$ are as defined in Table 1.
Table 141: This table discloses the 169 compounds T141.001 to T141.169 of the formula Ia, wherein W is W$^2$, R is methyl, A is hydrogen, Q$^1$ is 4-methyl-phenyl, Q$^2$ is hydrogen and R$_a$, R$_b$, R$_c$ and R$_d$ are as defined in Table 1.
Table 142: This table discloses the 169 compounds T142.001 to T142.169 of the formula Ia, wherein W is W$^2$, R is methyl, A is methyl, Q$^1$ is 4-methyl-phenyl, Q$^2$ is hydrogen and R$_a$, R$_b$, R$_c$ and R$_d$ are as defined in Table 1.
Table 143: This table discloses the 169 compounds T143.001 to T143.169 of the formula Ia, wherein W is W$^2$, R is methyl, A is —CH$_2$CH=CH$_2$, Q$^1$ is 4-methyl-phenyl, Q$^2$ is hydrogen and R$_a$, R$_b$, R$_c$ and R$_d$ are as defined in Table 1.
Table 144: This table discloses the 169 compounds T144.001 to T144.169 of the formula Ia, wherein W is W$^2$, R is methyl, A is —CH$_2$C≡CH, Q$^1$ is 4-methyl-phenyl, Q$^2$ is hydrogen and R$_a$, R$_b$, R$_c$ and R$_d$ are as defined in Table 1.
Table 145: This table discloses the 169 compounds T145.001 to T145.169 of the formula Ia, wherein W is W$^2$, R is methyl, A is phenyl, Q$^1$ is 4-methyl-phenyl, Q$^2$ is hydrogen and R$_a$, R$_b$, R$_c$ and R$_d$ are as defined in Table 1.
Table 146: This table discloses the 169 compounds T146.001 to T146.169 of the formula Ia, wherein W is W$^2$, R is methyl, A is hydrogen, Q$^1$ is 4-fluoro-phenyl, Q$^2$ is hydrogen and R$_a$, R$_b$, R$_c$ and R$_d$ are as defined in Table 1.
Table 147: This table discloses the 169 compounds T147.001 to T147.169 of the formula Ia, wherein W is W$^2$, R is methyl, A is methyl, Q$^1$ is 4-fluoro-phenyl, Q$^2$ is hydrogen and R$_a$, R$_b$, R$_c$ and R$_d$ are as defined in Table 1.
Table 148: This table discloses the 169 compounds T148.001 to T148.169 of the formula Ia, wherein W is W$^2$, R is methyl, A is —CH$_2$CH=CH$_2$, Q$^1$ is 4-fluoro-phenyl, Q$^2$ is hydrogen and R$_a$, R$_b$, R$_c$ and R$_d$ are as defined in Table 1.
Table 149: This table discloses the 169 compounds T149.001 to T149.169 of the formula Ia, wherein W is W$^2$, R is methyl, A is —CH$_2$C≡CH, Q$^1$ is 4-fluoro-phenyl, Q$^2$ is hydrogen and R$_a$, R$_b$, R$_c$ and R$_d$ are as defined in Table 1.
Table 150: This table discloses the 169 compounds T150.001 to T150.169 of the formula Ia, wherein W is W$^2$, R is methyl, A is phenyl, Q$^1$ is 4-fluoro-phenyl, Q$^2$ is hydrogen and R$_a$, R$_b$, R$_c$ and R$_d$ are as defined in Table 1.
Table 151: This table discloses the 169 compounds T151.001 to T151.169 of the formula Ia, wherein W is W$^2$, R is methyl, A is hydrogen, Q$^1$ is 4-methoxy-phenyl, Q$^2$ is hydrogen and R$_a$, R$_b$, R$_c$ and R$_d$ are as defined in Table 1.
Table 152: This table discloses the 169 compounds T152.001 to T152.169 of the formula Ia, wherein W is W$^2$, R is methyl, A is methyl, Q$^1$ is 4-methoxy-phenyl, Q$^2$ is hydrogen and R$_a$, R$_b$, R$_c$ and R$_d$ are as defined in Table 1.
Table 153: This table discloses the 169 compounds T153.001 to T153.169 of the formula Ia, wherein W is W$^2$, R is methyl, A is —CH$_2$CH=CH$_2$, Q$^1$ is 4-methoxy-phenyl, Q$^2$ is hydrogen and R$_a$, R$_b$, R$_c$ and R$_d$ are as defined in Table 1.
Table 154: This table discloses the 169 compounds T154.001 to T154.169 of the formula Ia, wherein W is W$^2$, R is methyl, A is —CH$_2$C≡CH, Q$^1$ is 4-methoxy-phenyl, Q$^2$ is hydrogen and R$_a$, R$_b$, R$_c$ and R$_d$ are as defined in Table 1.
Table 155: This table discloses the 169 compounds T155.001 to T155.169 of the formula Ia, wherein W is W$^2$, R is methyl, A is phenyl, Q$^1$ is 4-methoxy-phenyl, Q$^2$ is hydrogen and R$_a$, R$_b$, R$_c$ and R$_d$ are as defined in Table 1.
Table 156: This table discloses the 169 compounds T156.001 to T156.169 of the formula Ia, wherein W is W$^2$, R is methyl, A is hydrogen, Q$^1$ is 2-chloro-phenyl, Q$^2$ is hydrogen and R$_a$, R$_b$, R$_c$ and R$_d$ are as defined in Table 1.
Table 157: This table discloses the 169 compounds T157.001 to T157.169 of the formula Ia, wherein W is W$^2$, R is methyl, A is methyl, Q$^1$ is 2-chloro-phenyl, Q$^2$ is hydrogen and R$_a$, R$_b$, R$_c$ and R$_d$ are as defined in Table 1.
Table 158: This table discloses the 169 compounds T158.001 to T158.169 of the formula Ia, wherein W is W$^2$, R is methyl, A is —CH$_2$CH=CH$_2$, Q$^1$ is 2-chloro-phenyl, Q$^2$ is hydrogen and R$_a$, R$_b$, R$_c$ and R$_d$ are as defined in Table 1.
Table 159: This table discloses the 169 compounds T159.001 to T159.169 of the formula Ia, wherein W is W$^2$, R is methyl, A is —CH$_2$C≡CH, Q$^1$ is 2-chloro-phenyl, Q$^2$ is hydrogen and R$_a$, R$_b$, R$_c$ and R$_d$ are as defined in Table 1.
Table 160: This table discloses the 169 compounds T160.001 to T160.169 of the formula Ia, wherein W is W$^2$, R is methyl, A is phenyl, Q$^1$ is 2-chloro-phenyl, Q$^2$ is hydrogen and R$_a$, R$_b$, R$_c$ and R$_d$ are as defined in Table 1.
Table 161: This table discloses the 169 compounds T161.001 to T161.169 of the formula Ia, wherein W is W$^2$, R is methyl, A is hydrogen, Q$^1$ is phenyl, Q$^2$ is hydrogen and R$_a$, R$_b$, R$_c$ and R$_d$ are as defined in Table 1.
Table 162: This table discloses the 169 compounds T162.001 to T162.169 of the formula Ia, wherein W is W$^2$, R is methyl, A is methyl, Q$^1$ is phenyl, Q$^2$ is hydrogen and R$_a$, R$_b$, R$_c$ and R$_d$ are as defined in Table 1.
Table 163: This table discloses the 169 compounds T163.001 to T163.169 of the formula Ia, wherein W is W$^2$, R is methyl, A is —CH$_2$CH=CH$_2$, Q$^1$ is phenyl, Q$^2$ is hydrogen and R$_a$, R$_b$, R$_c$ and R$_d$ are as defined in Table 1.
Table 164: This table discloses the 169 compounds T164.001 to T164.169 of the formula Ia, wherein W is W$^2$, R is methyl, A is —CH$_2$C≡CH, Q$^1$ is phenyl, Q$^2$ is hydrogen and R$_a$, R$_b$, R$_c$ and R$_d$ are as defined in Table 1.
Table 165: This table discloses the 169 compounds T165.001 to T165.169 of the formula Ia, wherein W is W$^2$, R is methyl, A is phenyl, Q$^1$ is phenyl, Q$^2$ is hydrogen and R$_a$, R$_b$, R$_c$ and R$_d$ are as defined in Table 1.
Table 166: This table discloses the 169 compounds T166.001 to T166.169 of the formula Ia, wherein W is W$^2$, R is methyl, A is hydrogen, Q$^1$ is 4-nitro-phenyl, Q$^2$ is hydrogen and R$_a$, R$_b$, R$_c$ and R$_d$ are as defined in Table 1.
Table 167: This table discloses the 169 compounds T167.001 to T167.169 of the formula Ia, wherein W is W$^2$, R is methyl, A is methyl, Q$^1$ is 4-nitro-phenyl, Q$^2$ is hydrogen and R$_a$, R$_b$, R$_c$ and R$_d$ are as defined in Table 1.
Table 169: This table discloses the 169 compounds T169.001 to T169.169 of the formula Ia, wherein W is W$^2$, R is methyl, A is —CH$_2$CH=CH$_2$, Q$^1$ is 4-nitro-phenyl, Q$^2$ is hydrogen and R$_a$, R$_b$, R$_c$ and R$_d$ are as defined in Table 1.
Table 169: This table discloses the 169 compounds T169.001 to T169.169 of the formula Ia, wherein W is W$^2$, R is methyl, A is —CH$_2$C≡CH, Q$^1$ is 4-nitro-phenyl, Q$^2$ is hydrogen and R$_a$, R$_b$, R$_c$ and R$_d$ are as defined in Table 1.
Table 170: This table discloses the 169 compounds T170.001 to T170.169 of the formula Ia, wherein W is W$^2$, R is methyl, A is phenyl, Q$^1$ is 4-nitro-phenyl, Q$^2$ is hydrogen and R$_a$, R$_b$, R$_c$ and R$_d$ are as defined in Table 1.

Table 171: This table discloses the 169 compounds T171.001 to T171.169 of the formula Ia, wherein W is $W^2$, R is methyl, A is hydrogen, $Q^1$ is 2,6-dimethyl-phenyl, $Q^2$ is hydrogen and $R_a$, $R_b$, $R_c$ and $R_d$ are as defined in Table 1.
Table 172: This table discloses the 169 compounds T172.001 to T172.169 of the formula Ia, wherein W is $W^2$, R is methyl, A is methyl, $Q^1$ is 2,6-dimethyl-phenyl, $Q^2$ is hydrogen and $R_a$, $R_b$, $R_c$ and $R_d$ are as defined in Table 1.
Table 173: This table discloses the 169 compounds T173.001 to T173.169 of the formula Ia, wherein W is $W^2$, R is methyl, A is —$CH_2CH=CH_2$, $Q^1$ is 2,6-dimethyl-phenyl, $Q^2$ is hydrogen and $R_a$, $R_b$, $R_c$ and $R_d$ are as defined in Table 1.
Table 174: This table discloses the 169 compounds T174.001 to T174.169 of the formula Ia, wherein W is $W^2$, R is methyl, A is —$CH_2C\equiv CH$, $Q^1$ is 2,6-dimethyl-phenyl, $Q^2$ is hydrogen and $R_a$, $R_b$, $R_c$ and $R_d$ are as defined in Table 1.
Table 175: This table discloses the 169 compounds T175.001 to T175.169 of the formula Ia, wherein W is $W^2$, R is methyl, A is phenyl, $Q^1$ is 2,6-dimethyl-phenyl, $Q^2$ is hydrogen and $R_a$, $R_b$, $R_c$ and $R_d$ are as defined in Table 1.
Table 176: This table discloses the 169 compounds T176.001 to T176.169 of the formula Ia, wherein W is $W^2$, R is methyl, A is hydrogen, $Q^1$ is 2-methoxy-4-nitro-phenyl, $Q^2$ is hydrogen and $R_a$, $R_b$, $R_c$ and $R_d$ are as defined in Table 1.
Table 177: This table discloses the 169 compounds T177.001 to T177.169 of the formula Ia, wherein W is $W^2$, R is methyl, A is methyl, $Q^1$ is 2-methoxy-4-nitro-phenyl, $Q^2$ is hydrogen and $R_a$, $R_b$, $R_c$ and $R_d$ are as defined in Table 1.
Table 178: This table discloses the 169 compounds T178.001 to T178.169 of the formula Ia, wherein W is $W^2$, R is methyl, A is —$CH_2CH=CH_2$, $Q^1$ is 2-methoxy-4-nitro-phenyl, $Q^2$ is hydrogen and $R_a$, $R_b$, $R_c$ and $R_d$ are as defined in Table 1.
Table 179: This table discloses the 169 compounds T179.001 to T179.169 of the formula Ia, wherein W is $W^2$, R is methyl, A is —$CH_2C\equiv CH$, $Q^1$ is 2-methoxy-4-nitro-phenyl, $Q^2$ is hydrogen and $R_a$, $R_b$, $R_c$ and $R_d$ are as defined in Table 1.
Table 180: This table discloses the 169 compounds T180.001 to T180.169 of the formula Ia, wherein W is $W^2$, R is methyl, A is phenyl, $Q^1$ is 2-methoxy-4-nitro-phenyl, $Q^2$ is hydrogen and $R_a$, $R_b$, $R_c$ and $R_d$ are as defined in Table 1.
Table 181: This table discloses the 169 compounds T181.001 to T181.169 of the formula Ia, wherein W is $W^2$, R is ethyl, A is hydrogen, $Q^1$ is n-butyl, $Q^2$ is hydrogen and $R_a$, $R_b$, $R_c$ and $R_d$ are as defined in Table 1.
Table 182: This table discloses the 169 compounds T182.001 to T182.169 of the formula Ia, wherein W is $W^2$, R is ethyl, A is methyl, $Q^1$ is n-butyl, $Q^2$ is hydrogen and $R_a$, $R_b$, $R_c$ and $R_d$ are as defined in Table 1.
Table 183: This table discloses the 169 compounds T183.001 to T183.169 of the formula Ia, wherein W is $W^2$, R is ethyl, A is —$CH_2CH=CH_2$, $Q^1$ is n-butyl, $Q^2$ is hydrogen and $R_a$, $R_b$, $R_c$ and $R_d$ are as defined in Table 1.
Table 184: This table discloses the 169 compounds T184.001 to T184.169 of the formula Ia, wherein W is $W^2$, R is ethyl, A is —$CH_2C\equiv CH$, $Q^1$ is n-butyl, $Q^2$ is hydrogen and $R_a$, $R_b$, $R_c$ and $R_d$ are as defined in Table 1.
Table 185: This table discloses the 169 compounds T185.001 to T185.169 of the formula Ia, wherein W is $W^2$, R is ethyl, A is phenyl, $Q^1$ is n-butyl, $Q^2$ is hydrogen and $R_a$, $R_b$, $R_c$ and $R_d$ are as defined in Table 1.
Table 186: This table discloses the 169 compounds T186.001 to T186.169 of the formula Ia, wherein W is $W^2$, R is ethyl, A is hydrogen, $Q^1$ is 4-methyl-phenyl, $Q^2$ is hydrogen and $R_a$, $R_b$, $R_c$ and $R_d$ are as defined in Table 1.
Table 187: This table discloses the 169 compounds T187.001 to T187.169 of the formula Ia, wherein W is $W^2$, R is ethyl, A is methyl, $Q^1$ is 4-methyl-phenyl, $Q^2$ is hydrogen and $R_a$, $R_b$, $R_c$ and $R_d$ are as defined in Table 1.
Table 188: This table discloses the 169 compounds T188.001 to T188.169 of the formula Ia, wherein W is $W^2$, R is ethyl, A is —$CH_2CH=CH_2$, $Q^1$ is 4-methyl-phenyl, $Q^2$ is hydrogen and $R_a$, $R_b$, $R_c$ and $R_d$ are as defined in Table 1.
Table 189: This table discloses the 169 compounds T189.001 to T189.169 of the formula Ia, wherein W is $W^2$, R is ethyl, A is —$CH_2C\equiv CH$, $Q^1$ is 4-methyl-phenyl, $Q^2$ is hydrogen and $R_a$, $R_b$, $R_c$ and $R_d$ are as defined in Table 1.
Table 190: This table discloses the 169 compounds T190.001 to T190.169 of the formula Ia, wherein W is $W^2$, R is ethyl, A is phenyl, $Q^1$ is 4-methyl-phenyl, $Q^2$ is hydrogen and $R_a$, $R_b$, $R_c$ and $R_d$ are as defined in Table 1.
Table 191: This table discloses the 169 compounds T191.001 to T191.169 of the formula Ia, wherein W is $W^2$, R is ethyl, A is hydrogen, $Q^1$ is 4-fluoro-phenyl, $Q^2$ is hydrogen and $R_a$, $R_b$, $R_c$ and $R_d$ are as defined in Table 1.
Table 192: This table discloses the 169 compounds T192.001 to T192.169 of the formula Ia, wherein W is $W^2$, R is ethyl, A is methyl, $Q^1$ is 4-fluoro-phenyl, $Q^2$ is hydrogen and $R_a$, $R_b$, $R_c$ and $R_d$ are as defined in Table 1.
Table 193: This table discloses the 169 compounds T193.001 to T193.169 of the formula Ia, wherein W is $W^2$, R is ethyl, A is —$CH_2CH=CH_2$, $Q^1$ is 4-fluoro-phenyl, $Q^2$ is hydrogen and $R_a$, $R_b$, $R_c$ and $R_d$ are as defined in Table 1.
Table 194: This table discloses the 169 compounds T194.001 to T194.169 of the formula Ia, wherein W is $W^2$, R is ethyl, A is —$CH_2C\equiv CH$, $Q^1$ is 4-fluoro-phenyl, $Q^2$ is hydrogen and $R_a$, $R_b$, $R_c$ and $R_d$ are as defined in Table 1.
Table 195: This table discloses the 169 compounds T195.001 to T195.169 of the formula Ia, wherein W is $W^2$, R is ethyl, A is phenyl, $Q^1$ is 4-fluoro-phenyl, $Q^2$ is hydrogen and $R_a$, $R_b$, $R_c$ and $R_d$ are as defined in Table 1.
Table 196: This table discloses the 169 compounds T196.001 to T196.169 of the formula Ia, wherein W is $W^2$, R is ethyl, A is hydrogen, $Q^1$ is 4-methoxy-phenyl, $Q^2$ is hydrogen and $R_a$, $R_b$, $R_c$ and $R_d$ are as defined in Table 1.
Table 197: This table discloses the 169 compounds T197.001 to T197.169 of the formula Ia, wherein W is $W^2$, R is ethyl, A is methyl, $Q^1$ is 4-methoxy-phenyl, $Q^2$ is hydrogen and $R_a$, $R_b$, $R_c$ and $R_d$ are as defined in Table 1.
Table 198: This table discloses the 169 compounds T198.001 to T198.169 of the formula Ia, wherein W is $W^2$, R is ethyl, A is —$CH_2CH=CH_2$, $Q^1$ is 4-methoxy-phenyl, $Q^2$ is hydrogen and $R_a$, $R_b$, $R_c$ and $R_d$ are as defined in Table 1.
Table 199: This table discloses the 169 compounds T199.001 to T199.169 of the formula Ia, wherein W is $W^2$, R is ethyl, A is —$CH_2C\equiv CH$, $Q^1$ is 4-methoxy-phenyl, $Q^2$ is hydrogen and $R_a$, $R_b$, $R_c$ and $R_d$ are as defined in Table 1.
Table 200: This table discloses the 169 compounds T200.001 to T200.169 of the formula Ia, wherein W is $W^2$, R is ethyl, A is phenyl, $Q^1$ is 4-methoxy-phenyl, $Q^2$ is hydrogen and $R_a$, $R_b$, $R_c$ and $R_d$ are as defined in Table 1.
Table 201: This table discloses the 169 compounds T201.001 to T201.169 of the formula Ia, wherein W is $W^2$, R is ethyl, A is hydrogen, $Q^1$ is 2-chloro-phenyl, $Q^2$ is hydrogen and $R_a$, $R_b$, $R_c$ and $R_d$ are as defined in Table 1.
Table 202: This table discloses the 169 compounds T202.001 to T202.169 of the formula Ia, wherein W is $W^2$, R is ethyl, A is methyl, $Q^1$ is 2-chloro-phenyl, $Q^2$ is hydrogen and $R_a$, $R_b$, $R_c$ and $R_d$ are as defined in Table 1.

Table 203: This table discloses the 169 compounds T203.001 to T203.169 of the formula Ia, wherein W is $W^2$, R is ethyl, A is —$CH_2CH$=$CH_2$, $Q^1$ is 2-chloro-phenyl, $Q^2$ is hydrogen and $R_a$, $R_b$, $R_c$ and $R_d$ are as defined in Table 1.
Table 204: This table discloses the 169 compounds T204.001 to T204.169 of the formula Ia, wherein W is $W^2$, R is ethyl, A is —$CH_2C$≡$CH$, $Q^1$ is 2-chloro-phenyl, $Q^2$ is hydrogen and $R_a$, $R_b$, $R_c$ and $R_d$ are as defined in Table 1.
Table 205: This table discloses the 169 compounds T205.001 to T205.169 of the formula Ia, wherein W is $W^2$, R is ethyl, A is phenyl, $Q^1$ is 2-chloro-phenyl, $Q^2$ is hydrogen and $R_a$, $R_b$, $R_c$ and $R_d$ are as defined in Table 1.
Table 206: This table discloses the 169 compounds T206.001 to T206.169 of the formula Ia, wherein W is $W^2$, R is ethyl, A is hydrogen, $Q^1$ is phenyl, $Q^2$ is hydrogen and $R_a$, $R_b$, $R_c$ and $R_d$ are as defined in Table 1.
Table 207: This table discloses the 169 compounds T207.001 to T207.169 of the formula Ia, wherein W is $W^2$, R is ethyl, A is methyl, $Q^1$ is phenyl, $Q^2$ is hydrogen and $R_a$, $R_b$, $R_c$ and $R_d$ are as defined in Table 1.
Table 208: This table discloses the 169 compounds T208.001 to T208.169 of the formula Ia, wherein W is $W^2$, R is ethyl, A is —$CH_2CH$=$CH_2$, $Q^1$ is phenyl, $Q^2$ is hydrogen and $R_a$, $R_b$, $R_c$ and $R_d$ are as defined in Table 1.
Table 209: This table discloses the 169 compounds T209.001 to T209.169 of the formula Ia, wherein W is $W^2$, R is ethyl, A is —$CH_2C$≡$CH$, $Q^1$ is phenyl, $Q^2$ is hydrogen and $R_a$, $R_b$, $R_c$ and $R_d$ are as defined in Table 1.
Table 210: This table discloses the 169 compounds T210.001 to T210.169 of the formula Ia, wherein W is $W^2$, R is ethyl, A is phenyl, $Q^1$ is phenyl, $Q^2$ is hydrogen and $R_a$, $R_b$, $R_c$ and $R_d$ are as defined in Table 1.
Table 211: This table discloses the 169 compounds T211.001 to T211.169 of the formula Ia, wherein W is $W^2$, R is ethyl, A is hydrogen, $Q^1$ is 4-nitro-phenyl, $Q^2$ is hydrogen and $R_a$, $R_b$, $R_c$ and $R_d$ are as defined in Table 1.
Table 212: This table discloses the 169 compounds T212.001 to T212.169 of the formula Ia, wherein W is $W^2$, R is ethyl, A is methyl, $Q^1$ is 4-nitro-phenyl, $Q^2$ is hydrogen and $R_a$, $R_b$, $R_c$ and $R_d$ are as defined in Table 1.
Table 213: This table discloses the 169 compounds T213.001 to T213.169 of the formula Ia, wherein W is $W^2$, R is ethyl, A is —$CH_2CH$=$CH_2$, $Q^1$ is 4-nitro-phenyl, $Q^2$ is hydrogen and $R_a$, $R_b$, $R_c$ and $R_d$ are as defined in Table 1.
Table 214: This table discloses the 169 compounds T214.001 to T214.169 of the formula Ia, wherein W is $W^2$, R is ethyl, A is —$CH_2C$≡$CH$, $Q^1$ is 4-nitro-phenyl, $Q^2$ is hydrogen and $R_a$, $R_b$, $R_c$ and $R_d$ are as defined in Table 1.
Table 215: This table discloses the 169 compounds T215.001 to T215.169 of the formula Ia, wherein W is $W^2$, R is ethyl, A is phenyl, $Q^1$ is 4-nitro-phenyl, $Q^2$ is hydrogen and $R_a$, $R_b$, $R_c$ and $R_d$ are as defined in Table 1.
Table 216: This table discloses the 169 compounds T216.001 to T216.169 of the formula Ia, wherein W is $W^2$, R is ethyl, A is hydrogen, $Q^1$ is 2,6-dimethyl-phenyl, $Q^2$ is hydrogen and $R_a$, $R_b$, $R_c$ and $R_d$ are as defined in Table 1.
Table 217: This table discloses the 169 compounds T217.001 to T217.169 of the formula Ia, wherein W is $W^2$, R is ethyl, A is methyl, $Q^1$ is 2,6-dimethyl-phenyl, $Q^2$ is hydrogen and $R_a$, $R_b$, $R_c$ and $R_d$ are as defined in Table 1.
Table 218: This table discloses the 169 compounds T218.001 to T218.169 of the formula Ia, wherein W is $W^2$, R is ethyl, A is —$CH_2CH$=$CH_2$, $Q^1$ is 2,6-dimethyl-phenyl, $Q^2$ is hydrogen and $R_a$, $R_b$, $R_c$ and $R_d$ are as defined in Table 1.
Table 219: This table discloses the 169 compounds T219.001 to T219.169 of the formula Ia, wherein W is $W^2$, R is ethyl, A is —$CH_2C$≡$CH$, $Q^1$ is 2,6-dimethyl-phenyl, $Q^2$ is hydrogen and $R_a$, $R_b$, $R_c$ and $R_d$ are as defined in Table 1.
Table 220: This table discloses the 169 compounds T220.001 to T220.169 of the formula Ia, wherein W is $W^2$, R is ethyl, A is phenyl, $Q^1$ is 2,6-dimethyl-phenyl, $Q^2$ is hydrogen and $R_a$, $R_b$, $R_c$ and $R_d$ are as defined in Table 1.
Table 221: This table discloses the 169 compounds T221.001 to T221.169 of the formula Ia, wherein W is $W^2$, R is ethyl, A is hydrogen, $Q^1$ is 2-methoxy-4-nitro-phenyl, $Q^2$ is hydrogen and $R_a$, $R_b$, $R_c$ and $R_d$ are as defined in Table 1.
Table 222: This table discloses the 169 compounds T222.001 to T222.169 of the formula Ia, wherein W is $W^2$, R is ethyl, A is methyl, $Q^1$ is 2-methoxy-4-nitro-phenyl, $Q^2$ is hydrogen and $R_a$, $R_b$, $R_c$ and $R_d$ are as defined in Table 1.
Table 223: This table discloses the 169 compounds T223.001 to T223.169 of the formula Ia, wherein W is $W^2$, R is ethyl, A is —$CH_2CH$=$CH_2$, $Q^1$ is 2-methoxy-4-nitro-phenyl, $Q^2$ is hydrogen and $R_a$, $R_b$, $R_c$ and $R_d$ are as defined in Table 1.
Table 224: This table discloses the 169 compounds T224.001 to T224.169 of the formula Ia, wherein W is $W^2$, R is ethyl, A is —$CH_2C$≡$CH$, $Q^1$ is 2-methoxy-4-nitro-phenyl, $Q^2$ is hydrogen and $R_a$, $R_b$, $R_c$ and $R_d$ are as defined in Table 1.
Table 225: This table discloses the 169 compounds T225.001 to T225.169 of the formula Ia, wherein W is $W^2$, R is ethyl, A is phenyl, $Q^1$ is 2-methoxy-4-nitro-phenyl, $Q^2$ is hydrogen and $R_a$, $R_b$, $R_c$ and $R_d$ are as defined in Table 1.
Table 226: This table discloses the 169 compounds T 226.001 to T 226.169 of the formula Ia, wherein W is $W^3$, A is hydrogen, $Q^1$ is n-butyl, $Q^2$ is hydrogen and $R_a$, $R_b$, $R_c$ and $R_d$ are as defined in Table 1.
Table 227: This table discloses the 169 compounds T 227.001 to T 227.169 of the formula Ia, wherein W is $W^3$, A is methyl, $Q^1$ is n-butyl, $Q^2$ is hydrogen and $R_a$, $R_b$, $R_c$ and $R_d$ are as defined in Table 1.
Table 228: This table discloses the 169 compounds T 228.001 to T 228.169 of the formula Ia, wherein W is $W^3$, A is —$CH_2CH$=$CH_2$, $Q^1$ is n-butyl, $Q^2$ is hydrogen and $R_a$, $R_b$, $R_c$ and $R_d$ are as defined in Table 1.
Table 229: This table discloses the 169 compounds T 229.001 to T 229.169 of the formula Ia, wherein W is $W^3$, A is —$CH_2C$≡$CH$, $Q^1$ is n-butyl, $Q^2$ is hydrogen and $R_a$, $R_b$, $R_c$ and $R_d$ are as defined in Table 1.
Table 230: This table discloses the 169 compounds T 230.001 to T 230.169 of the formula Ia, wherein W is $W^3$, A is phenyl, $Q^1$ is n-butyl, $Q^2$ is hydrogen and $R_a$, $R_b$, $R_c$ and $R_d$ are as defined in Table 1.
Table 231: This table discloses the 169 compounds T 231.001 to T 231.169 of the formula Ia, wherein W is $W^3$, A is hydrogen, $Q^1$ is 4-methyl-phenyl, $Q^2$ is hydrogen and $R_a$, $R_b$, $R_c$ and $R_d$ are as defined in Table 1.
Table 232: This table discloses the 169 compounds T 232.001 to T 232.169 of the formula Ia, wherein W is $W^3$, A is methyl, $Q^1$ is 4-methyl-phenyl, $Q^2$ is hydrogen and $R_a$, $R_b$, $R_c$ and $R_d$ are as defined in Table 1.
Table 233: This table discloses the 169 compounds T 233.001 to T 233.169 of the formula Ia, wherein W is $W^3$, A is —$CH_2CH$=$CH_2$, $Q^1$ is 4-methyl-phenyl, $Q^2$ is hydrogen and $R_a$, $R_b$, $R_c$ and $R_d$ are as defined in Table 1.
Table 234: This table discloses the 169 compounds T 234.001 to T 234.169 of the formula Ia, wherein W is $W^3$, A is —$CH_2C$≡$CH$, $Q^1$ is 4-methyl-phenyl, $Q^2$ is hydrogen and $R_a$, $R_b$, $R_c$ and $R_d$ are as defined in Table 1.
Table 235: This table discloses the 169 compounds T 235.001 to T 235.169 of the formula Ia, wherein W is $W^3$, A is phenyl, $Q^1$ is 4-methyl-phenyl, $Q^2$ is hydrogen and $R_a$, $R_b$, $R_c$ and $R_d$ are as defined in Table 1.
Table 236: This table discloses the 169 compounds T 236.001 to T 236.169 of the formula Ia, wherein W is $W^3$, A is hydrogen, $Q^1$ is 4-fluoro-phenyl, $Q^2$ is hydrogen and $R_a$, $R_b$, $R_c$ and $R_d$ are as defined in Table 1.
Table 237: This table discloses the 169 compounds T 237.001 to T 237.169 of the formula Ia, wherein W is $W^3$, A is methyl, $Q^1$ is 4-fluoro-phenyl, $Q^2$ is hydrogen and $R_a$, $R_b$, $R_c$ and $R_d$ are as defined in Table 1.
Table 238: This table discloses the 169 compounds T 238.001 to T 238.169 of the formula Ia, wherein W is $W^3$, A is —$CH_2CH$=$CH_2$, $Q^1$ is 4-fluoro-phenyl, $Q^2$ is hydrogen and $R_a$, $R_b$, $R_c$ and $R_d$ are as defined in Table 1.
Table 239: This table discloses the 169 compounds T 239.001 to T 239.169 of the formula Ia, wherein W is $W^3$, A is —$CH_2C$≡$CH$, $Q^1$ is 4-fluoro-phenyl, $Q^2$ is hydrogen and $R_a$, $R_b$, $R_c$ and $R_d$ are as defined in Table 1.
Table 240: This table discloses the 169 compounds T 240.001 to T 240.169 of the formula Ia, wherein W is $W^3$, A is phenyl, $Q^1$ is 4-fluoro-phenyl, $Q^2$ is hydrogen and $R_a$, $R_b$, $R_c$ and $R_d$ are as defined in Table 1.
Table 241: This table discloses the 169 compounds T 241.001 to T 241.169 of the formula Ia, wherein W is $W^3$, A is hydrogen, $Q^1$ is 4-methoxy-phenyl, $Q^2$ is hydrogen and $R_a$, $R_b$, $R_c$ and $R_d$ are as defined in Table 1.
Table 242: This table discloses the 169 compounds T 242.001 to T 242.169 of the formula Ia, wherein W is $W^3$, A is methyl, $Q^1$ is 4-methoxy-phenyl, $Q^2$ is hydrogen and $R_a$, $R_b$, $R_c$ and $R_d$ are as defined in Table 1.
Table 243: This table discloses the 169 compounds T 243.001 to T 243.169 of the formula Ia, wherein W is $W^3$, A is —$CH_2CH$=$CH_2$, $Q^1$ is 4-methoxy-phenyl, $Q^2$ is hydrogen and $R_a$, $R_b$, $R_c$ and $R_d$ are as defined in Table 1.
Table 244: This table discloses the 169 compounds T 244.001 to T 244.169 of the formula Ia, wherein W is $W^3$, A is —$CH_2C$≡$CH$, $Q^1$ is 4-methoxy-phenyl, $Q^2$ is hydrogen and $R_a$, $R_b$, $R_c$ and $R_d$ are as defined in Table 1.
Table 245: This table discloses the 169 compounds T 245.001 to T 245.169 of the formula Ia, wherein W is $W^3$, A is phenyl, $Q^1$ is 4-methoxy-phenyl, $Q^2$ is hydrogen and $R_a$, $R_b$, $R_c$ and $R_d$ are as defined in Table 1.
Table 246: This table discloses the 169 compounds T 246.001 to T 246.169 of the formula Ia, wherein W is $W^3$, A is hydrogen, $Q^1$ is 2-chloro-phenyl, $Q^2$ is hydrogen and $R_a$, $R_b$, $R_c$ and $R_d$ are as defined in Table 1.
Table 247: This table discloses the 169 compounds T 247.001 to T 247.169 of the formula Ia, wherein W is $W^3$, A is methyl, $Q^1$ is 2-chloro-phenyl, $Q^2$ is hydrogen and $R_a$, $R_b$, $R_c$ and $R_d$ are as defined in Table 1.
Table 248: This table discloses the 169 compounds T 248.001 to T 248.169 of the formula Ia, wherein W is $W^3$, A is —$CH_2CH$=$CH_2$, $Q^1$ is 2-chloro-phenyl, $Q^2$ is hydrogen and $R_a$, $R_b$, $R_c$ and $R_d$ are as defined in Table 1.
Table 249: This table discloses the 169 compounds T 249.001 to T 249.169 of the formula Ia, wherein W is $W^3$, A is —$CH_2C$≡$CH$, $Q^1$ is 2-chloro-phenyl, $Q^2$ is hydrogen and $R_a$, $R_b$, $R_c$ and $R_d$ are as defined in Table 1.
Table 250: This table discloses the 169 compounds T 250.001 to T 250.169 of the formula Ia, wherein W is $W^3$, A is phenyl, $Q^1$ is 2-chloro-phenyl, $Q^2$ is hydrogen and $R_a$, $R_b$, $R_c$ and $R_d$ are as defined in Table 1.
Table 251: This table discloses the 169 compounds T 251.001 to T 251.169 of the formula Ia, wherein W is $W^3$, A is hydrogen, $Q^1$ is phenyl, $Q^2$ is hydrogen and $R_a$, $R_b$, $R_c$ and $R_d$ are as defined in Table 1.
Table 252: This table discloses the 169 compounds T 252.001 to T 252.169 of the formula Ia, wherein W is $W^3$, A is methyl, $Q^1$ is phenyl, $Q^2$ is hydrogen and $R_a$, $R_b$, $R_c$ and $R_d$ are as defined in Table 1.
Table 253: This table discloses the 169 compounds T 253.001 to T 253.169 of the formula Ia, wherein W is $W^3$, A is —$CH_2CH$=$CH_2$, $Q^1$ is phenyl, $Q^2$ is hydrogen and $R_a$, $R_b$, $R_c$ and $R_d$ are as defined in Table 1.
Table 254: This table discloses the 169 compounds T 254.001 to T 254.169 of the formula Ia, wherein W is $W^3$, A is —$CH_2C$≡$CH$, $Q^1$ is phenyl, $Q^2$ is hydrogen and $R_a$, $R_b$, $R_c$ and $R_d$ are as defined in Table 1.
Table 255: This table discloses the 169 compounds T 255.001 to T 255.169 of the formula Ia, wherein W is $W^3$, A is phenyl, $Q^1$ is phenyl, $Q^2$ is hydrogen and $R_a$, $R_b$, $R_c$ and $R_d$ are as defined in Table 1.
Table 256: This table discloses the 169 compounds T 256.001 to T 256.169 of the formula Ia, wherein W is $W^3$, A is hydrogen, $Q^1$ is 4-nitro-phenyl, $Q^2$ is hydrogen and $R_a$, $R_b$, $R_c$ and $R_d$ are as defined in Table 1.
Table 257: This table discloses the 169 compounds T 257.001 to T 257.169 of the formula Ia, wherein W is $W^3$, A is methyl, $Q^1$ is 4-nitro-phenyl, $Q^2$ is hydrogen and $R_a$, $R_b$, $R_c$ and $R_d$ are as defined in Table 1.
Table 258: This table discloses the 169 compounds T 258.001 to T 258.169 of the formula Ia, wherein W is $W^3$, A is —$CH_2CH$=$CH_2$, $Q^1$ is 4-nitro-phenyl, $Q^2$ is hydrogen and $R_a$, $R_b$, $R_c$ and $R_d$ are as defined in Table 1.
Table 259: This table discloses the 169 compounds T 259.001 to T 259.169 of the formula Ia, wherein W is $W^3$, A is —$CH_2C$≡$CH$, $Q^1$ is 4-nitro-phenyl, $Q^2$ is hydrogen and $R_a$, $R_b$, $R_c$ and $R_d$ are as defined in Table 1.
Table 260: This table discloses the 169 compounds T 260.001 to T 260.169 of the formula Ia, wherein W is $W^3$, A is phenyl, $Q^1$ is 4-nitro-phenyl, $Q^2$ is hydrogen and $R_a$, $R_b$, $R_c$ and $R_d$ are as defined in Table 1.
Table 261: This table discloses the 169 compounds T 261.001 to T 261.169 of the formula Ia, wherein W is $W^3$, A is hydrogen, $Q^1$ is 2,6-dimethyl-phenyl, $Q^2$ is hydrogen and $R_a$, $R_b$, $R_c$ and $R_d$ are as defined in Table 1.
Table 262: This table discloses the 169 compounds T 262.001 to T 262.169 of the formula Ia, wherein W is $W^3$, A is methyl, $Q^1$ is 2,6-dimethyl-phenyl, $Q^2$ is hydrogen and $R_a$, $R_b$, $R_c$ and $R_d$ are as defined in Table 1.
Table 263: This table discloses the 169 compounds T 263.001 to T 263.169 of the formula Ia, wherein W is $W^3$, A is —$CH_2CH$=$CH_2$, $Q^1$ is 2,6-dimethyl-phenyl, $Q^2$ is hydrogen and $R_a$, $R_b$, $R_c$ and $R_d$ are as defined in Table 1.
Table 264: This table discloses the 169 compounds T 264.001 to T 264.169 of the formula Ia, wherein W is $W^3$, A is —$CH_2C$≡$CH$, $Q^1$ is 2,6-dimethyl-phenyl, $Q^2$ is hydrogen and $R_a$, $R_b$, $R_c$ and $R_d$ are as defined in Table 1.
Table 265: This table discloses the 169 compounds T 265.001 to T 265.169 of the formula Ia, wherein W is $W^3$, A is phenyl, $Q^1$ is 2,6-dimethyl-phenyl, $Q^2$ is hydrogen and $R_a$, $R_b$, $R_c$ and $R_d$ are as defined in Table 1.
Table 266: This table discloses the 169 compounds T 266.001 to T 266.169 of the formula Ia, wherein W is $W^3$, A is hydrogen, $Q^1$ is 2-methoxy-4-nitro-phenyl, $Q^2$ is hydrogen and $R_a$, $R_b$, $R_c$ and $R_d$ are as defined in Table 1.
Table 267: This table discloses the 169 compounds T 267.001 to T 267.169 of the formula Ia, wherein W is $W^3$, A is methyl, $Q^1$ is 2-methoxy-4-nitro-phenyl, $Q^2$ is hydrogen and $R_a$, $R_b$, $R_c$ and $R_d$ are as defined in Table 1.
Table 268: This table discloses the 169 compounds T 268.001 to T 268.169 of the formula Ia, wherein W is $W^3$, A is —CH$_2$CH═CH$_2$, Q$^1$ is 2-methoxy-4-nitro-phenyl, Q$^2$ is hydrogen and R$_a$, R$_b$, R$_c$ and R$_d$ are as defined in Table 1.
Table 269: This table discloses the 169 compounds T 269.001 to T 269.169 of the formula Ia, wherein W is W$^3$, A is —CH$_2$C≡CH, Q$^1$ is 2-methoxy-4-nitro-phenyl, Q$^2$ is hydrogen and R$_a$, R$_b$, R$_c$ and R$_d$ are as defined in Table 1.
Table 270: This table discloses the 169 compounds T 270.001 to T 270.169 of the formula Ia, wherein W is W$^3$, A is phenyl, Q$^1$ is 2-methoxy-4-nitro-phenyl, Q$^2$ is hydrogen and R$_a$, R$_b$, R$_c$ and R$_d$ are as defined in Table 1.
Table 271: This table discloses the 169 compounds T 271.001 to T 271.169 of the formula Ia, wherein W is W$^3$, A is hydrogen, Q$^1$ is p-tolylsulfonylmethyl, Q$^2$ is hydrogen and R$_a$, R$_b$, R$_c$ and R$_d$ are as defined in Table 1.
Table 272: This table discloses the 169 compounds T 272.001 to T 272.169 of the formula Ia, wherein W is W$^3$, A is methyl, Q$^1$ is p-tolylsulfonylmethyl, Q$^2$ is hydrogen and R$_a$, R$_b$, R$_c$ and R$_d$ are as defined in Table 1.
Table 273: This table discloses the 169 compounds T 273.001 to T 273.169 of the formula Ia, wherein W is W$^3$, A is —CH$_2$CH═CH$_2$, Q$^1$ p-tolylsulfonylmethyl, Q$^2$ is hydrogen and R$_a$, R$_b$, R$_c$ and R$_d$ are as defined in Table 1.
Table 274: This table discloses the 169 compounds T 274.001 to T 274.169 of the formula Ia, wherein W is W$^3$, A is —CH$_2$C≡CH, Q$^1$ is p-tolylsulfonylmethyl, Q$^2$ is hydrogen and R$_a$, R$_b$, R$_c$ and R$_d$ are as defined in Table 1.
Table 275: This table discloses the 169 compounds T 275.001 to T 275.169 of the formula Ia, wherein W is W$^3$, A is phenyl, Q$^1$ is p-tolylsulfonylmethyl, Q$^2$ is hydrogen and R$_a$, R$_b$, R$_c$ and R$_d$ are as defined in Table 1.
Table 276: This table discloses the 169 compounds T 276.001 to T 276.169 of the formula Ia, wherein W is W$^{13}$, R is hydrogen, A is hydrogen, Q$^1$ is p-tolylsulfonylmethyl, Q$^2$ is hydrogen and R$_a$, R$_b$, R$_c$ and R$_d$ are as defined in Table 1.
Table 277: This table discloses the 169 compounds T 277.001 to T 277.169 of the formula Ia, wherein W is W$^{13}$, R is hydrogen, A is methyl, Q$^1$ is p-tolylsulfonylmethyl, Q$^2$ is hydrogen and R$_a$, R$_b$, R$_c$ and R$_d$ are as defined in Table 1.
Table 278: This table discloses the 169 compounds T 278.001 to T 278.169 of the formula Ia, wherein W is W$^{13}$, R is hydrogen, A is —CH$_2$CH═CH$_2$, Q$^1$ is p-tolylsulfonylmethyl, Q$^2$ is hydrogen and R$_a$, R$_b$, R$_c$ and R$_d$ are as defined in Table 1.
Table 279: This table discloses the 169 compounds T 279.001 to T 279.169 of the formula Ia, wherein W is W$^{13}$, R is hydrogen, A is —CH$_2$C≡CH, Q$^1$ is p-tolylsulfonylmethyl, Q$^2$ is hydrogen and R$_a$, R$_b$, R$_c$ and R$_d$ are as defined in Table 1.
Table 280: This table discloses the 169 compounds T 280.001 to T 280.169 of the formula Ia, wherein W is W$^{13}$, R is hydrogen, A is phenyl, Q$^1$ is p-tolylsulfonylmethyl, Q$^2$ is hydrogen and R$_a$, R$_b$, R$_c$ and R$_d$ are as defined in Table 1.
Table 281: This table discloses the 169 compounds T 281.001 to T 281.169 of the formula Ia, wherein W is W$^{14}$, A is hydrogen, Q$^1$ is p-tolylsulfonylmethyl, Q$^2$ is hydrogen and R$_a$, R$_b$, R$_c$ and R$_d$ are as defined in Table 1.
Table 282: This table discloses the 169 compounds T 282.001 to T 282.169 of the formula Ia, wherein W is W$^{14}$, A is methyl, Q$^1$ is p-tolylsulfonylmethyl, Q$^2$ is hydrogen and R$_a$, R$_b$, R$_c$ and R$_d$ are as defined in Table 1.
Table 283: This table discloses the 169 compounds T 283.001 to T 283.169 of the formula Ia, wherein W is W$^{14}$, A is —CH$_2$CH═CH$_2$, Q$^1$ is p-tolylsulfonylmethyl, Q$^2$ is hydrogen and R$_a$, R$_b$, R$_c$ and R$_d$ are as defined in Table 1.
Table 284: This table discloses the 169 compounds T 284.001 to T 284.169 of the formula Ia, wherein W is W$^{14}$, A is —CH$_2$C≡CH, Q$^1$ is p-tolylsulfonylmethyl, Q$^2$ is hydrogen and R$_a$, R$_b$, R$_c$ and R$_d$ are as defined in Table 1.
Table 285: This table discloses the 169 compounds T 285.001 to T 285.169 of the formula Ia, wherein W is W$^{14}$, A is phenyl, Q$^1$ is p-tolylsulfonylmethyl, Q$^2$ is hydrogen and R$_a$, R$_b$, R$_c$ and R$_d$ are as defined in Table 1.
Table 286: This table discloses the 169 compounds T 286.001 to T 286.169 of the formula Ia, wherein W is W$^1$, R is methyl, A is hydrogen, Q$^1$ is p-tolylsulfonylmethyl, Q$^2$ is hydrogen and R$_a$, R$_b$, R$_c$ and R$_d$ are as defined in Table 1.
Table 287: This table discloses the 169 compounds T 287.001 to T 287.169 of the formula Ia, wherein W is W$^1$, R is methyl, A is methyl, Q$^1$ is p-tolylsulfonylmethyl, Q$^2$ is hydrogen and R$_a$, R$_b$, R$_c$ and R$_d$ are as defined in Table 1.
Table 288: This table discloses the 169 compounds T 288.001 to T 288.169 of the formula Ia, wherein W is W$^1$, R is methyl, A is —CH$_2$CH═CH$_2$, Q$^1$ is p-tolylsulfonylmethyl, Q$^2$ is hydrogen and R$_a$, R$_b$, R$_c$ and R$_d$ are as defined in Table 1.
Table 289: This table discloses the 169 compounds T 289.001 to T 289.169 of the formula Ia, wherein W is W$^1$, R is methyl, A is —CH$_2$C≡CH, Q$^1$ is p-tolylsulfonylmethyl, Q$^2$ is hydrogen and R$_a$, R$_b$, R$_c$ and R$_d$ are as defined in Table 1.
Table 290: This table discloses the 169 compounds T 290.001 to T 290.169 of the formula Ia, wherein W is W$^1$, R is methyl, A is phenyl, Q$^1$ is p-tolylsulfonylmethyl, Q$^2$ is hydrogen and R$_a$, R$_b$, R$_c$ and R$_d$ are as defined in Table 1.
Table 291: This table discloses the 169 compounds T 291.001 to T 291.169 of the formula Ia, wherein W is W$^2$, R is methyl, A is hydrogen, Q$^1$ is p-tolylsulfonylmethyl, Q$^2$ is hydrogen and R$_a$, R$_b$, R$_c$ and R$_d$ are as defined in Table 1.
Table 292: This table discloses the 169 compounds T 292.001 to T 292.169 of the formula Ia, wherein W is W$^2$, R is methyl, A is methyl, Q$^1$ is p-tolylsulfonylmethyl, Q$^2$ is hydrogen and R$_a$, R$_b$, R$_c$ and R$_d$ are as defined in Table 1.
Table 293: This table discloses the 169 compounds T 293.001 to T 293.169 of the formula Ia, wherein W is W$^2$, R is methyl, A is —CH$_2$CH═CH$_2$, Q$^1$ is p-tolylsulfonylmethyl, Q$^2$ is hydrogen and R$_a$, R$_b$, R$_c$ and R$_d$ are as defined in Table 1.
Table 294: This table discloses the 169 compounds T 294.001 to T 294.169 of the formula Ia, wherein W is W$^2$, R is methyl, A is —CH$_2$C≡CH, Q$^1$ is p-tolylsulfonylmethyl, Q$^2$ is hydrogen and R$_a$, R$_b$, R$_c$ and R$_d$ are as defined in Table 1.
Table 295: This table discloses the 169 compounds T 295.001 to T 295.169 of the formula Ia, wherein W is W$^2$, R is methyl, A is phenyl, Q$^1$ is p-tolylsulfonylmethyl, Q$^2$ is hydrogen and R$_a$, R$_b$, R$_c$ and R$_d$ are as defined in Table 1.
Table 296: This table discloses the 169 compounds T 296.001 to T 296.169 of the formula Ia, wherein W is W$^2$, R is ethyl, A is hydrogen, Q$^1$ is p-tolylsulfonylmethyl, Q$^2$ is hydrogen and R$_a$, R$_b$, R$_c$ and R$_d$ are as defined in Table 1.
Table 297: This table discloses the 169 compounds T 297.001 to T 297.169 of the formula Ia, wherein W is W$^2$, R is ethyl, A is methyl, Q$^1$ is p-tolylsulfonylmethyl, Q$^2$ is hydrogen and R$_a$, R$_b$, R$_c$ and R$_d$ are as defined in Table 1.
Table 298: This table discloses the 169 compounds T 298.001 to T 298.169 of the formula Ia, wherein W is W$^2$, R is ethyl, A is —CH$_2$CH═CH$_2$, Q$^1$ is p-tolylsulfonylmethyl, Q$^2$ is hydrogen and R$_a$, R$_b$, R$_c$ and R$_d$ are as defined in Table 1.
Table 299: This table discloses the 169 compounds T 299.001 to T 299.169 of the formula Ia, wherein W is W$^2$, R is ethyl, A is —CH$_2$C≡CH, Q$^1$ is p-tolylsulfonylmethyl, Q$^2$ is hydrogen and R$_a$, R$_b$, R$_c$ and R$_d$ are as defined in Table 1.

Table 300: This table discloses the 169 compounds T 300.001 to T 300.169 of the formula Ia, wherein W is W$^2$, R is ethyl, A is phenyl, Q$^1$ is p-tolylsulfonylmethyl, Q$^2$ is hydrogen and R$_a$, R$_b$, R$_c$ and R$_d$ are as defined in Table 1.

The present application also makes available compounds of formula (II), wherein X, Y, Z, m, n (together corresponding to R$_a$, R$_b$, R$_c$, R$_{d\,from}$ formula Ia), A and W are as defined in each of Tables 1 to 300. Such compounds can also be made using teachings known in the art.

The present invention also makes available compounds of formula (I-I), wherein X, Y, Z, m, n (together corresponding to R$_a$, R$_b$, R$_c$, R$_d$ formula Ia), A, W, Q$^1$ as defined in each of Tables 1 to 300, and Q$^2$ formyl, methylcarbonyl, ethylcarbonyl, methoxycarbonyl or ethoxycarbonyl.

In each aspect and embodiment of the invention, "consisting essentially" and inflections thereof are a preferred embodiment of "comprising" and its inflections, and "consisting of" and inflections thereof are a preferred embodiment of "consisting essentially of" and its inflections.

The preferred (including more or most preferred, etc), particular, suitable, alternative and/or optional values of the substituents in, or other features of, the compounds or process steps/features described herein can be either taken alone or taken together with one or more of any other preferred, particular, suitable, alternative and/or optional features in any combination(s) thereof."

The following Examples serve to illustrate the invention. They do not limit the invention. Temperatures are given in degrees Celsius; mixing ratios of solvents (or diluents) are given in parts by volume.

PREPARATORY EXAMPLES

Example 1: Preparation of 4-(N-[2-(2,4-dichlorophenyl)acetyl]anilino)-1-methoxy-N-phenyl-piperidine-4-carboxamide (Compound P1.1)

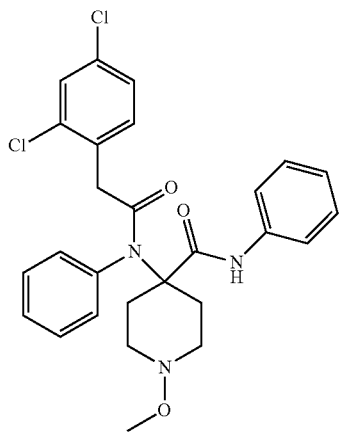 [SMILES: CON1CCC(C(=O)Nc2ccccc2)(N(C(=O)Cc2ccc(Cl)cc2Cl)c2ccccc2)CC1]

A round bottom flask, equipped with a magnetic stirrer bar, was charged with 1-methoxypiperidin-4-one (250.5 mg, 1.9 mmol), aniline (180.6 mg, 1.9 mmol) and methanol (0.5 mL). This was stirred at room temperature for 10 min, then 2-(2,4-dichlorophenyl)acetic acid (397.7 mg, 1.9 mmol) was added. This was stirred an additional 5 min, and isocyanobenzene (200.0 μL, 1.9 mmol) was added dropwise. An additional 0.5 mL of methanol was added to ensure stirring. The mixture was stirred for 2 days at room temperature. A precipitate had formed which was dissolved in dichloromethane. The mixture was evaporated under vacuum and the crude residue was taken up in dichloromethane and purified by flash column chromatography (DCM/EtOAc) to afford 4-(N-[2-(2,4-dichlorophenyl)acetyl]anilino)-1-methoxy-N-phenyl-piperidine-4-carboxamide (900.0 mg) as a light brown oil. $^1$H NMR (400 MHz, CHLOROFORM-d) δ 9.27 (br. s, 1H), 7.54 (app. d, J=7.7 Hz, 2H), 7.43 (br. s, 3H), 7.30-7.37 (m, 3H), 7.22-7.28 (m, 2H), 7.10-7.18 (m, 2H), 7.02-7.08 (m, 1H), 3.49 (s, 3H), 3.33 (br. s, 2H), 3.27 (br. s, 2H), 2.93-3.13 (br. m, 2H), 2.50-2.70 (br. m, 3H), 1.75-1.91 (br. m, 1H). $^{13}$C NMR (100 MHz, CHLOROFORM-d) δ 172.0, 169.3, 139.4, 138.0, 135.0, 133.6, 132.3, 130.2, 129.6 (2×C), 129.2 (2×C), 129.0 (3×C), 127.1 (2×C), 124.4, 120.5 (2×C), 65.2, 59.1, 54.1, 52.5, 41.6, 38.0, 33.6. LCMS, R$_t$ 1.20 min, (M−H)=510/512 and (M+H)=512/514.

Example 2: Preparation of 2-(2,4-dichlorophenyl)-1-hydroxy-8-methoxy-4-phenyl-4,8-diazaspiro[4.5]dec-1-en-3-one (Compound P2.1)

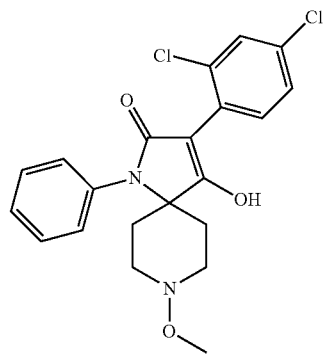 [SMILES: CON1CCC2(CC1)C(O)=C(c1ccc(Cl)cc1Cl)C(=O)N2c1ccccc1]

A microwave vial, equipped with a magnetic stirrer bar, was charged with 4-(N-[2-(2,4-dichlorophenyl)acetyl]anilino)-1-methoxy-N-phenyl-piperidine-4-carboxamide (200.0 mg, 0.39 mmol), potassium tert-butoxide (88.5 mg, 0.78 mmol) and DMF (2 mL). The vial was sealed and the mixture was heated to 130° C. for 45 min in the microwave. The reaction mixture was diluted with EtOAc (5 mL), and quenched with 1M HCl. The layers were separated and the organic layer was washed once more with 1M HCl. Combined aqueous layers were extracted twice with EtOAc. The solvents was removed under vacuum and the crude material was purified reversed phase HPLC to afford 2-(2,4-dichlorophenyl)-1-hydroxy-8-methoxy-4-phenyl-4,8-diazaspiro[4.5]dec-1-en-3-one (50 mg) as a white fluffy solid. $^1$H NMR (400 MHz, DMSO-d$_6$) δ 8.96 (s, 1H), 7.42-7.56 (m, 3H), 7.38-7.42 (m, 1H), 7.13-7.28 (m, 3H), 6.95-7.05 (m, 1H), 3.16-3.35 (m, 5H), 3.01 (br. s, 2H), 2.60 (br. s, 1H), 2.40 (br. s, 1H), 2.00 (br. s, 1H), 1.48 (br. s, 1H). $^{13}$C NMR (100 MHz, DMSO-d$_6$) δ 169.5, 138.8, 134.5, 133.3, 132.0, 130.6, 129.4, 128.2 (2×C), 126.9, 123.5, 121.3 (2×C), 58.4, 51.4 (2×C), 40.0, 31.6 (2×C) (C-3 and C-4 not observed). LCMS, R$_t$ 0.95-1.00 min, (M−H)=417/419, (M+H)=419/421.

Example 3: Preparation of 1-[benzyl-[2-(4-chloro-2,6-dimethyl-phenyl)acetyl]amino]-N-phenyl-cyclohexanecarboxamide (Compound P1.2)

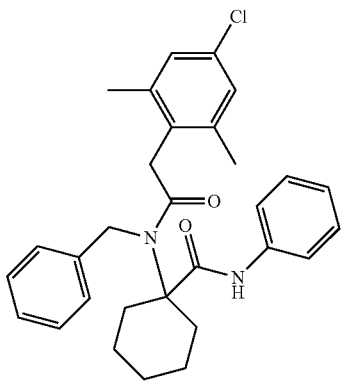 [SMILES: Cc1cc(Cl)cc(C)c1CC(=O)N(Cc1ccccc1)C1(C(=O)Nc2ccccc2)CCCCC1]

A round bottom flask, equipped with a magnetic stirrer bar, was charged with cyclohexanone (190.3 mg, 1.9 mmol), benzylamine (212.0 µL, 1.9 mmol) and methanol (0.5 mL). This was stirred at room temperature for 10 min, then 2-(4-chloro-2,6-dimethylphenyl)acetic acid (385.3 mg, 1.9 mmol) was added. This was stirred an additional 5 min, and isocyanobenzene (200.0 µL, 1.9 mmol) was added dropwise. An additional 0.5 mL of methanol was added to ensure stirring. The mixture was stirred for 2 days at room temperature. A precipitate had formed which was dissolved in dichloromethane. The mixture was evaporated under vacuum and the crude residue was taken up in dichloromethane and purified by flash column chromatography (DCM/EtOAc) to afford 1-[benzyl-[2-(4-chloro-2,6-di methyl-phenyl)acetyl]amino]-N-phenyl-cyclohexanecarboxamide (200.0 mg) as a yellow solid. $^1$H NMR (400 MHz, CHLOROFORM-d) δ 9.14 (s, 1H), 7.46 (d, J=7.7 Hz, 2H), 7.36-7.39 (m, 4H), 7.30 (t, J=7.9 Hz, 3H), 7.09 (t, J=7.3 Hz, 1H), 7.01 (s, 2H), 4.88 (s, 2H), 3.67 (s, 2H), 2.64-2.73 (m, 2H), 2.12 (s, 6H), 1.93-2.04 (m, 2H), 1.59-1.71 (m, 5H), 1.30-1.42 (m, 1H). $^{13}$C NMR (100 MHz, CHLOROFORM-d) δ 173.8, 170.8, 138.8 (2×C), 138.3, 138.2, 132.2, 131.3, 129.1 (2×C), 128.9 (2×C), 127.8 (2×C), 127.5, 125.9 (2×C), 123.9, 120.1 (2×C), 67.9, 48.8, 36.7, 33.2 (2×C), 25.3, 23.2 (2×C), 20.2 (2×C). LCMS, R$_t$ 1.28 min, (M−H)=487/489.

Example 4: Preparation of 2-(4-chloro-2,6-dimethyl-phenyl)-1-hydroxy-4-methyl-8-oxa-4-azaspiro[4.5]dec-1-en-3-one (Compound P2.3)

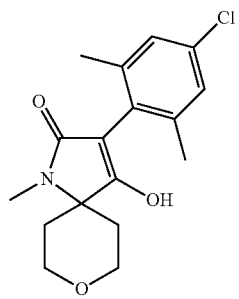 [SMILES: Cc1cc(Cl)cc(C)c1C1=C(O)C2(CCOCC2)N(C)C1=O]

A microwave vial, equipped with a magnetic stirrer bar, was charged with 4-[[2-(4-chloro-2,6-di methyl-phenyl)acetyl]-methyl-amino]-N-phenyl-tetra hydropyran-4-carboxamide (50.0 mg, 0.12 mmol), potassium tert-butoxide (27.3 mg, 0.24 mmol) and DMF (2 mL). The vial was sealed and the mixture was heated to 120° C. for 20 min in the microwave. The reaction mixture was diluted with EtOAc (5 mL), and quenched with 1M HCl. The layers were separated and the organic layer was washed once more with 1M HCl. Combined aqueous layers were extracted twice with EtOAc. The solvents was removed under vacuum and the crude material taken up in DCM then purified by FCC (DCM/EtOAc) to afford 2-(4-chloro-2,6-dimethyl-phenyl)-1-hydroxy-4-methyl-8-oxa-4-azaspiro[4.5]dec-1-en-3-one (22 mg) as a white solid. $^1$H NMR (400 MHz, DMSO-d$_6$) δ 11.04 (s, 1H), 7.14 (s, 2H), 3.95-4.04 (m, 2H), 3.85-3.92 (m, 2H), 2.79 (s, 3H), 2.02-2.14 (m, 8H), 1.57 (br. d, J=13.9 Hz, 2H). $^{13}$C NMR (100 MHz, DMSO-d$_6$) δ 173.8, 168.7, 140.6 (2×C), 131.6, 129.0, 126.3 (2×C), 101.8, 63.2 (2×C), 58.8, 31.4 (2×C), 23.4, 19.6 (2×C). LCMS, R$_t$ 0.80 min, (M−H)=320/322, (M+H)=322/324.

Example 5: Preparation of 1-[[2-(2,5-dimethylphenyl)acetyl]amino]-4-methoxy-N-phenyl-cyclohexanecarboxamide (Compound P1.6)

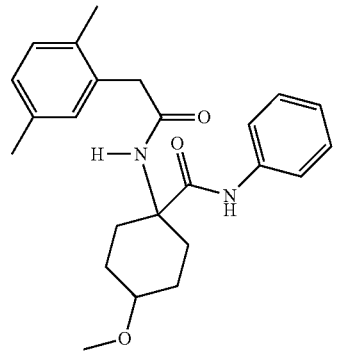 [SMILES: COC1CCC(NC(=O)Cc2cc(C)ccc2C)(C(=O)Nc2ccccc2)CC1]

A round bottom flask, equipped with a magnetic stirrer bar, was charged with 4-methoxycyclohexanone (234.2 mg, 1.8 mmol), ammonium carbonate (140.4 mg, 1.4 mmol) and 2,2,2-trifluoroethanol (4.0 mL). This was stirred at room temperature for 10 min, then cooled to 0° C. before 2-(2,5-dimethylphenyl)acetic acid (200.0 mg, 1.2 mmol) was added. This was stirred an additional 5 min, and isocyanobenzene (188.4 µL, 1.2 mmol) was added dropwise. The mixture was allowed to warm up to room temperature and stirred for 2 days. A precipitate had formed which was dissolved in dichloromethane. The mixture was evaporated under vacuum and the crude residue was taken up in dichloromethane and purified by flash column chromatography (DCM/EtOAc) to afford 1-[[2-(2,5-dimethylphenyl)acetyl]amino]-4-methoxy-N-phenyl-cyclohexanecarboxamide (384.2 mg) as a 1.5:1 mixture of diastereoisomers.

Major Diastereoisomer:
$^1$H NMR (400 MHz, CHLOROFORM-d) δ 9.79 (br. s, 1H), 7.53-7.60 (m, 2H), 7.32 (t, J=7.5 Hz, 2H), 7.05-7.17 (m, 3H), 7.02 (s, 1H), 5.40 (s, 1H), 3.64 (s, 2H), 3.30-3.33 (m, 1H), 3.28 (s, 3H), 2.33 (s, 3H), 2.28 (s, 3H), 2.08-2.15 (m, 2H), 1.89-2.02 (m, 2H), 1.73-1.81 (m, 2H), 1.26-1.39 (m, 2H). $^{13}$C NMR (CHLOROFORM-d) δ: $^{13}$C NMR (CHLOROFORM-d) d: 173.1, 171.3, 138.5, 136.5, 133.7, 132.6, 131.0, 130.9, 129.0, 128.9 (2×C), 123.9, 120.0 (2×C), 73.8, 61.1, 55.6, 42.4, 30.1 (2×C), 25.2 (2×C), 20.8, 19.0. LCMS, $R_t$ 0.99 min, (M−H)=393.

Minor Diastereoisomer:

$^1$H NMR (400 MHz, CHLOROFORM-d) δ 9.87 (br. s, 1H), 7.54 (dd, J=8.5 Hz, 1.0 Hz, 2H), 7.31-7.36 (m, 2H), 7.06-7.17 (m, 3H), 7.04 (s, 1H), 5.35 (s, 1H), 3.66 (s, 2H), 3.35 (s, 3H), 3.13-3.25 (m, 1H), 2.33 (s, 3H), 2.29 (s, 3H), 2.22-2.28 (m, 2H), 1.86-1.98 (m, 4H), 1.11-1.26 (m, 2H). $^{13}$C NMR (CHLOROFORM-d) δ: $^{13}$C NMR (CHLOROFORM-d) d: 173.2, 171.4, 138.4, 136.6, 133.7, 132.3, 131.1, 130.9, 129.1, 128.9 (2×C), 124.0, 120.0 (2×C), 76.9, 60.9, 55.8, 42.4, 29.8 (2×C), 26.6 (2×C), 20.8, 19.1. LCMS, $R_t$ 0.97 min, (M−H)=393.

Example 6: Preparation of 2-(2,5-dimethylphenyl)-1-hydroxy-8-methoxy-4-azaspiro[4.5]dec-1-en-3-one (Compound P2.4)

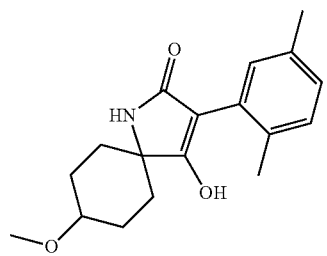 [SMILES: COC1CCC2(CC1)NC(=O)C(c1cc(C)ccc1C)=C2O]

A microwave vial, equipped with a magnetic stirrer bar, was charged with 1-[[2-(2,5-dimethylphenyl)acetyl]amino]-4-methoxy-N-phenyl-cyclohexanecarboxamide (1.5:1 mixture of diastereoisomers, 100.0 mg, 0.25 mmol), potassium tert-butoxide (57.0 mg, 0.50 mmol) and DMF (2 mL). The vial was sealed and the mixture was heated to 210° C. for 30 min in the microwave. The reaction mixture was diluted with EtOAc (5 mL), and quenched with 1M HCl. The layers were separated and the organic layer was washed once more with 1M HCl. Combined aqueous layers were extracted twice with EtOAc. The solvents was removed under vacuum and the crude material was purified by flash column chromatography (DCM/EtOAc) to afford 2-(2,5-dimethylphenyl)-1-hydroxy-8-methoxy-4-azaspiro[4.5]dec-1-en-3-one (40 mg) as a 1.5:1 mixture of trans/cis diastereoisomer.

$^1$H NMR (400 MHz, DMSO-d$_6$) δ 11.66 (s., 2H), 8.16 (s, 2H), 7.11 (d, J=8.0 Hz, 2H), 7.04 (dd, J=8.0, 1.5 Hz, 2H), 6.94 (d, J=1.5 Hz, 2H), 3.47-3.51 (m, 1H), 3.31 (s, 3H), 3.29 (s, 3H), 3.12-3.23 (m, 1H), 2.30 (s, 6H), 2.14 (s, 6H), 1.98-2.07 (m, 2H), 1.89-1.98 (m, 5H), 1.74-1.86 (m, 3H), 1.52-1.65 (m, 2H), 1.43-1.50 (m, 2H), 1.15-1.22 (m, 2H). LCMS, $R_t$ 0.77 min, (M−H)=300, (M+H)=302.

Example 7: Preparation of 4-allyl-2-(2,5-dimethylphenyl)-1-hydroxy-8-methoxy-4-azaspiro[4.5]dec-1-en-3-one (Compound P2.5)

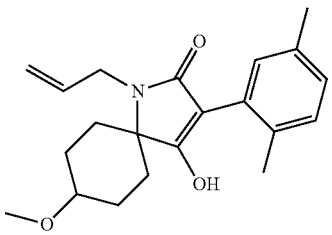 [SMILES: C=CCN1C(=O)C(c2cc(C)ccc2C)=C(O)C12CCC(OC)CC2]

A microwave vial, equipped with a magnetic stirrer bar, was charged with 1-[allyl-[2-(2,5-dimethyl phenyl)acetyl]amino]-4-methoxy-N-phenyl-cyclohexanecarboxamide (100.0 mg, 0.26 mmol), potassium tert-butoxide (52.0 mg, 0.52 mmol) and DMF (2 mL). The vial was sealed and the mixture was heated to 120° C. for 30 min in the microwave. The reaction mixture was diluted with EtOAc (5 mL), and quenched with 1M HCl. The layers were separated and the organic layer was washed once more with 1M HCl. Combined aqueous layers were extracted twice with EtOAc. The solvents was removed under vacuum and the crude material was purified by reversed phase HPLC to afford 4-allyl-2-(2,5-dimethylphenyl)-1-hydroxy-8-methoxy-4-azaspiro[4.5]dec-1-en-3-one (65 mg) as a 1:1 mixture of diastereoisomer as a white solid. $^1$H NMR (400 MHz, DMSO-d$_6$) δ 10.71 (br. s, 1H), 7.03 (d, J=8.0 Hz, 1H), 6.94 (dd, J=8.0, 1.5 Hz, 1H), 6.83 (br. s, 1H), 5.65-5.82 (m, 1H), 5.06 (dd, J=17.0, 1.5 Hz, 1H), 4.97 (dd, J=10.5, 1.5 Hz, 1H), 3.80 (d, J=5.0 Hz, 2H), 3.18 (s, 4H), 2.19 (s, 3H), 2.02 (s, 3H), 1.78-1.92 (m, 6H), 1.55 (app. d, J=6.5 Hz, 2H). $^{13}$C NMR (100 MHz, DMSO-d$_6$) δ: 174.1, 169.2, 136.1, 134.5, 133.8, 131.8, 130.3, 129.4, 127.8, 115.2, 103.7, 77.1, 61.5, 55.1, 40.1, 30.7, 27.0 (3×C), 20.5, 19.0. LCMS, $R_t$ 0.95-1.09 min, (M−H)=340, (M+H)=342.

$^1$H NMR (400 MHz, DMSO-d$_6$) δ 10.65 (br. s., 1H), 7.02 (d, J=8.0 Hz, 1H), 6.93 (dd, J=8.0, 1.5 Hz, 1H), 6.83 (br. s, 1H), 5.67-5.81 (m, 1H), 5.02 (dd, J=17.0, 1.5 Hz, 1H), 4.98 (dd, J=10.5, 1.5 Hz, 1H), 3.80 (d, J=5.0 Hz, 2H), 3.35 (br. s, 1H), 3.18 (s, 3H), 2.19 (s, 3H), 1.91-2.06 (m, 7H), 1.73-1.84 (m, 2H), 1.28-1.45 (m, 2H). $^{13}$C NMR (100 MHz, DMSO-d$_6$) δ: 174.1, 169.2, 136.0, 134.5, 133.8, 131.7, 130.3, 129.4, 127.8, 115.0, 103.7, 73.0, 61.4, 55.0, 40.5, 27.5, 25.5 (3×C), 20.4, 19.0. LCMS, $R_t$ 0.95-1.09 min, (M−H)=340, (M+H)=342.

Example 8: Preparation of 4-benzyl-2-(2,5-dimethylphenyl)-1-hydroxy-8-methoxy-4-azaspiro[4.5]dec-1-en-3-one (Compound P2.6)

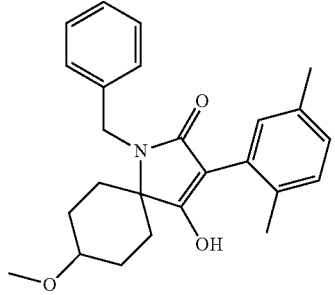 [SMILES: COC1CCC2(CC1)C(O)=C(c1cc(C)ccc1C)C(=O)N2Cc1ccccc1]

A microwave vial, equipped with a magnetic stirrer bar, was charged with 1-[benzyl-[2-(2,5-dimethylphenyl)acetyl]amino]-4-methoxy-N-phenyl-cyclohexanecarboxamide (200.0 mg, 0.41 mmol), potassium tert-butoxide (93.0 mg, 0.82 mmol) and DMF (4 mL). The vial was sealed and the mixture was heated to 130° C. for 45 min in the microwave. The reaction mixture was diluted with EtOAc (5 mL), and quenched with 1M HCl. The layers were separated and the organic layer was washed once more with 1M HCl. Combined aqueous layers were extracted twice with EtOAc. The solvents was removed under vacuum and the crude material was purified by reversed phase HPLC to afford 4-benzyl-2-(2,5-dimethylphenyl)-1-hydroxy-8-methoxy-4-azaspiro[4.5]dec-1-en-3-one (35 mg) as a 1:1 mixture of diastereoisomers as a white solid. $^1$H NMR (400 MHz, DMSO-d$_6$) δ 10.77 (br. s., 1H), 7.16-7.26 (m, 4H), 7.10-7.15 (m, 1H), 7.05 (d, J=7.5 Hz, 1H), 6.93-6.99 (m, 1H), 6.89 (s, 1H), 4.44 (s, 2H), 3.10-3.18 (m, 4H), 2.21 (s, 3H), 2.07 (s, 3H), 1.79 (br. s, 6H), 1.46-1.52 (m, 2H). $^{13}$C NMR (100 MHz, DMSO-$d_6$) δ: 174.8, 169.9, 140.2, 134.5, 133.9, 131.8, 129.4, 128.3, 128.1 (2×C), 127.8, 126.7 (2×C), 126.4, 103.7, 77.0, 61.8, 55.1, 40.8, 30.9, 27.0 (3×C), 20.5, 19.1. LCMS, rt 1.0-1.5, (M–H)=390, (M+H)=392. LCMS, $R_t$ 1.0-1.5 min, (M–H)=390, (M+H)=392.

$^1$H NMR (400 MHz, DMSO-$d_6$) δ 10.84 (br. s., 1H), 7.20-7.26 (m, 2H), 7.10-7.19 (m, 3H), 7.04 (d, J=7.5 Hz, 1H), 6.95 (d, J=7.5 Hz, 1H), 6.89 (s, 1H), 4.43 (s, 2H), 3.29 (br. s, 1H), 3.12 (s, 3H), 2.20 (s, 3H), 2.07 (s, 3H), 1.80-2.02 (m, 4H), 1.60-1.72 (m, 2H), 1.34 (d, J=12.5 Hz, 2H). $^{13}$C NMR (100 MHz, DMSO-$d_6$) δ: 174.8, 169.9, 140.0, 134.5, 133.8, 131.8, 130.5, 129.4, 128.1 (2×C), 127.8, 126.6 (2×C), 126.4, 103.8, 73.0, 61.7, 55.0, 41.3, 27.7, 25.5 (3×C), 20.5, 19.1. LCMS, $R_t$ 1.0-1.5 min, (M–H)=390, (M+H)=392.

Example 9: Preparation of 4-[[2-(4-chloro-2,6-dimethyl-phenyl)acetyl]-methyl-amino]-1-methoxy-N-phenyl-piperidine-4-carboxamide (Compound P1.9)

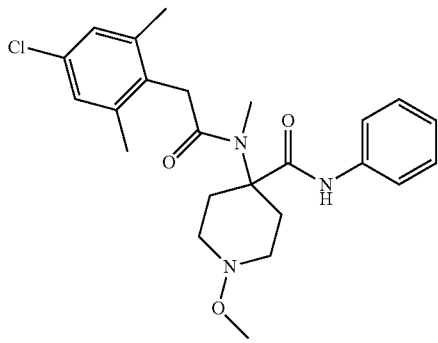 [SMILES: CON1CCC(C(=O)Nc2ccccc2)(N(C)C(=O)Cc2c(C)cc(Cl)cc2C)CC1]

Solution A: A round bottom flask, equipped with a magnetic stirrer bar, was charged with 1-methoxypiperidin-4-one (5.7 g, 44 mmol) and methanamine (33% in ethanol, 4.2 g, 45 mmol). This was stirred at room temperature for 4 h, then methanamine (33% in ethanol, 0.8 g, 9 mmol) was added. This was stirred at room temperature for 1 h, then methanamine (33% in ethanol, 0.8 g, 9 mmol) was added.

Another round bottom flask, equipped with a magnetic stirrer bar, was charged with 2-(4-chloro-2,6-dimethylphenyl)acetic acid (4 g, 20 mmol) in methanol (48 mL). 5.8 g of the above prepared solution A was added to this in one portion. Then isocyanobenzene (2.3 g, 22 mmol) was added in one portion. The mixture was heated to 55° C. and stirred for 2 h at 55° C., then at room temperature overnight. The mixture was heated to 55° C. and stirred for 1.75 h, then 0.9 g of the above prepared solution A were added to this in one portion. The reaction mixture was stirred at 55° C. for 1.5 h, then heated under reflux for 4 h. The reaction mixture was diluted with dichloromethane (180 mL) and added to sat. aq. NaHCO3 at 0° C. The phases were separated and the organic phase washed with water (2×90 mL), dried over Na2SO4 and evaporated to dryness to afford crude 4-[[2-(4-chloro-2,6-dimethyl-phenyl)acetyl]-methyl-amino]-1-methoxy-N-phenyl-piperidine-4-carboxamide (6.9 g) as an off-white solid.

1H NMR (400 MHz, DMSO-d6) δ ppm 2.08 (s, 6H) 2.20-2.40 (m, 2H), 2.82 (m, 2H), 3.16-3.27 (m, 4H) 3.32 (s, 3H), 3.42 (s, 3H), 3.70 (br. s., 2H), 6.97-7.00 (m, 3H), 7.24 (m, 2H), 7.48-7.50 (m, 2H), 9.20 (br. s., 1H). LCMS, Rt 0.99 min, (M–H)=442, (M+H)=444.

Example 10: Preparation of 2-(4-chloro-2,6-dimethyl-phenyl)-1-hydroxy-8-methoxy-4-methyl-4,8-diazaspiro[4.5]dec-1-en-3-one (Compound P2.7)

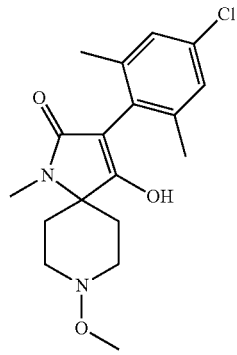 [SMILES: CON1CCC2(CC1)C(O)=C(c1c(C)cc(Cl)cc1C)C(=O)N2C]

In a microwave vial, equipped with a magnetic stirrer bar, was dissolved 4-[[2-(4-chloro-2,6-dimethyl-phenyl)acetyl]-methyl-amino]-1-methoxy-N-phenyl-piperidine-4-carboxamide (50 mg, 0.11 mmol) in THF (1 mL). Ethylformate (82 mg, 0.22 mmol) and potassium tert-butoxide (1M in THF, 0.22 mL, 0.22 mmol) were then successively added. The vial was sealed and heated at 120° C. for 15 minutes. The reaction mixture was concentrated in vacuo to afford a white solid. $^1$H NMR analysis of the crude mixture (against 1,3,5-trimethoxybenzene as internal standard) indicated 2-(4-chloro-2,6-dimethyl-phenyl)-1-hydroxy-8-methoxy-4-methyl-4,8-diazaspiro[4.5]dec-1-en-3-one was formed in about 73% yield.

$^1$H NMR (400 MHz, DMSO-$d_6$) δ ppm 1.3-1.7 (br. m, 2H) 2.06 (s, 6H) 2.1-2.3 (br. m, 2H) 2.6-2.9 (br. m, 3H) 3.0-3.3 (br. m, 3H) 3.45 (s, 3H) 7.13 (s, 2H), 11.0 (br. s, 1H).

Example 11: Preparation of 2-(4-chloro-2,6-dimethyl-phenyl)-1-hydroxy-8-methoxy-4-methyl-4,8-diazaspiro[4.5]dec-1-en-3-one (Compound P2.7)

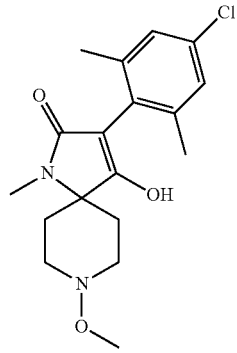 [SMILES: CON1CCC2(CC1)C(O)=C(c1c(C)cc(Cl)cc1C)C(=O)N2C]

In a microwave vial, equipped with a magnetic stirrer bar, were dissolved 4-[[2-(4-chloro-2,6-dimethyl-phenyl)acetyl]-methyl-amino]-1-methoxy-N-phenyl-piperidine-4-carboxamide (228 mg, 0.51 mmol) and triethylamine (0.22 mL, 1.6 mmol) in DMF (4.5 mL). At room temperature, methylchloroformate (0.060 mL, 0.77 mmol) was then added dropwise followed by potassium tert-butoxide (1M in THF, 1 mL, 1.02 mmol). The vial was sealed and heated at 120° C. for 30 min. The reaction mixture was cooled to room temperature and another portion of potassium tert-butoxide (1M in THF, 1 mL, 1.02 mmol) was added and the mixture was heated for another 15 minutes. LCMS analysis then indicated complete conversion and 2-(4-chloro-2,6-dimethyl-phenyl)-1-hydroxy-8-methoxy-4-methyl-4,8-diazaspiro[4.5]dec-1-en-3-one was observed as indicated by LCMS analysis.

Example 12: Preparation of 2-(4-chloro-2,6-dimethyl-phenyl)-1-hydroxy-8-methoxy-4-methyl-4,8-diazaspiro[4.5]dec-1-en-3-one (Compound P2.7)

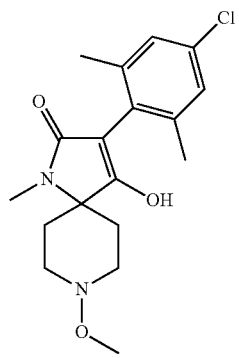 [SMILES: CON1CCC2(CC1)C(O)=C(c1c(C)cc(Cl)cc1C)C(=O)N2C]

In a microwave vial, equipped with a magnetic stirrer bar, was dissolved 4-[[2-(4-chloro-2,6-dimethyl-phenyl)acetyl]-methyl-amino]-1-methoxy-N-phenyl-piperidine-4-carboxamide (50 mg, 0.11 mmol) in DMF (1 mL). Butylformate (23 mg, 0.22 mmol) and potassium tert-butoxide (1M in THF, 0.22 mL, 0.22 mmol) were then successively added. The vial was sealed and heated at 120° C. for 6 h. The reaction mixture was concentrated in vacuo to afford a white solid. $^1$H NMR analysis of the crude mixture (against 1,3,5-trimethoxybenzene as internal standard) indicated 2-(4-chloro-2,6-dimethyl-phenyl)-1-hydroxy-8-methoxy-4-methyl-4,8-diazaspiro[4.5]dec-1-en-3-one was formed in about 84% yield.

Example 13: Preparation of 2-(4-chloro-2,6-dimethyl-phenyl)-1-hydroxy-8-methoxy-4-methyl-4,8-diazaspiro[4.5]dec-1-en-3-one (Compound P2.7)

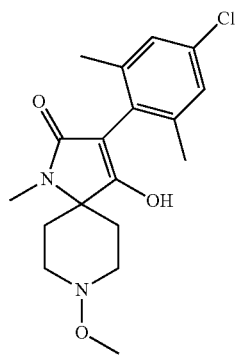

In a microwave vial, equipped with a magnetic stirrer bar, was suspended 4-[[2-(4-chloro-2,6-dimethyl-phenyl)acetyl]-methyl-amino]-1-methoxy-N-phenyl-piperidine-4-carboxamide (0.45 g, 1.02 mmol) in dimethylcarbonate (3 mL). Triethylamine (0.43 mL, 3.0 mmol) and potassium tert-butoxide (1M in THF, 2.0 mL, 2.0 mmol) were then successively added. The vial was sealed and heated at 120° C. for 30 minutes. 2-(4-chloro-2,6-dimethyl-phenyl)-1-hydroxy-8-methoxy-4-methyl-4,8-diazaspiro[4.5]dec-1-en-3-one was observed as indicated by LCMS analysis, conversion of the starting material was about 50%.

Example 14: Preparation of 4-[[2-(4-chloro-2,6-dimethyl-phenyl)acetyl]-methyl-amino]-1-methoxy-N-(p-tolyl)piperidine-4-carboxamide (Compound P1.10)

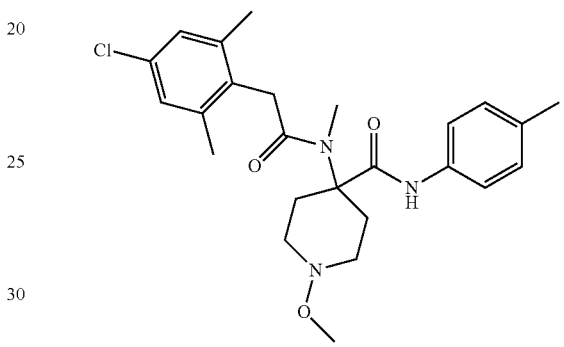

A round bottom flask, equipped with a magnetic stirrer bar, was charged with 2-(4-chloro-2,6-dimethylphenyl)acetic acid (4.5 g, 23 mmol) and 1-isocyano-4-methyl-benzene (2.9 g, 25 mmol) in methanol (60 mL). The reaction mixture was heated to 55° C. In parallel, 1-methoxypiperidin-4-one (3.4 g, 26 mmol) and methanamine (33% in ethanol, 2.8 g, 30 mmol) were added dropwise to this over 30 min. The reaction mixture was stirred at 55° C. for 23 h, then cooled to room temperature. The reaction mixture was diluted with dichloromethane (360 mL) and added to saturated aqueous NaHCO$_3$ (160 mL) at 0° C. The phases were separated and the organic phase washed with water (2×100 mL), dried over Na$_2$SO$_4$ and evaporated to dryness to afford crude 4-[[2-(4-chloro-2,6-dimethyl-phenyl)acetyl]-methyl-amino]-1-methoxy-N-(p-toluyl)piperidine-4-carboxamide (8.8 g) as an off-white solid. LCMS, R$_t$ 1.88 min, (M−H)=456, (M+H)=458.

Compounds of the formula (I) from Table P1 and compounds of the formula (II) from Table P2 below can be prepared by analogous procedures. Either one of the following LC-MS methods was used to characterize the compounds:

Method A

Spectra were recorded on a ZQ Mass Spectrometer from Waters (Single quadrupole mass spectrometer) equipped with an electrospray source (Polarity: positive or negative ions, Capillary: 3.00 kV, Cone range: 30-60 V, Extractor: 2.00 V, Source Temperature: 100° C., Desolvation Temperature: 250° C., Cone Gas Flow: 50 L/Hr, Desolvation Gas Flow: 400 L/Hr, Mass range: 100 to 900 Da) and an Agilent 1100 LC (Solvent degasser, binary pump, heated column compartment and diode-array detector. Column: Phenomenex Gemini C18, 3 μm, 30×3 mm, Temp: 60° C., DAD Wavelength range (nm): 210 to 500, Solvent Gradient:

A=water+5% MeOH+0.05% HCOOH, B=Acetonitrile+0.05% HCOOH: gradient: 0 min 0% B; 2-2.8 min 100% B; 2.9-3 min 0%. Flow (ml/min) 1.7

Method B

Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 μm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH: gradient: gradient: 0 min 0% B, 100% A; 1.2-1.5 min 100% B; Flow (ml/min) 0.85

Method C

MS Detector: LTQ Velos Orbitrap high resolution Mass Spectrometer from Thermo Scientific
Ionisation: APCI positive/Vaporizer Temp. 350° C., Capillary Temp. 275° C.
Detection: full scan 130-1500 Da/resolution 30000
LC: HTS-xt PAL Autosampler, Thermo Accela Pump 1250, Thermo Accela PDA Detector
Column: Macherey-Nagel Nucleodur 100 C18, 250×4.6 mm, 3 μm particle size
UV Wavelength: 230 nm
Gradient: (Solvent A=Acetonitrile/Solvent B=Trifluoroacetic acid 0.1% in Water)

| Time (min) | A % | B % | Flow (ml/min) |
|---|---|---|---|
| 00.00 | 30.0 | 70.0 | 0.8 |
| 25.00 | 100.0 | 00.0 | 0.8 |
| 30.00 | 100.0 | 00.0 | 0.8 |
| 31.00 | 30.0 | 70.0 | 0.8 |
| 40.00 | 30.0 | 70.0 | 0.8 |

The characteristic values obtained for each compound were the retention time ("$R_t$", recorded in minutes) and the molecular ion as listed in Tables P1 and P2.

Method D

Spectra were recorded on a SQD Mass Spectrometer from Waters (Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 250° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Phenomenex Gemini C18, 3 μm, 30×2 mm, Temp: 60° C., DAD Wavelength range (nm): 210 to 500, Solvent Gradient: A=water+5% MeOH+0.05% HCOOH, B=Acetonitrile+0.05% HCOOH: gradient: gradient: 0 min 0% B, 100% A; 1.2-1.5 min 100% B; Flow (ml/min) 0.85.

TABLE P1

Physical data of compounds of formula I

| Comp. No. | Structure | Melting Point | MS/NMR |
|---|---|---|---|
| P1.1 | 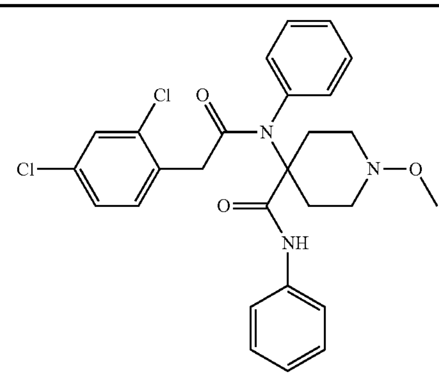 | gum | LC/MS: 512/514 (M + H)$^+$ <br> $R_t$ = 1.20 min <br> (Method B) |
| P1.2 | 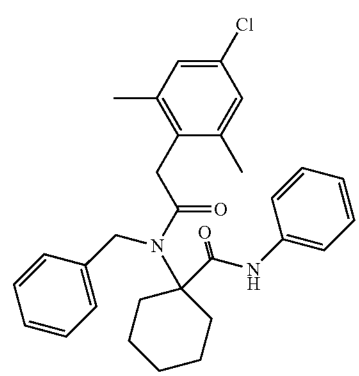 [SMILES: Cc1cc(Cl)cc(C)c1CC(=O)N(Cc1ccccc1)C1(C(=O)Nc2ccccc2)CCCCC1] | solid | LC/MS: 487/489 (M − H)$^-$ <br> $R_t$ = 1.28 min <br> (Method B) |

TABLE P1-continued

Physical data of compounds of formula I

| Comp. No. | Structure | Melting Point | MS/NMR |
|---|---|---|---|
| P1.3 | 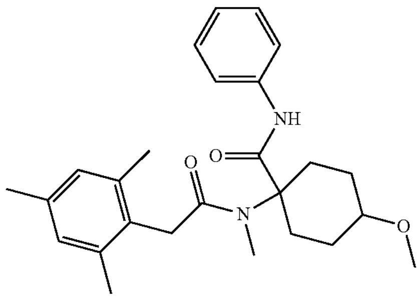 | gum | $^1$H NMR (400 MHz, CDCl$_3$) δ 9.27-9.97 (m, 1H), 7.48 (br. d, J = 7.7 Hz, 2H), 7.30 (br. t, J = 8.1 Hz, 2H), 7.04-7.12 (m, 1H), 6.91 (s, 2H), 3.73 (br. s, 2H), 3.54 (s, 3H), 3.28 (br. s, 3H), 3.14 (br. s, 3H), 2.58-2.96 (m, 3H), 2.29 (s, 3H), 2.23 (br. s, 6H), 1.97-2.18 (m, 2H).<br>LC/MS: 422 (M − H)$^−$<br>R$_t$ = 1.03 min<br>(Method B) |
| P1.4 | 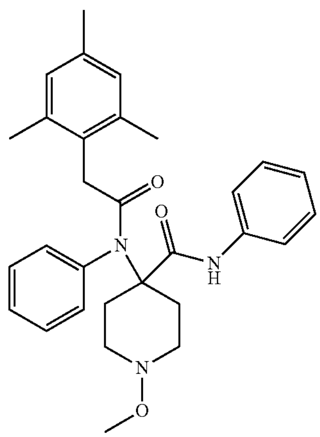 [SMILES: CON1CCC(C(=O)Nc2ccccc2)(N(C(=O)Cc2c(C)cc(C)cc2C)c2ccccc2)CC1] | solid | $^1$H NMR (400 MHz, CDCl$_3$) δ 9.60 (br. s., 1H), 7.47-7.56 (m, 2H), 7.38-7.47 (m, 4H), 7.27-7.36 (m, 3H), 7.05-7.15 (m, 1H), 6.81 (s, 2H), 3.48 (s, 3H), 3.14-3.32 (m, 4H), 2.90-3.14 (m, 2H), 2.50-2.85 (m, 3H), 2.22 (s, 3H), 2.09 (s, 6H), 1.77-1.92 (m, 1H).<br>LC/MS: 486 (M + H)$^+$<br>R$_t$ = 1.20 min<br>(Method B) |
| P1.5 | 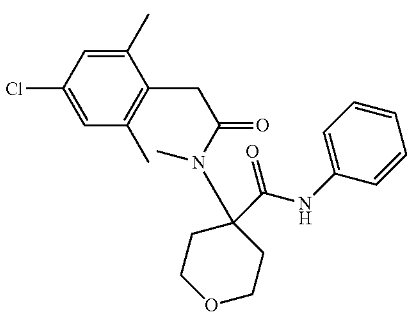 [SMILES: Cc1cc(Cl)cc(C)c1CC(=O)N(C)C1(C(=O)Nc2ccccc2)CCOCC1] | solid | $^1$H NMR (400 MHz, CDCl$_3$) δ 9.52 (br. s, 1H), 7.47-7.51 (m, 2H), 7.28-7.35 (m, 2H), 7.09-7.13 (m, 1H), 7.08 (s, 2H), 3.78-3.86 (m, 2H), 3.72-3.77 (m, 2H), 3.71 (s, 2H), 3.14 (s, 3H), 2.65-2.74 (m, 2H), 2.24 (s, 6H), 2.15-2.23 (m, 2H).<br>LC/MS: 413/415 (M − H)$^−$<br>R$_t$ = 1.01 min<br>(Method B) |
| P1.6 | 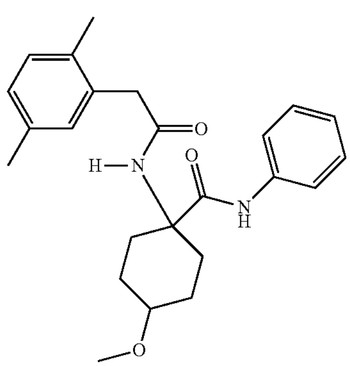 [SMILES: COC1CCC(NC(=O)Cc2cc(C)ccc2C)(C(=O)Nc2ccccc2)CC1] | oil | 1.5:1 mixture of diastereomers:<br>Major: LC/MS: 393 (M − H)$^−$<br>R$_t$ = 0.99 min<br>Minor: LC/MS: 393 (M − H)$^−$<br>R$_t$ = 0.97 min<br>(Method B) |

TABLE P1-continued

Physical data of compounds of formula I

| Comp. No. | Structure | Melting Point | MS/NMR |
|---|---|---|---|
| P1.7 | 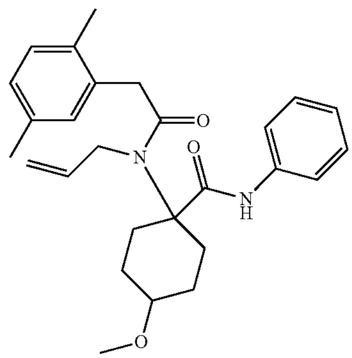 [SMILES: C=CCN(C(=O)Cc1cc(C)ccc1C)C1(C(=O)Nc2ccccc2)CCC(OC)CC1] | foam | 1:1 mixture of diastereomers: $^1$H NMR (400 MHz, CDCl$_3$) δ 9.15 (br. s, 1H), 9.12 (br. s, 1H), 7.45-7.60 (m, 4H), 7.30 (t, J = 7.5 Hz, 4H), 7.04-7.11 (m, 4H), 6.95-7.00 (m, 2H), 6.87-6.92 (m, 2H), 5.80-6.03 (m, 2H), 5.20-5.40 (m, 4H), 4.03-4.10 (m, 4H), 3.69 (s, 2H), 3.72 (s, 2H), 3.35-3.39 (m, 1H), 3.35 (s, 3H), 3.33 (s, 3H), 3.23-3.32 (m, 1H), 2.80-2.90 (m, 2H), 2.36-2.47 (m, 2H), 2.25-2.36 (m, 3H), 2.20 (s, 3H), 2.19 (s, 3H), 2.18 (s, 3H), 2.17 (s, 3H), 1.86-2.02 (m, 5H), 1.61-1.76 (m, 4H). LC/MS: 433 (M − H)$^-$ R$_t$ = 1.10 and 1.13 min (Method B) |
| P1.8 | 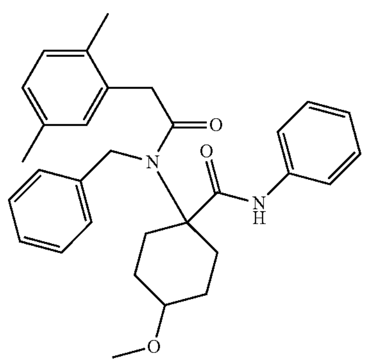 [SMILES: COC1CCC(C(=O)Nc2ccccc2)(N(Cc2ccccc2)C(=O)Cc2cc(C)ccc2C)CC1] | solid | 1:1 mixture of diastereomers: $^1$H NMR (400 MHz, CDCl$_3$) δ 9.09 (s, 1H), 9.04 (s, 1H), 7.42-7.53 (m, 4H), 7.26-7.41 (m, 14H), 7.04-7.10 (m, 2H), 6.98-7.03 (m, 2H), 6.91-6.97 (m, 2H), 6.89 (br. s, 1H), 6.85 (br. s, 1H), 4.67 (s, 2H), 4.66 (s, 2H), 3.68 (s, 2H), 3.63 (s, 2H), 3.56-3.62 (m, 1H), 3.40 (s, 3H), 3.32-3.37 (m, 1H), 3.27 (s, 3H), 2.91-3.00 (m, 2H), 2.33-2.44 (m, 2H), 2.21-2.30 (m, 4H), 2.18 (s, 3H), 2.14 (s, 3H), 2.05 (s, 3H), 2.04 (s, 3H), 1.87-1.98 (m, 4H), 1.69-1.80 (m, 4H). LC/MS: 485 (M + H)$^+$ 483 (M − H)$^-$ R$_t$ = 1.17 and 1.20 min (Method B) |
| P1.9 | 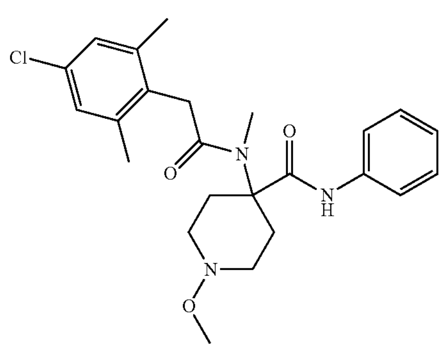 [SMILES: CON1CCC(C(=O)Nc2ccccc2)(N(C)C(=O)Cc2c(C)cc(Cl)cc2C)CC1] | solid | LC/MS: 444 (M + H)$^+$ 442 (M − H)$^-$ R$_t$ = 0.99 min (Method D) |
| P1.10 | 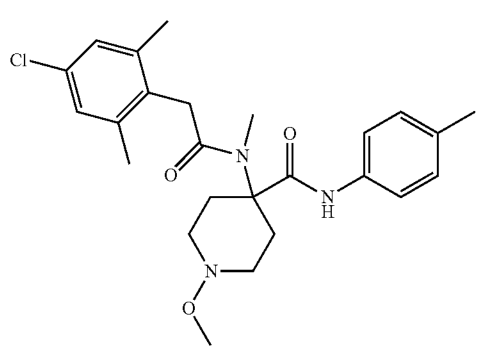 [SMILES: CON1CCC(C(=O)Nc2ccc(C)cc2)(N(C)C(=O)Cc2c(C)cc(Cl)cc2C)CC1] | solid | LC/MS: 351, 458 (M + H)$^+$ 456 (M − H)$^-$ R$_t$ = 1.88 min (Method A) |

TABLE P1-continued

Physical data of compounds of formula I

| Comp. No. | Structure | Melting Point | MS/NMR |
|---|---|---|---|
| P1.11 | 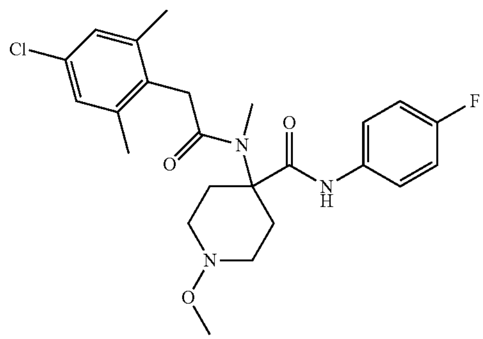 | solid | LC/MS: 351, 462 (M + H)+<br>460 (M − H)−<br>R$_t$ = 1.82 min<br>(Method A) |
| P1.12 | 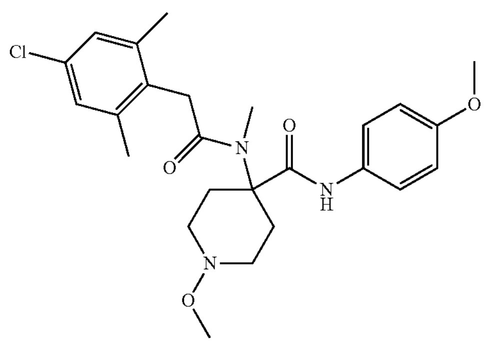 | solid | LC/MS: 472 (M − H)−<br>R$_t$ = 1.78 min<br>(Method A) |
| P1.13 | 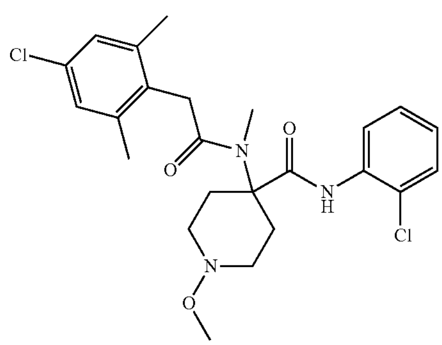 [SMILES: CON1CCC(C(=O)Nc2ccccc2Cl)(N(C)C(=O)Cc2c(C)cc(Cl)cc2C)CC1] | solid | LC/MS: 478 (M + H)+,<br>476 (M − H)−<br>R$_t$ = 1.05 min<br>(Method D) |
| P1.14 | 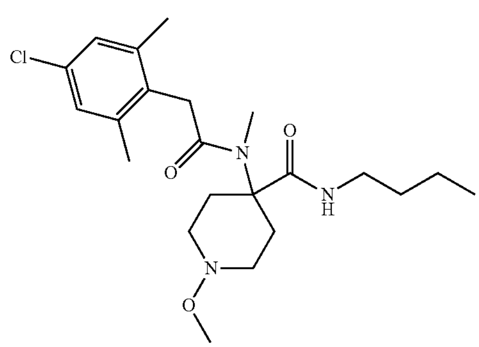 [SMILES: CCCCNC(=O)C1(N(C)C(=O)Cc2c(C)cc(Cl)cc2C)CCN(OC)CC1] | solid | LC/MS: 424/426 (M + H)+<br>R$_t$ = 13.44 min<br>(Method C) |

TABLE P1-continued

Physical data of compounds of formula I

| Comp. No. | Structure | Melting Point | MS/NMR |
|---|---|---|---|
| P1.15 | 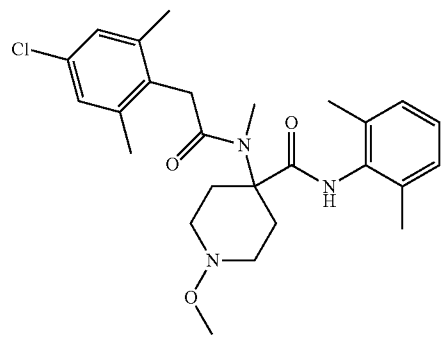 [SMILES: CON1CCC(C(=O)Nc2c(C)cccc2C)(N(C)C(=O)Cc2c(C)cc(Cl)cc2C)CC1] | solid | LC/MS: 472/474 (M + H)+<br>R$_t$ = 16.40 min<br>(Method C) |
| P1.16 | 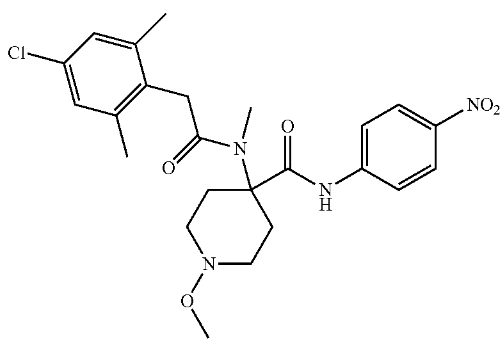 [SMILES: CON1CCC(C(=O)Nc2ccc([N+](=O)[O-])cc2)(N(C)C(=O)Cc2c(C)cc(Cl)cc2C)CC1] | solid | LC/MS: 489/491 (M + H)+<br>R$_t$ = 16.11 min<br>(Method C) |
| P1.17 | 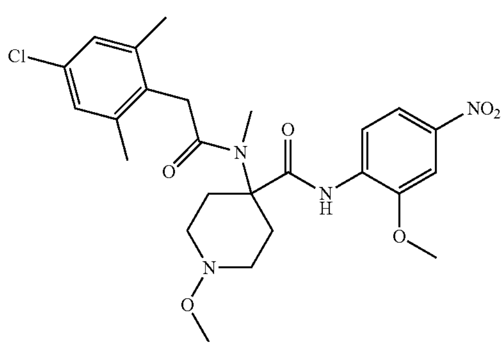 [SMILES: COc1cc([N+](=O)[O-])ccc1NC(=O)C1(N(C)C(=O)Cc2c(C)cc(Cl)cc2C)CCN(OC)CC1] | solid | LC/MS: 519/521 (M + H)+<br>R$_t$ = 18.65 min<br>(Method C) |
| P1.18 | 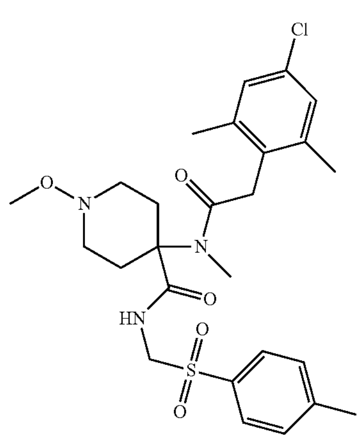 | solid | LC/MS: 536/538 (M + H)+<br>R$_t$ = 14.35 min<br>(Method C) |

TABLE P2

Physical data of compounds of formula II

| Compound No. | Structures | Melting Point | MS/NMR |
|---|---|---|---|
| P2.1 | 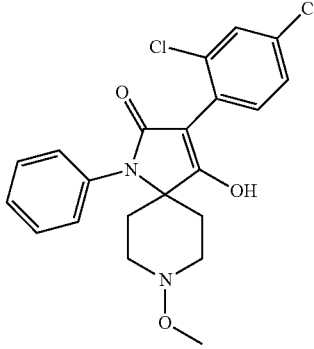 | solid | LC/MS: 419/421 (M + H)+ R$_t$ = 0.95-1.00 min (method B) |
| P2.2 | 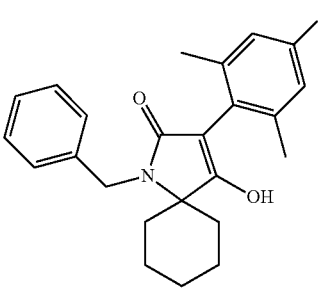 | solid | $^1$H NMR (400 MHz, DMSO-d$_6$) δ 10.87 (s, 1H), 7.25-7.34 (m, 5H), 7.17 (s, 2H), 4.56 (s, 2H), 2.16 (s, 6H), 1.84-1.95 (m, 2H), 1.70-1.82 (m, 2H), 1.53-1.62 (m, 5H), 1.12-1.29 (m, 1H). LC/MS: 394/396 (M − H)− R$_t$ = 1.15 min (method B) |
| P2.3 | 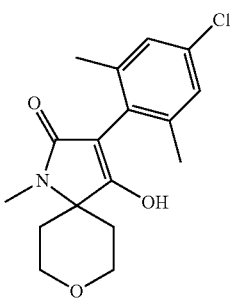 [SMILES: Cc1cc(Cl)cc(C)c1C1=C(O)C2(CCOCC2)N(C)C1=O] | solid | LC/MS: 322/324 (M + H)+ R$_t$ = 0.80 min (method B) |
| P2.4 | 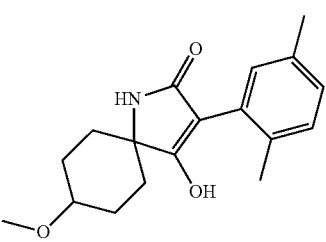 [SMILES: COC1CCC2(CC1)NC(=O)C(c1cc(C)ccc1C)=C2O] | | 1.5:1 mixture of trans/cis diastereomers: LC/MS: 302 (M + H)+, 300 (M − H)− R$_t$ = 0.77 min (method B) |
| P2.5 | 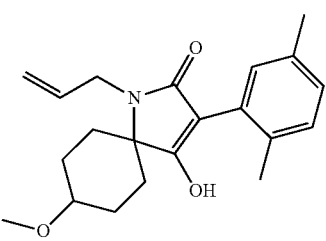 [SMILES: C=CCN1C(=O)C(c2cc(C)ccc2C)=C(O)C12CCC(OC)CC2] | solid | 1:1 mixture of diastereomers: LC/MS: 342 (M + H)+ R$_t$ = 0.95-1.00 min (method B) |

TABLE P2-continued

Physical data of compounds of formula II

| Compound No. | Structures | Melting Point | MS/NMR |
|---|---|---|---|
| P2.6 | 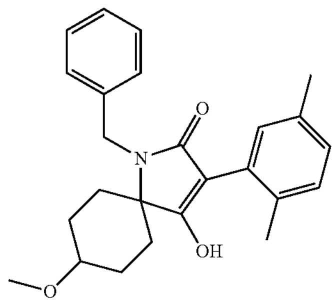 [SMILES: COC1CCC2(CC1)C(O)=C(c1cc(C)ccc1C)C(=O)N2Cc1ccccc1] | solid | 1:1 mixture of diastereomers:<br>LC/MS: 392 (M + H)⁺<br>$R_t$ = 1.00-1.50 min<br>(method B) |
| P2.7 | 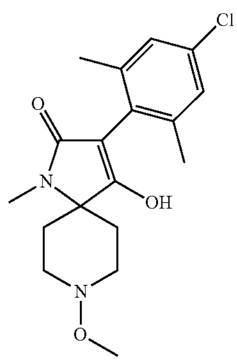 [SMILES: CON1CCC2(CC1)C(O)=C(c1c(C)cc(Cl)cc1C)C(=O)N2C] | solid | $^1$H NMR (400 MHz, DMSO-$d_6$) δ ppm 1.3-1.7 (br. m, 2H), 2.06 (s, 6H), 2.1-2.3 (br. m, 2H), 2.6-2.9 (br. m, 3H), 3.0-3.3 (br. m, 3H) 3.45 (s, 3H) 7.13 (s, 2H), 11.0 (br. s., 1H).<br>LC/MS: 351 (M + H)⁺, 349 (M − H)⁻<br>$R_t$ = 1.49 min<br>(method A) |
| P2.8 | 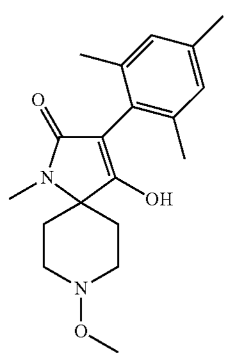 | solid | LC/MS: 329 (M − H)⁻<br>$R_t$ = 0.81 min<br>(method B) |
| P2.9 | 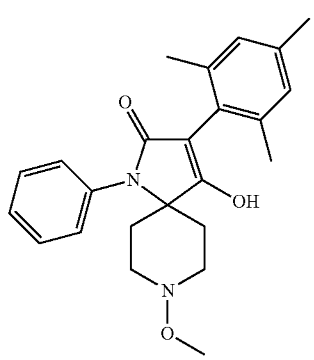 [SMILES: CON1CCC2(CC1)C(O)=C(c1c(C)cc(C)cc1C)C(=O)N2c1ccccc1] | solid | LC/MS: 391 (M − H)⁻, 393 (M + H)⁺<br>$R_t$ = 0.95 min<br>(method B) |

The invention claimed is:

1. A compound of formula (I)

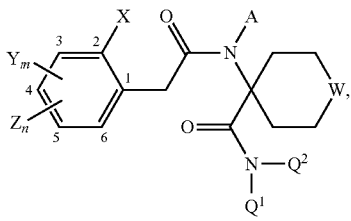

wherein
X, Y and Z independently of each other are $C_{1-4}$alkyl, $C_{3-6}$cycloalkyl, $C_{1-4}$haloalkyl, $C_{1-4}$alkoxy, $C_{1-4}$haloalkoxy, halogen, cyano, $C_{2-6}$alkenyl, $C_{2-6}$alkynyl, phenyl, or phenyl substituted by $C_{1-4}$alkyl, $C_{1-4}$haloalkyl, halogen or cyano;
m and n, independently of each other, are 0, 1, 2 or 3 and m+n is 0, 1, 2 or 3;
A is hydrogen, $C_{1-6}$alkyl, $C_{1-6}$haloalkyl, $C_{3-6}$cycloalkyl, $C_{3-6}$cycloalkyl($C_{1-4}$)alkyl, C2-6alkenyl, $C_{2-6}$haloalkenyl, $C_{3-6}$alkynyl, $C_{1-4}$alkoxy($C_{1-4}$)alkyl, benzyl, phenyl or phenyl substituted by $C_{1-4}$alkyl, $C_{1-4}$haloalkyl, $C_{1-4}$alkoxy, $C_{1-4}$haloalkoxy, halogen or cyano; and W is a group selected from $W^1$ or $W^2$;

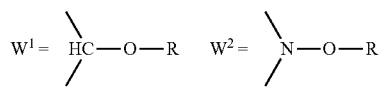

wherein R is hydrogen, $C_{1-6}$alkyl, $C_{1-6}$haloalkyl, $C_{1-6}$cyanoalkyl, $C_{2-6}$alkenyl, $C_{2-6}$haloalkenyl, $C_{3-6}$alkynyl, benzyl, $C_{1-4}$alkoxy($C_{1-4}$)alkyl or $C_{1-4}$alkoxy($C_{1-4}$)alkoxy($C_{1-4}$)alkyl;
$Q^1$ is phenyl or phenyl substituted by one or more substituent selected from the group consisting of $C_{1-4}$alkyl, $C_{1-4}$haloalkyl, $C_{1-4}$alkoxy, halogen, and nitro; and $Q^2$ is hydrogen.

2. A compound of Formula (I) according to claim 1, wherein $Q^1$ is phenyl or phenyl substituted by one or more substituent selected from methyl, ethyl, iso-propyl, trifluoromethyl, methoxy, ethoxy, fluoro, chloro and nitro.

3. A compound of Formula (I) according to claim 1, wherein A is methyl.

4. A compound of Formula (I) according to claim 1, wherein X, Y and Z independently of one another are selected from methyl, ethyl, iso-propyl, n-propyl, methoxy, fluoro, bromo or chloro, and wherein m+n is 1 or 2.

5. A compound of Formula (I) according to claim 1, wherein for both $W^1$ and $W^2$, R independently of W is hydrogen, methyl, ethyl, iso-propyl, n-propyl, tert-butyl, trifluoromethyl, 2,2,2-trifluoroethyl, allyl, propargyl, benzyl, methoxymethyl, ethoxymethyl or methoxyethyl.

6. A compound of Formula (I) according to claim 1, wherein W is W2

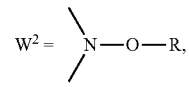

and
wherein R is selected from hydrogen, methyl, ethyl, iso-propyl, n-propyl or tert-butyl.

7. A process for preparing a compound of formula (I)

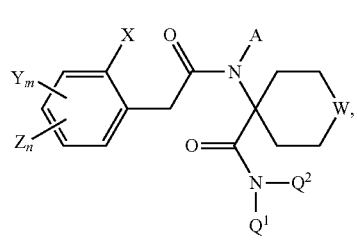

wherein X, Y, Z, m, n, A, W, and $Q^1$ are as defined in claim 1 and $Q^2$ is hydrogen; using the Ugi multi-component reaction (Ugi-MCR) with a carboxylic acid (IV), a primary amine (V), an oxo component (VI) and an isocyanide (VII) as depicted in the scheme below, where the substituents X, Y, Z, m, n, A, W, and $Q^1$ for compounds of formula (IV), (IVa), (V), (Va), (VI), (VII) and (VIII) are as defined in formula (I) and $Q^2$ is hydrogen

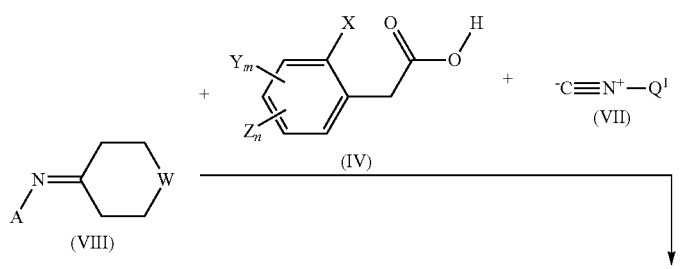

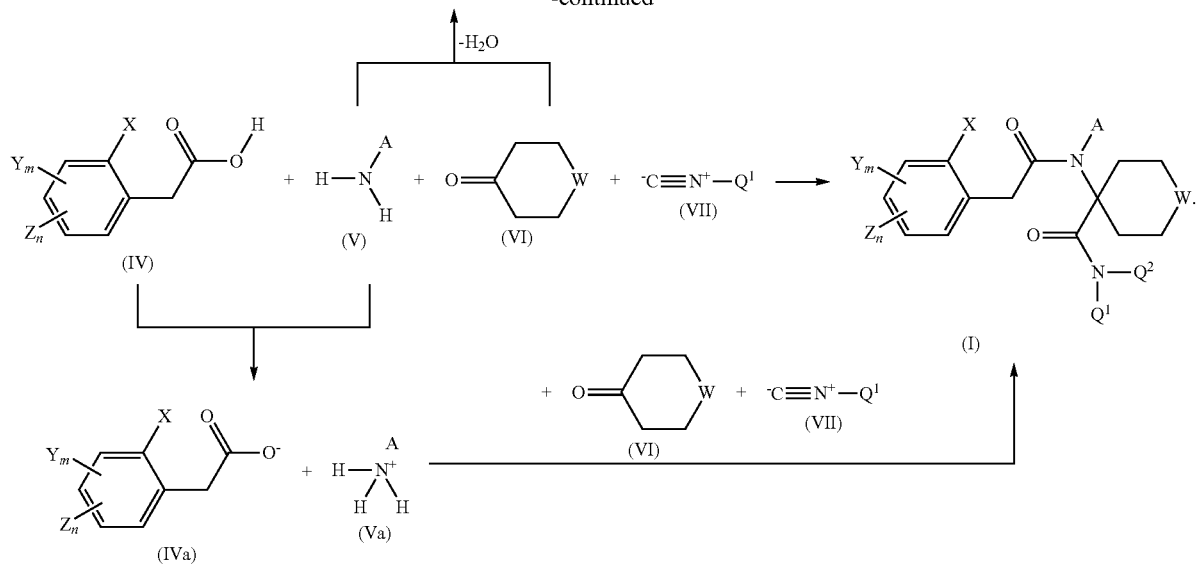

8. A compound of Formula (I) according to claim 1, wherein:

(i) X and Y are methyl, Z is chloro or methyl, wherein m and n are 1, and Y is at the 6-position and Z is at the 4-position; or (ii) X is methyl, Z is chloro or methyl, n is 1, and Z is at the 5-position;

A is hydrogen or methyl;

R is methyl for both $W^1$ and $W^2$; and $Q^1$ is phenyl or phenyl substituted by one or more substituents selected from methyl, ethyl, iso-propyl, trifluoromethyl, methoxy, ethoxy, fluoro, chloro and nitro.

9. A compound of Formula (I) according to claim 8, wherein $Q^1$ is phenyl.

10. A compound of Formula (I) according to claim 1, selected from:

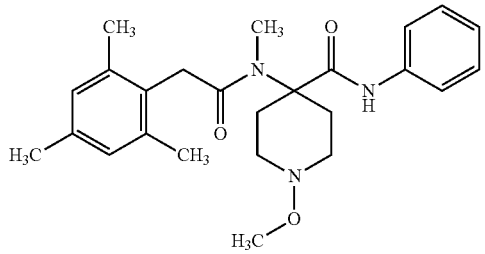

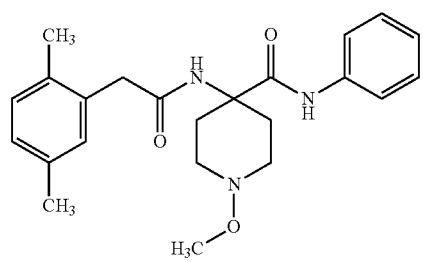

-continued

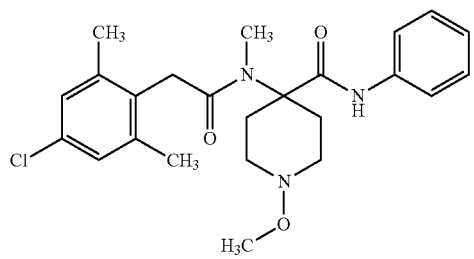

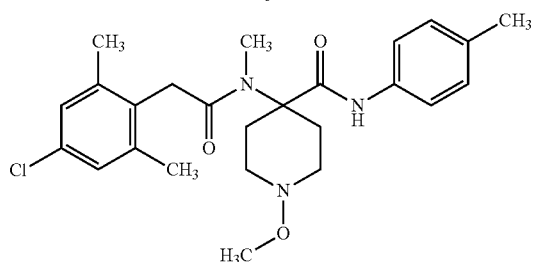

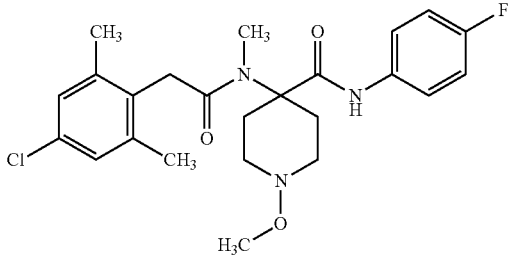

67
-continued
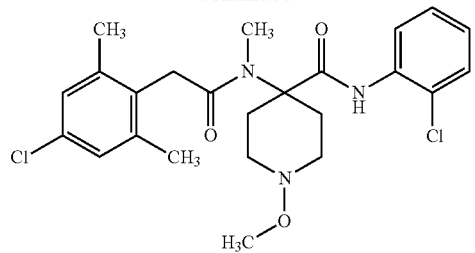
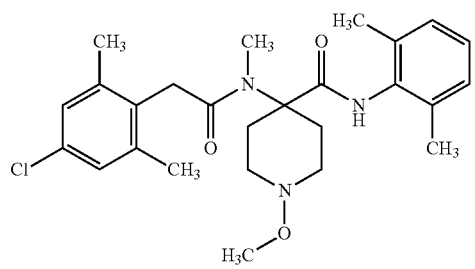
68
-continued
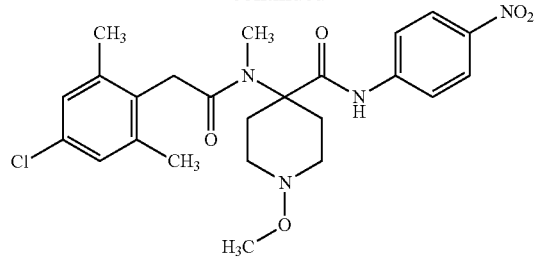
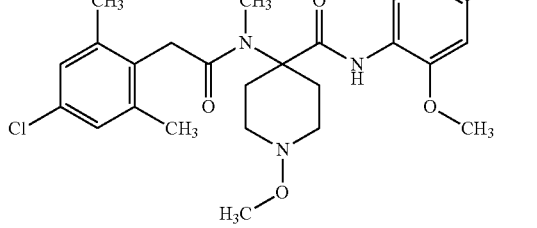
* * * * *

UNITED STATES PATENT AND TRADEMARK OFFICE
CERTIFICATE OF CORRECTION

PATENT NO. : 9,969,734 B2  Page 1 of 1
APPLICATION NO. : 14/905575
DATED : May 15, 2018
INVENTOR(S) : Edouard Godineau et al.

It is certified that error appears in the above-identified patent and that said Letters Patent is hereby corrected as shown below:

In the Claims

Column 65, Line 60, Claim 10, delete " 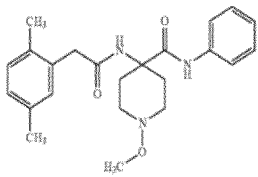 " and insert

-- 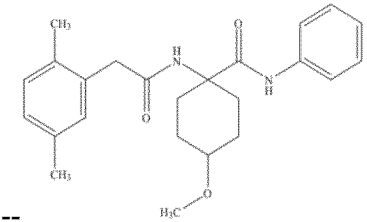 --.

Signed and Sealed this
Fifth Day of March, 2019

Andrei Iancu
*Director of the United States Patent and Trademark Office*